US011497832B2

(12) United States Patent
Ruel et al.

(10) Patent No.: US 11,497,832 B2
(45) Date of Patent: Nov. 15, 2022

(54) BIOCOMPATIBLE HYDROGEL COMPOSITIONS AND USES THEREOF

(71) Applicant: Ottawa Heart Institute Research Corporation, Ottawa (CA)

(72) Inventors: Marc Ruel, Ottawa (CA); Erik Suuronen, Ottawa (CA); Emilio Alarcon, Ottawa (CA)

(73) Assignee: Ottawa Heart Institute Research Corporation, Ottawa (CA)

( * ) Notice: Subject to any disclaimer, the term of this patent is extended or adjusted under 35 U.S.C. 154(b) by 182 days.

(21) Appl. No.: 16/610,459

(22) PCT Filed: May 4, 2018

(86) PCT No.: PCT/CA2018/050537
§ 371 (c)(1),
(2) Date: Nov. 1, 2019

(87) PCT Pub. No.: WO2018/201260
PCT Pub. Date: Nov. 8, 2018

(65) Prior Publication Data
US 2020/0345897 A1 Nov. 5, 2020

Related U.S. Application Data

(60) Provisional application No. 62/502,162, filed on May 5, 2017.

(51) Int. Cl.
*A61K 31/726* (2006.01)
*A61L 27/52* (2006.01)
(Continued)

(52) U.S. Cl.
CPC ............ *A61L 27/52* (2013.01); *A61K 31/726* (2013.01); *A61K 38/39* (2013.01); *A61L 27/20* (2013.01); *A61L 27/24* (2013.01)

(58) Field of Classification Search
CPC .................................................... A61K 31/726
See application file for complete search history.

(56) References Cited

U.S. PATENT DOCUMENTS

| 4,448,718 A | 5/1984 | Yannas et al. |
| 9,283,301 B1 | 3/2016 | Simionescu et al. |
| (Continued) | | |

FOREIGN PATENT DOCUMENTS

| CA | 2 491 788 A1 | 6/2005 |
| CN | 103554527 B | 2/2014 |
| (Continued) | | |

OTHER PUBLICATIONS

Hanthamrongwit et al. (Biomaterials 1996, vol. 17 No. 8.) . (Year: 1996).*

(Continued)

*Primary Examiner* — Benjamin J Packard
(74) *Attorney, Agent, or Firm* — Fox Rothschild LLP

(57) ABSTRACT

Provided herein are biocompatible and/or biodegradable hydrogel compositions comprising native collagen and chondroitin sulfate, the collagen and chondroitin sulfate being chemically cross-linked thereby forming a matrix. The native collagen may comprise recombinant human collagen type I (rHCI), recombinant human collagen type III (rHCIII), or a combination thereof, for example. Methods and uses thereof for regeneration or repair of tissue, improvement of tissue function, mechanical stabilization of tissue, prevention of tissue damage, or prevention of tissue loss of function are described, particularly with respect to cardiac tissue and myocardial infarction events.

21 Claims, 18 Drawing Sheets

(51) Int. Cl.
*A61K 38/39* (2006.01)
*A61L 27/20* (2006.01)
*A61L 27/24* (2006.01)

(56) References Cited

U.S. PATENT DOCUMENTS

2014/0142200 A1* 5/2014 Duan .................. A61L 15/325
 514/773
2016/0243282 A1 8/2016 Simionescu et al.

FOREIGN PATENT DOCUMENTS

CN 106943632 A 7/2017
WO WO 2016197038 A1 12/2016

OTHER PUBLICATIONS

Flanagan et al (Biomaterials 27 (2006) 2233-2246). (Year: 2006).*
International Search Report and Written Opinion, Appl. No. PCT/CA2018/050537, dated Aug. 15, 2018.
Zhou X. et al. , "Genipin cross-linked type II collagen/chondroitin sulfate compositehydrogel-like cell delivery system induces differentiation of adipose-derived stem cells and regenerates degenerated nucleus pulposus," Acta Biomaterialia 71 (2018) pp. 496-509.
Cao, H. et al., "EDC/NHS-crosslinked type II collagen-chondroitin sulfate scaffold: characterization and in vitro evaluation", Journal of Materials Science: Materials in Medicine 2008, vol. 19 (2), pp. 567-575.
Tamaddon, M. et al. , "Characterization of freeze-dried type II collagen and chondroitin sulfate scaffolds.", Journal of Materials Science: Materials in Medicine 2013, vol. 24 (5), pp. 1153-1165.
Madhavan, K. et al., "Evaluation of composition and crosslinking effects on collagen-based composite constructs," Acta Biomaterialia Apr. 2010, vol. 6 (4), pp. 1413-1422.
Extended Supplementary European Search Report, Application No. 18795198.3, dated Nov. 27, 2020.
Zhou Xiang et al. "Collagen-GAG Scaffolds Grafted onto Myocardial Infarcts in a Rat Model: A Delivery Vehicle for Mesenchymal Stem Cells", Tissue Engineering, vol. 12, No. 9, Sep. 1, 2006 pp. 2467-2478, XP055754693.
Liu et al., "Recombinant Human Collagen for Tissue Engineered Corneal Substitutes", Biomaterials, Elsevier, Amsterdam, NL, vol. 29, No. 9, Jan. 17, 2008, pp. 1147-1158, XP022425174.
Hanan Stein et al.: "Production of Bioactive, Post-Translationally Modified, Heterotrimeric, Human Recombinant Type-I Collagen in Transgenic Tobacco", Biomacromolecules, American Chemical Society, US, vol. 10, No. 9, Sep. 14, 2009, pp. 2640-2645, XP008159867.
Oded Shoseyov et al., Human Collagen Produced in Plants: More Than Just Another Molecule, Bio Engineered, vol. 5, No. 1, Aug. 9, 2013, pp. 49-52, XP055633616.
Suuronen E J et al., Tissue-Engineered Injectable Collagen-Based Matrices for Improved Cell Delivery and Vascularization of Ischemic Tissue Using CD133+ Progenitors Expanded From the Peripheral Blood, Circulation, American Heart Association, Inc., US, vol. 114, No. 1 Suppl , Jul. 4, 2006, pp. I138-I144. XP002482181.
Raub, C. R. et al., "Image Correlation Spectroscopy of Multiphoton Images Correlates with Collagen Mechanical Properties" Biophysical Journal (2008); vol. 94, pp. 2361-2373.
Carey, S. P., et al., "Biophysical Control of Invasive Tumor Cell Behavior by Extracellular Matrix Microarchitecture" Biomaterials (2012); vol. 33:16; pp. 4157-4165.
Pupkaite, J. et al., "Delivering More of an Injectable Human Recombinant Collagen III Hydrogel Does Not Improve its Therapeutic Efficacy for Treating Myocardial Infarction"; ACS BioMater. Sci. Eng. (2020); vol. 6; pp. 4256-4265.

* cited by examiner

Reference Image of T-piece with Theracol Added

Reference Image of T-piece with 40% Chondroitin Added

Reference Image of T-piece with EDC/NHS Mixture Added

Reference Image of T-piece with NaOH Added

BIOCOMPATIBLE HYDROGEL COMPOSITIONS AND USES THEREOF

This application is a 371 filing of International Patent Application PCT/CA2018/050537 filed May 4, 2018, which claims the benefit of U.S. provisional application No. 62/502,162 filed. May 5, 2017.

FIELD OF INVENTION

The present invention relates generally to hydrogel compositions. More specifically, the present invention relates to hydrogel compositions comprising native collagen and chondroitin sulfate, and uses thereof.

BACKGROUND

Heart diseases alone are responsible for one-third of the deaths in North America and pose a tremendous burden on the health care systems. Thus, developing therapies to self-heal the damaged heart post-infarction is of significant interest. Therapies including realistic translational components are particularly sought after.

According to the World Health Organization, cardiovascular diseases (CVD) are the number one cause of worldwide morbidity and are responsible for over 17 million deaths annually. Coronary artery disease remains the most common CVD and is usually caused by atherosclerotic buildup in the arteries,[100] which restricts blood flow leading to myocardial infarction (M).[101] Surgical procedures that restore blood flow to the injured cardiac muscle post-MI improve patient outcome; however, they fail to restore cardiac function. Therefore, on average, 10% of MI-patients develop adverse ventricular remodeling that will ultimately lead to advanced heart failure (HF),[101] which has a five-year mortality of ≈50%.[98]

Heart disease, including myocardial infarction (MI), is amongst the leading causes of morbidity in Canada.[1] Despite medical interventions aimed at restoring blood supply post-MI that improve patient outcome, these fail at preventing irreversible muscle loss. In 10% of such cases, progressive ventricular remodeling will ultimately lead to advanced heart failure (HF) and death.[4] It has become increasingly evident that current conventional small-molecule drugs, growth factors, and cell-based therapies are sub-optimal for restoring heart function post-MI.[2, 3]

Numerous research groups have focused on stem cell therapies, with no long-term success in clinical trials,[4] and marginal benefits in the clinic;[5, 6, 7, 8, 9, 10] showing 2.2-3.9% improvement in left ventricle ejection fraction (LVEF) at 6-12 months post-MI, and 1.9% beyond a year.[11] Such difficulties may be, at least in part, a consequence of the hostile environment found in a post-MI heart that includes poor blood supply, limited oxygen, inflammation, and scarring, which together are believed to contribute to the low cell engraftment and functional regeneration.[12, 13, 14, 15, 16, 17]

The adult mammalian heart is primarily composed of terminally differentiated cardiomyocytes, which limits its ability to self-heal.[18] Thus, degradation and subsequent modification of the cardiac extracellular matrix (ECM) in the early stages post-MI,[19, 20, 21, 22] is directly related to irreversible heart damage and progression of HF.[21] These two factors limit, for example, cell engraftment and functional regeneration.[102] Such irreversible changes disrupt cell-ECM interactions that are required for cell signaling, function, and survival.[23, 24, 25] Remarkably, it has been shown that preserved ECM in a decellularized heart can support new tissue formation by seeded stem cells,[26] highlighting the importance of functional ECM for effective heart tissue regeneration. Collagens are the main component of the native cardiac ECM,[27] with type I and III collagens being the most abundant at ~70% and ~12% of the total protein content in the myocardium, respectively.[28, 29, 30, 31, 32] In the heart, type I collagen contributes to ventricular stiffness and helps to maintain the heart's shape, while type III collagen is found in the contractile structure surrounding the cardiomyocytes.[33, 34] The tensile strength of collagenous fibers, mainly type I collagen, has been compared with that of steel, whereas collagen type III is considerably more elastic.[35] A delicate balance between the two collagen types within the myocardium is relevant for maintaining normal contractility and cell viability.[36] The ratio of collagen type I and III naturally increases with age,[37, 38] and correlates with a progressive increase in ventricular wall thickness. The increase in type I collagen content with aging may contribute to the decrease in the ventricular elasticity of the myocardium in the elderly.[39] Further, the relative abundance of type III collagen increases in the ischemic myocardium,[40] as a result of unbalanced production/degradation caused by changes in inflammation mediated by matrix metalloproteinases (MMPs) activation and from collagen deposition from fibro/myoblast activation.[41, 42] It has been reported that inhibition or knockout of MMPs in the heart (or myocardium) resulted in enhanced tissue survival post-MI in pre-clinical models, highlighting the relevance of ECM preservation for preventing cardiac remodeling.[43]

Engineered soft biomaterials, which can be delivered by a needle or catheter and subsequently form a 3D-structure within the infarcted myocardium[44] are able to provide structural support to the infarcted heart. Numerous biodegradable natural biopolymers have been tested in large pre-clinical MI-models.[45, 46, 47, 48] Overall, results have shown improvements in diastolic function, preservation of global cardiac function and prevention of cardiac remodeling. Alginate-based materials have shown promise in pre-clinical studies and are currently in phase II clinical trials.[49, 50] However, alginate is bio-inert, and evidence suggests that its passive structural reinforcement alone may be insufficient for long-term prevention of pathological ventricular remodeling.[51]

Injectable biomaterials composed of ECM proteins can more closely mimic the cardiac structure and consequently promote tissue revascularization, and repair. Simulating the native cell environment using collagen provides a unique porous matrix, which has been shown to promote cell angiogenesis, tissue integration, and decreased inflammation.[52, 53] Collagen-based biomaterials are currently being used in several tissue-engineered products under development and being pre-clinically tested.[54, 55, 56] Since collagens are integral parts of the cardiac wall,[27] studies have shown that collagen-based biomaterials can provide mechanical support, limit maladaptive remodeling, and improve neovascularization and function of MI hearts.[57, 58, 59, 60] More recently, the safety and efficacy of a decellularized ventricular ECM material in treating MI was demonstrated in a pre-clinical porcine model.[61] Furthermore, it has been shown that collagen-based injectable materials reduced levels of inflammation and apoptosis, increased tissue vascularity, and preserved cardiac morphology and function in mice post-MI.[59, 62 56, 63, 64, 65, 66, 67, 68]

However, to this day, materials tested are typically of animal origin and batch-to-batch differences, presence of viruses, bacteria, and even endotoxins add to the inherent risk of immune reactions and contribute to limiting their clinical applicability.[69, 70] Further, it is believed that the use of type III collagen, the second most abundant collagen in the heart, which is also the elastic component in a healthy heart muscle, has not yet been explored.[35] As well, hydrogels comprising collagen and additional components, preparation methods therefor, and physical characteristics and therapeutic applications thereof, have not been fully studied in the art.

Alternative, additional, and/or improved hydrogels for tissue treatment are desirable.

SUMMARY OF INVENTION

Provided herein are hydrogel compositions comprising collagen and chondroitin sulfate, as well as uses thereof in the regeneration/repair of tissue.

In an embodiment, there is provided herein a biocompatible and/or biodegradable hydrogel composition comprising collagen and chondroitin sulfate, the collagen and chondroitin sulfate being at least partially chemically cross-linked thereby forming a matrix.

In another embodiment, the collagen is native collagen and may comprise recombinant human collagen type I (rHCI), recombinant human collagen type III (rHCIII), or a combination thereof.

In yet another embodiment, the native collagen and the chondroitin sulfate may be chemically cross-linked by 1-ethyl-3-(3-dimethylaminopropyl)carbodiimide (EDC)-N-hydroxysuccinimide (NHS) chemical coupling reaction. Cross linking by other linkers and cross linking agents is also possible as would be understood by a person of skill in the art.

In still another embodiment, the hydrogel composition has a denaturation temperature greater than about 45° C., for example, but not limited to 45° C., 46° C., 47° C., 48° C., 49° C., 50° C. or higher.

In another embodiment, the hydrogel composition after crosslinking preferably exhibits a viscosity of about 9 to 150 Pa·s at 37° C., for example 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 136, 138, 139, 140, 141, 142, 143, 144, 145, 146, 147, 148, 149, or 150 Pa·s at 37° C. In a further embodiment the viscosity is about 36±21 Pa·s at 37° C. for rHCI or about 104±32 Pa·s at 37° C. for rHCIII, after crosslinking.

In yet another embodiment, the hydrogel composition gels at 37° C. in less than about 10 min, for example but not limited to 9, 8, 7, 6 or 5 minutes.

In still another embodiment, the hydrogel matrix may have a pore size range of about 5 to about 50 μm, for example, but not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or any values defining a range therein, for example, but not limited to about 10 to about 25 μm.

In another embodiment, the hydrogel matrix may be degraded by 10 U/mL type I collagenase in PBS solution at 37° C. at a rate of about 0.1 to about 2 mg/s, such as about 0.15 to about 0.65 mg/s.

In another embodiment, a mass ratio of native collagen to chondroitin sulfate may be about 1:4. Higher ratios and lower ratios are also contemplated, however.

In still another embodiment, the native collagen and the chondroitin sulfate may be chemically cross-linked by EDC-NHS cross-linking agent, and a mass ratio of native human collagen to chondroitin sulfate to NHS to EDC may be about 1:4:0.5:0.3. Other ratios are also contemplated. For example, but not wishing to be limiting in any manner, hydrogel compositions may be prepared that vary in the amount of collagen, chondroitin sulfate, NHS or EDC from the ratio provided above. In this regard, hydrogel compositions have been prepared and tested wherein the concentration of NHS has been diluted by ½, ⅕, ⅒ and 1/15 from that described above.

In another embodiment, the native collagen may be rHCI, the rHCI and the chondroitin sulfate may be chemically cross-linked by EDC-NHS chemical coupling reaction at a mass ratio of rHCI to chondroitin sulfate to NHS to EDC of about 1:4:0.5:0.3, and the hydrogel matrix may have a denaturation temperature of about 46° C., a viscosity of about 36±21 Pa·s at 37° C. after crosslinking, a matrix pore size of about 11 μm, and the matrix may be degraded by 10 U/mL type I collagenase in PBS solution at 37° C. at a rate of about 0.5 mg/s.

In another embodiment, the native collagen may be rHCIII, the rHCIII and the chondroitin sulfate may be chemically cross-linked by EDC-NHS chemical coupling reaction at a mass ratio of rHCIII to chondroitin sulfate to NHS to EDC of about 1:4:0.5:0.3, and the hydrogel matrix may have a denaturation temperature of about 50° C., a viscosity of about 104±32 Pa·s at 37° C. for rHCIII, after crosslinking, a matrix pore size of about 24 μm and the matrix may be degraded by 10 U/mL type I collagenase in PBS solution at 37° C. at a rate of about 0.2 mg/s.

In another embodiment, the native collagen may comprise a combination of rHCI and rHCIII.

In still another embodiment, the hydrogel composition may be for use in regeneration or repair of tissue, improvement of tissue function, mechanical stabilization of tissue, prevention of tissue damage, or prevention of tissue loss of function.

In another embodiment, there is provided herein a use of a hydrogel composition as defined above for regeneration or repair of tissue, improvement of tissue function, mechanical stabilization of tissue, prevention of tissue damage, or prevention of tissue loss of function.

In another embodiment, there is provided herein a use of a hydrogel composition as defined above in the manufacture of a medicament for regeneration or repair of tissue, improvement of tissue function, mechanical stabilization of tissue, prevention of tissue damage, or prevention of tissue loss of function.

In certain embodiments of the above uses, the tissue may be cardiac tissue.

In still another embodiment, the hydrogel composition may be for treating myocardial infarction or other cardiac ischemia. In further embodiments, the hydrogel composition may be for injection to the heart following a myocardial infarction or ischemic event. In yet another embodiment, the hydrogel composition may be for administration to the heart by injection at a single time-point or by a plurality of injections at multiple time-points following the myocardial infarction or ischemic event.

In certain embodiments, the hydrogel composition may be for preventing loss of cardiac mechanical properties, preventing cardiac remodeling, reducing fibrosis and/or infarct area, improving vascularity of infarcted heart muscle, or improving cardiac function following the myocardial infarction or ischemic event.

In certain embodiments, the native collagen may comprise rHCI, rHCIII, or both.

In another embodiment, there is provided herein a method for regenerating or repairing tissue, improving tissue function, mechanically stabilizing tissue, preventing tissue damage, or preventing tissue loss of function in a subject in need thereof, said method comprising:
providing a hydrogel composition as defined above; and
administering said hydrogel composition into affected tissue of the subject.

In a further embodiment of the above method, the tissue may be cardiac tissue.

In still another embodiment of the above method or methods, the hydrogel composition may be administered by injection to the heart following a myocardial infarction or ischemic event.

In yet another embodiment of the above method or methods, wherein the hydrogel composition may be administered to the heart by injection at a single time-point or by a plurality of injections at multiple time-points following the myocardial infarction or ischemic event.

In still another embodiment of the above method or methods, the hydrogel composition may prevent loss of cardiac mechanical properties, prevent cardiac remodeling, reduce fibrosis and/or infarct area, improve vascularity of infarcted heart muscle, or improve cardiac function following the myocardial infarction or ischemic event.

In certain embodiments, the native collagen may be rHCI, rHCIII, or a combination thereof.

In another embodiment, there is provided herein a use of a hydrogel composition as defined above for the treatment of myocardial infarction.

In another embodiment, there is provided herein a use of the hydrogel composition as defined above in the manufacture of a medicament for the treatment of myocardial infarction.

In yet another embodiment, there is provided herein a method for treating a myocardial infarction event in a subject in need thereof, said method comprising:
providing a hydrogel composition as defined above; and
injecting said hydrogel composition into affected heart tissue of the subject following the myocardial infarction event.

In still another embodiment, there is provided herein a use of a hydrogel composition as defined above for treating a myocardial infarction event in a subject, wherein the hydrogel composition is for injection into affected heart tissue of the subject following the myocardial infarction event.

In certain embodiments, treatment of myocardial infarction may comprise regeneration or repair of tissue, improvement of tissue function, mechanical stabilization of tissue, prevention of tissue damage, or prevention of tissue loss of function.

In other embodiments, treatment of myocardial infarction may comprise preventing loss of cardiac mechanical properties, preventing cardiac remodeling, reducing fibrosis and/or infarct area, improving vascularity of infarcted heart muscle, or improving cardiac function following the myocardial infarction event.

In still further embodiments, the native collagen may be rHCI, rHCIII, or a combination thereof.

In another embodiment, there is provided herein a method for preparing a hydrogel composition as defined above, said method comprising:

providing a solution of native collagen;
providing a solution of chondroitin sulfate;
providing an EDC and NHS solution;
mixing the solution of native collagen with the solution of chondroitin sulfate, thereby forming a first mixed solution; and
mixing the first mixed solution with the EDC and NHS solution, thereby initiating cross-linking of the native collagen and chondroitin sulfate to form a hydrogel matrix composition.

In a further embodiment, the mixing steps may be performed using syringes and a connecting enclosed mixing system so as to maintain the hydrogel composition under controlled and aseptic conditions.

In yet another embodiment, a mass ratio of native collagen to chondroitin sulfate to NHS to EDC in the chemical cross-linking mixing step may be about 1:4:0.5:0.3.

In still another embodiment, the solution of native collagen may be a 1% w/v solution. In yet another embodiment, the solution of chondroitin sulfate may be a 40% chondroitin sulfate solution.

In still another embodiment, the EDC and NHS solution may be prepared by mixing a 5% w/v NHS solution and a 3% w/v EDC solution in a 1:1 ratio.

In yet another embodiment, the above preparation method or methods may further comprise a step of adding an NaOH solution to the chemically cross-linked hydrogel composition to adjust the pH of the hydrogel composition to a physiologically acceptable level.

In yet another embodiment, the above preparation method or methods may further comprise a step of pouring the resulting hydrogel composition into a well or mold.

In another embodiment, there is provided herein a method for treating a myocardial infarction event in a subject, said method comprising:
preparing a hydrogel composition as defined above using a method as defined above; and
directly injecting the prepared hydrogel composition into affected heart tissue of the subject following the myocardial infarction event.

In still another embodiment, there is provided herein a use of a hydrogel composition as defined above for treating a myocardial infarction event in a subject, wherein said hydrogel composition is for injection into affected heart tissue of the subject after the myocardial infarction event directly following preparation of the hydrogel composition by a method as defined above.

BRIEF DESCRIPTION OF DRAWINGS

These and other features of the present invention will be further understood with reference to the following description and accompanying drawings, wherein:

FIG. 13 also provides images for immunofluorescence tissue sections of infarcted myocardium areas of the heart treated with PBS, rHCI, and rHCIII (B); and the total number of positive CD206 per mm$^2$ counted in different areas post-myocardial infarction in the border zone (BZ), infarcted tissue (I), and, remote zone (RZ) (B'), see experimental section of Example 1 for further detail. Emission fluorescence shown in the figure corresponds to positive CD206 cells (anti-CD206 AF488 green), DAPI nuclei staining is shown in blue. Scale bars in the images correspond to 50 μm. Numbers reported in the Figure correspond to the average of 6-7 samples, and ±bars correspond to standard error. FIG. 13 further shows the number of positive GFP cells measured in left ventricle of Cxcr3-EGFP infarcted animals 2 days post treatment with PBS, rHCI, and rHCIII (C1) (n=8, measured by flow cytometry) and double immune staining cells (GFP, 488 nm excitation channel) measured for F4/80 (C2), CD38 (C3), and CD11b (C4), ±bars correspond to standard error. Also provided are representative images for immunofluorescence tissue sections of border zone areas of myocardium of CB57 hearts treated with PBS, rHCI, and rHCIII (D). Emission fluorescence shown in the figure corresponds to positive Troponin (red), WGA positive (green), and DAPI nuclei staining in blue. Scale bars in the images correspond to 50 μm. Total area of positive Troponin per mm$^2$ counted from the border zone is shown in (D'). ±bars correspond to standard error. p values calculated from two tail t-test;

FIG. 16 also provides example images for hearts harvested 28 days post-injection (G) (size bar corresponds to 2.0 mm) and a scatter plot for the heart mass/tibia-length ratio (H) measured 28 days post-injection of PBS, rHCI, and rHCIII-based collagen hydrogel matrices, and Young's modulus (YM) for left ventricle measured 2 or 28 days post-injection (I). Representative H&E histological heart sections for samples harvested 28 days post-treatment show representative hemolysin and eosin staining are shown in (J) (scale bar corresponds to 1 mm); infarct size as a percentage of left ventricle calculated at 28 days post-treatment from H&E histology sections is shown in (K) (n=8; p values were calculated from multi-parametric statistical analysis as per the experimental section of Example 1); and posterior wall thickness (PW) measured at 28 days post-treatment from H&E histology (n=8) is shown in (L). Error bars are the standard errors to the mean value. Unless otherwise indicated, p values were calculated from t-tests analysis.

DETAILED DESCRIPTION

Figure 1:
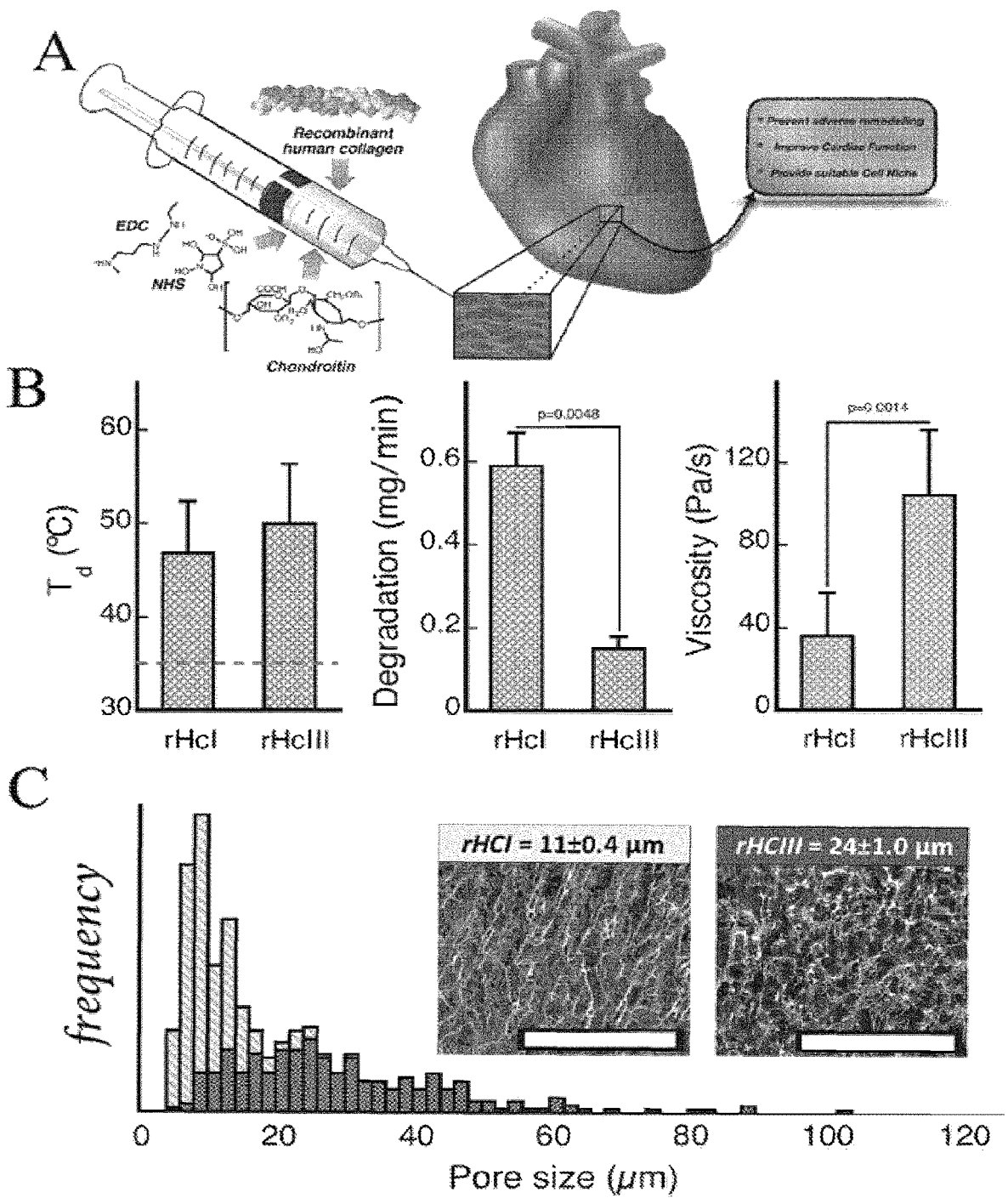
FIG. 1 shows preparation and physical characterization of injectable human recombinant collagen for treatment of infarcted cardiac tissue. (a) shows a schematic depicting injection of embodiments of human recombinant based-collagen hydrogel matrices (1.0% w/w) containing the pro-angiogenic chondroitin sulfate C as described herein into heart tissue for cardiac tissue repair; (b) shows thermal gelation of these hydrogels (37° C., ≤10 min), resulting in 3D structures with denaturation temperatures (Td, ° C.; n=3) of >45° C., and also the susceptibility to enzymatic degradation with collagenase in vitro (mg/min; n=3), and the viscosity (Pa·s; n=7) after crosslinking for the rHCI and rHCIII-based collagen hydrogels (or matrices); and (c) shows the porous structure of said hydrogels, with average pore sizes for the collagen hydrogels rHCI (gray bars) and rHCIII (black bars) measured from 250 individual pores per collagen sample. Average pore sizes of about 10 and about 25 μm were found for rHCI and rHCIII, respectively. Inset: Representative Cryo-SEM images for the collagen matrices prepared in this work. Numbers included in the images correspond to the mean size±standard errors for the pore sizes. Scale bar corresponds to 200 μm. Error bars in B correspond to standard deviations from the mean value. p values showed in the figures were calculated from two tail t-test for samples with unequal variance.
Figure 2:
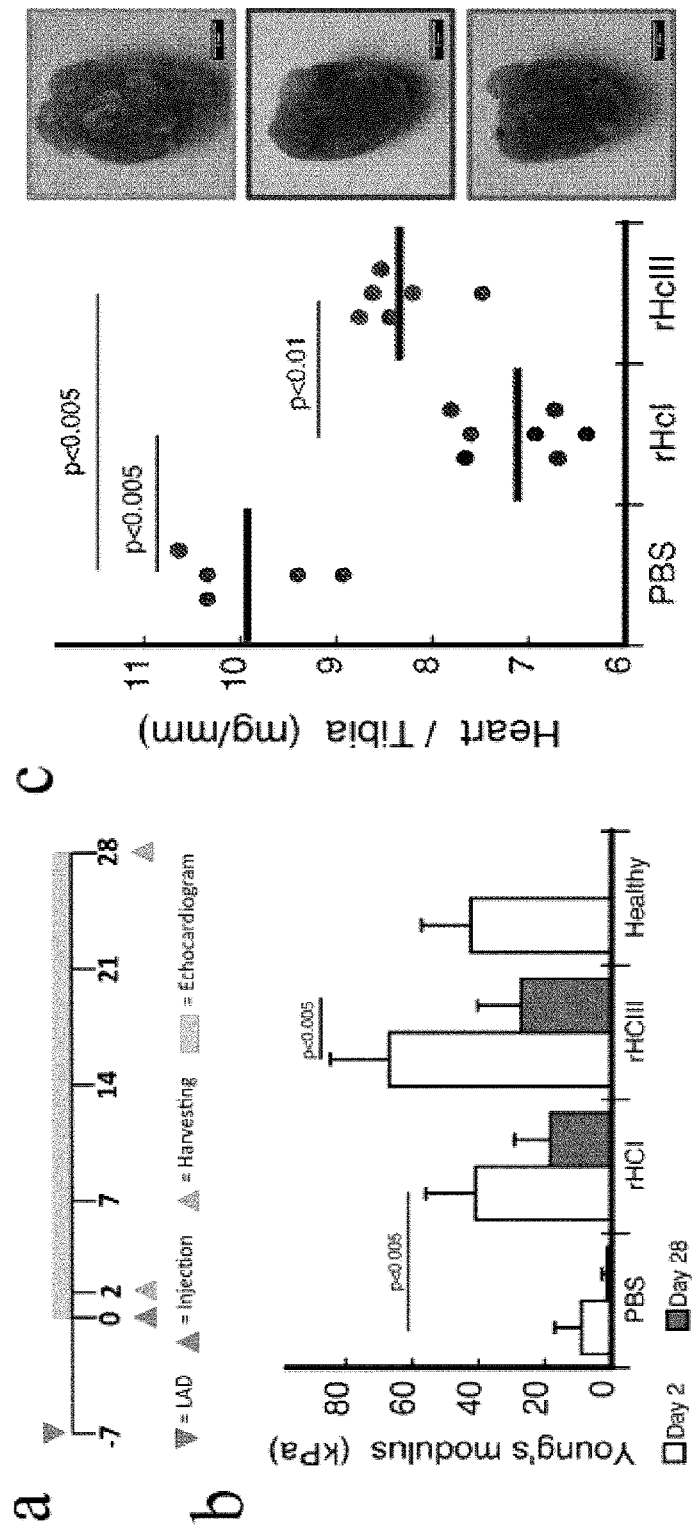
FIG. 2 shows in vivo experiments designed to assess the suitability of hydrogel composition embodiments for improving, or preserving, cardiac function in an established scar by directly targeting infarct wall thinning at 7 days post-MI (a); results at 2-days post-treatment using hydrogel composition embodiments, indicating a recovery of the mechanical properties of the infarcted heart post-injection (p<0.001) (b); and cardiac remodeling (heart size and weight) results for treated and control animals showing maintenance of heart morphology in hydrogel-treated hearts (c)
Figure 3:
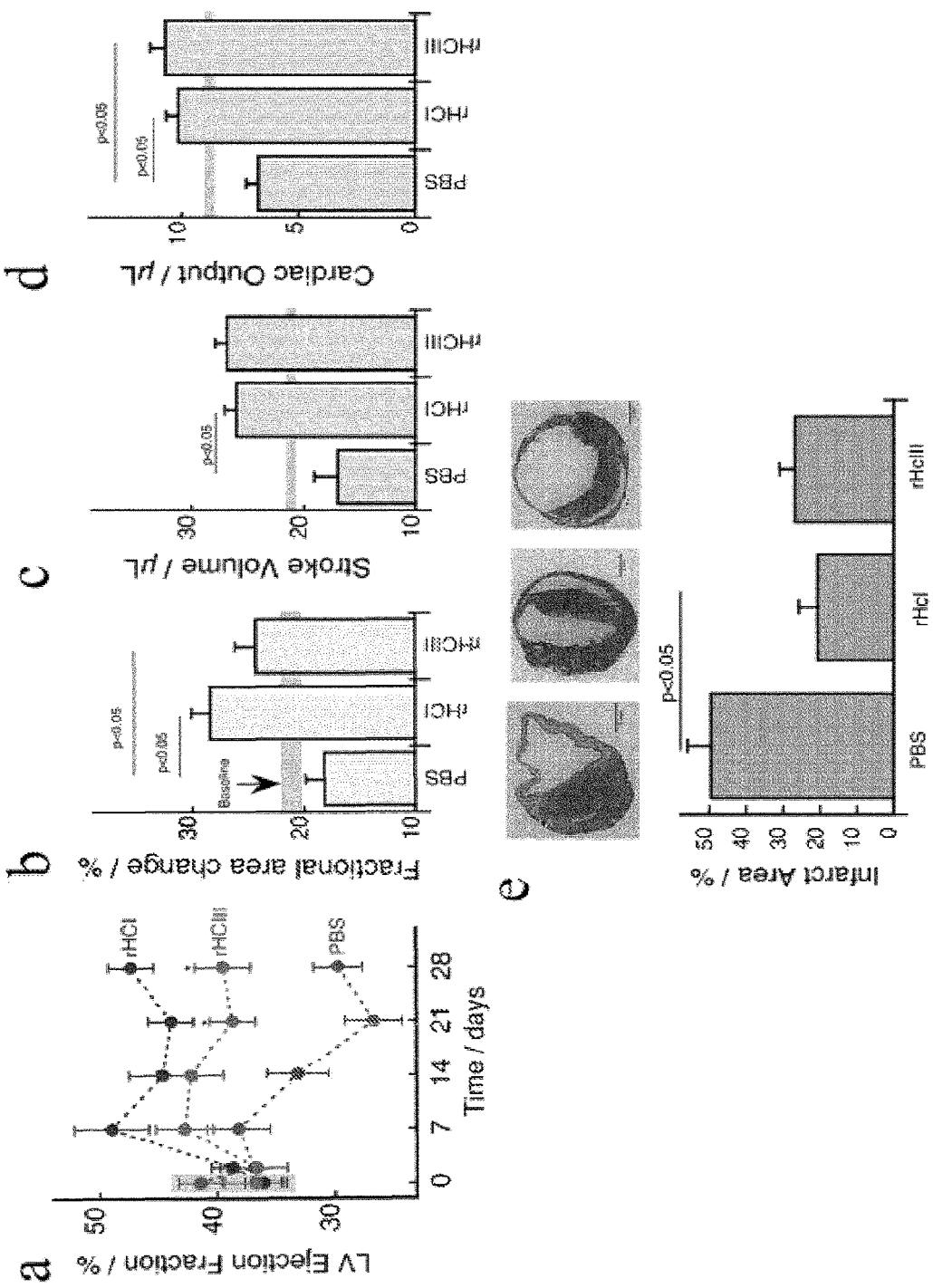
FIG. 3 shows cardiac function for untreated subjects and subjects treated with hydrogel composition embodiments, determined by Left Ventricle Ejection fraction, LVEF, measured over time up to 28 days post-treatment (a); and data measured after 28 days for Fractional area change, FAC (b); Stroke volume, SV (c); cardiac output, CO (d); and infarct size (e)
Figure 4:
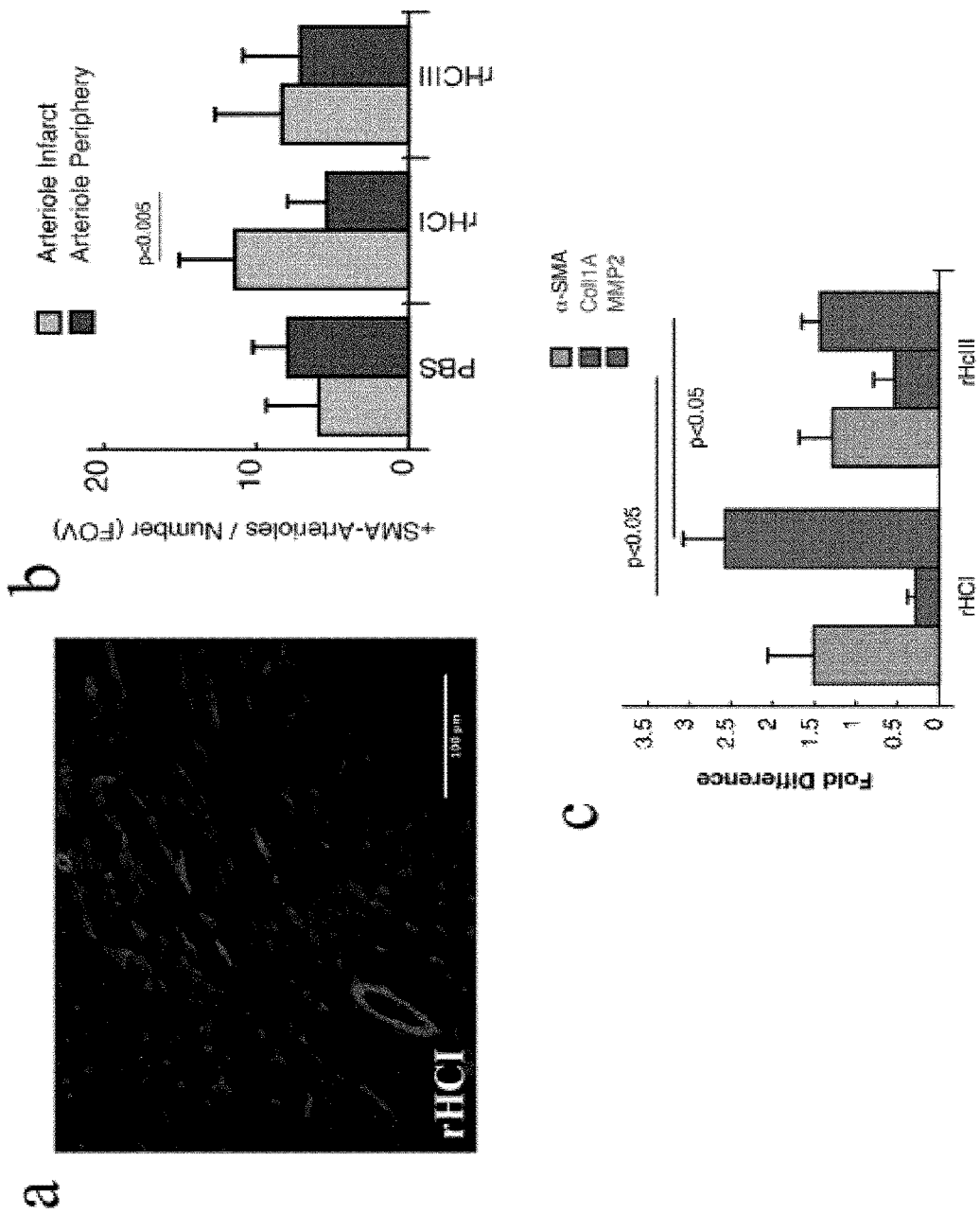
FIG. 4 shows immunohistochemistry experiments carried out for determining vascular density of the different groups at day 28 (a and b); and the in-vitro effect of isolated mouse cardiac fibroblasts seeded onto 300 μm layers of the hydrogels, rHCI or rHCIII, and cultured for 5 days (c)
Figure 5:
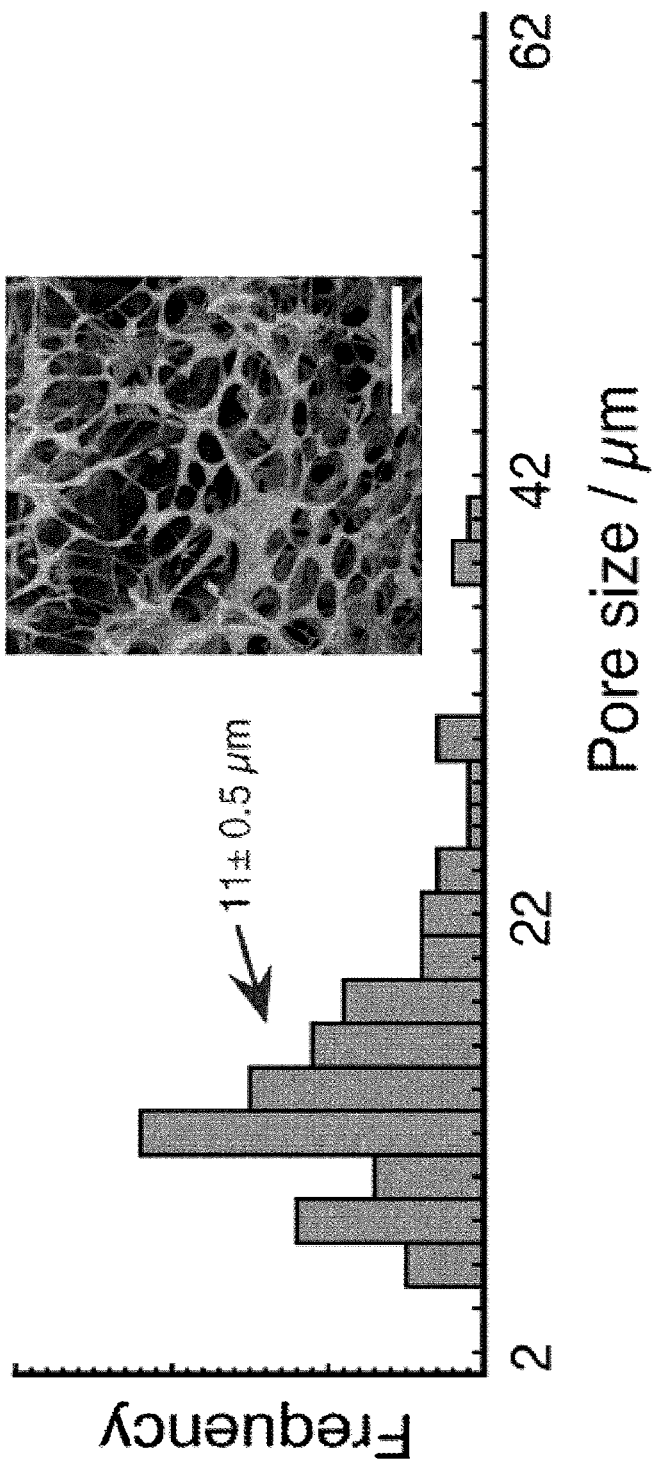
FIG. 5 shows the mean average for pore diameter for type I rat tail collagen matrices measured from 400 individual pores per collagen sample is shown. Inset: Representative Cryo-SEM image for the collagen matrices. Numbers included in the images correspond to the mean size±standard errors for the pore size. Scale bar corresponds to 200 μm.
Figure 6:
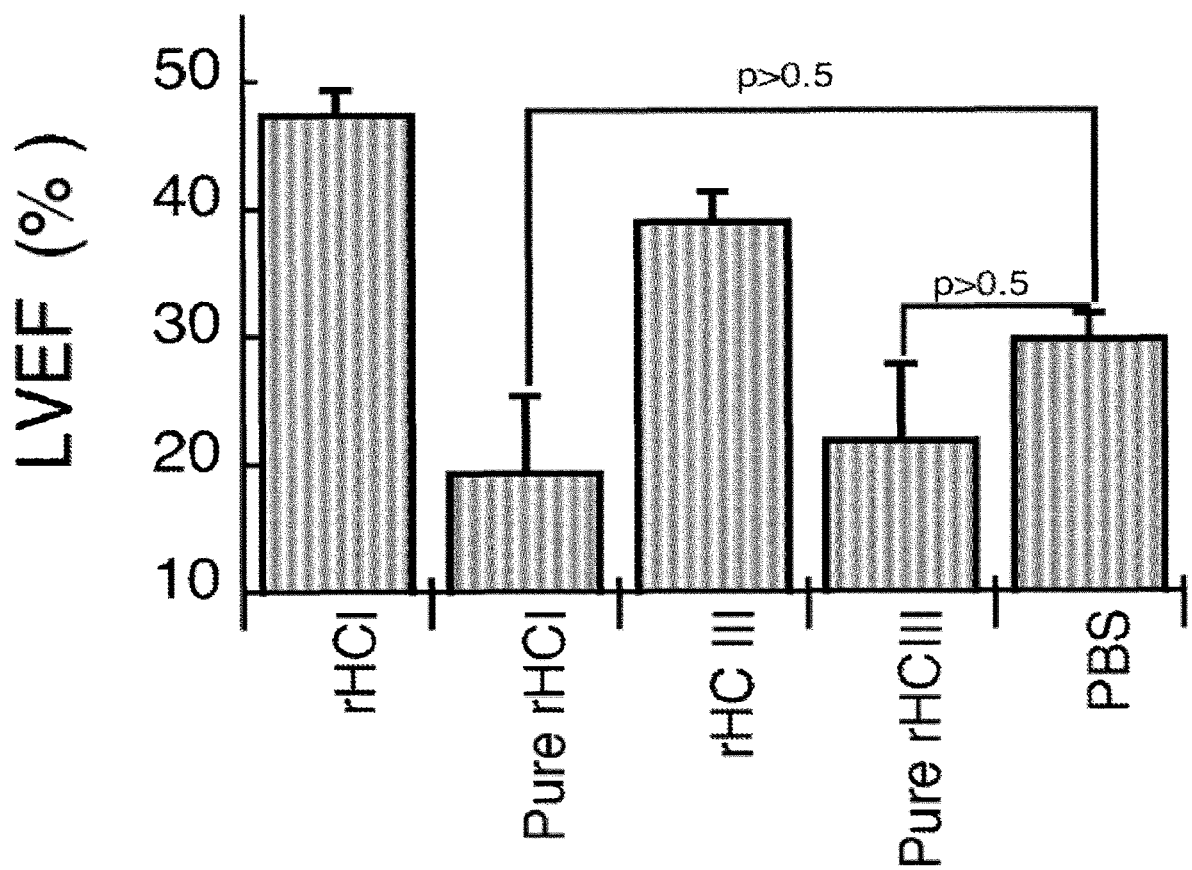
FIG. 6 shows results comparing the LVEF for treated and untreated subjects 28 days post-injection. Unmodified rHCI and rHCIII protein was used as an additional control to demonstrate that the effect of hydrogel formation on therapeutic activity. Changes in LVEF % for collagen matrices (rHCI and rHCIII) and non-crosslinked collagen solutions (pure rHCI and pure rHCIII) is shown. Sample sizes for pure rHCI and rHCIII were n=4. p values showed in the figure were calculated from t-test for non-paired data with unequal variance.
Figure 7:
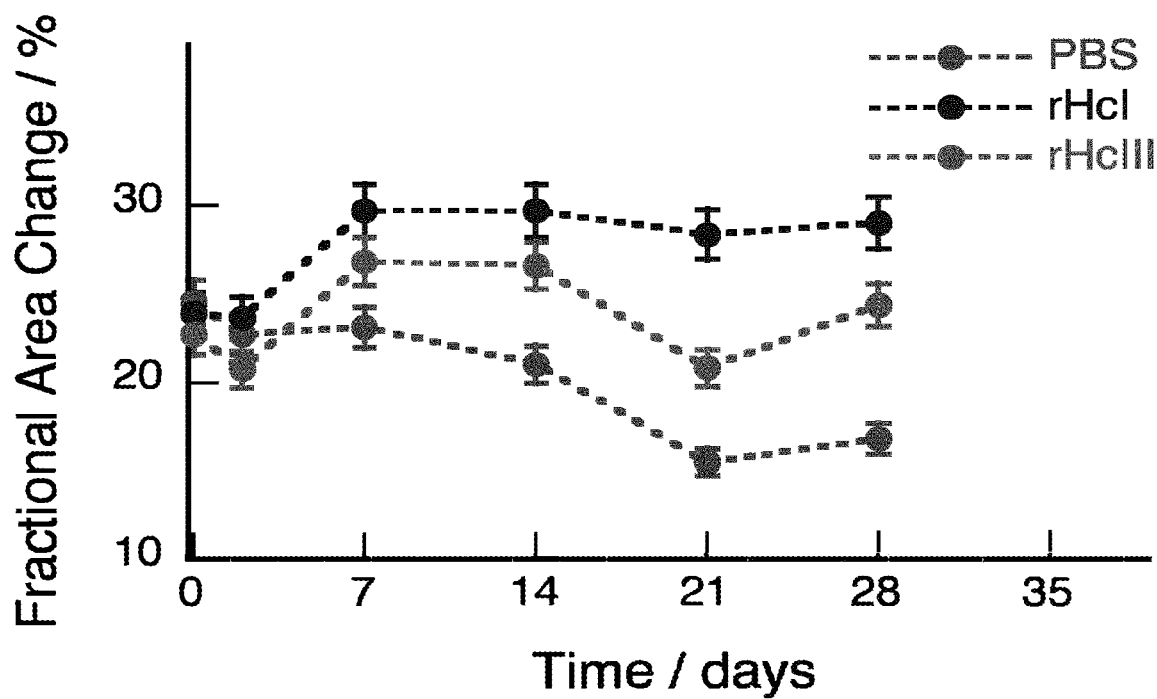
FIG. 7 shows FAC results following treatment versus PBS control.
Figure 8:
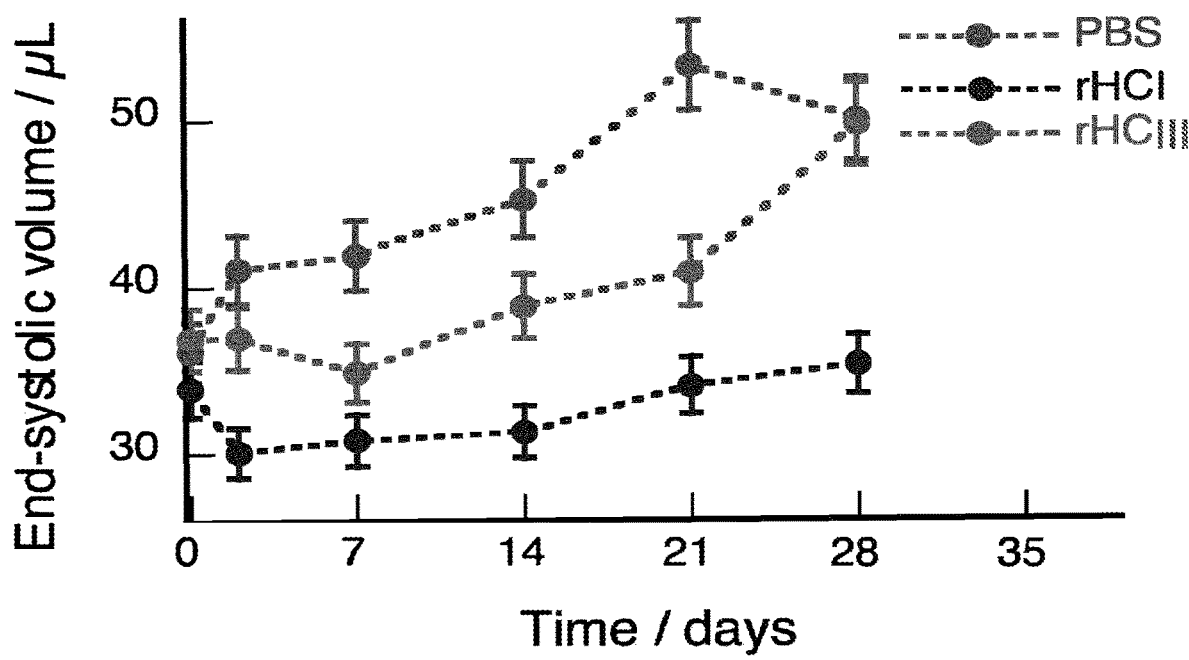
FIG. 8 shows End-systolic volume, ESV, results following treatment with rHCI or rHCIII matrices, or PBS control.
Figure 9:
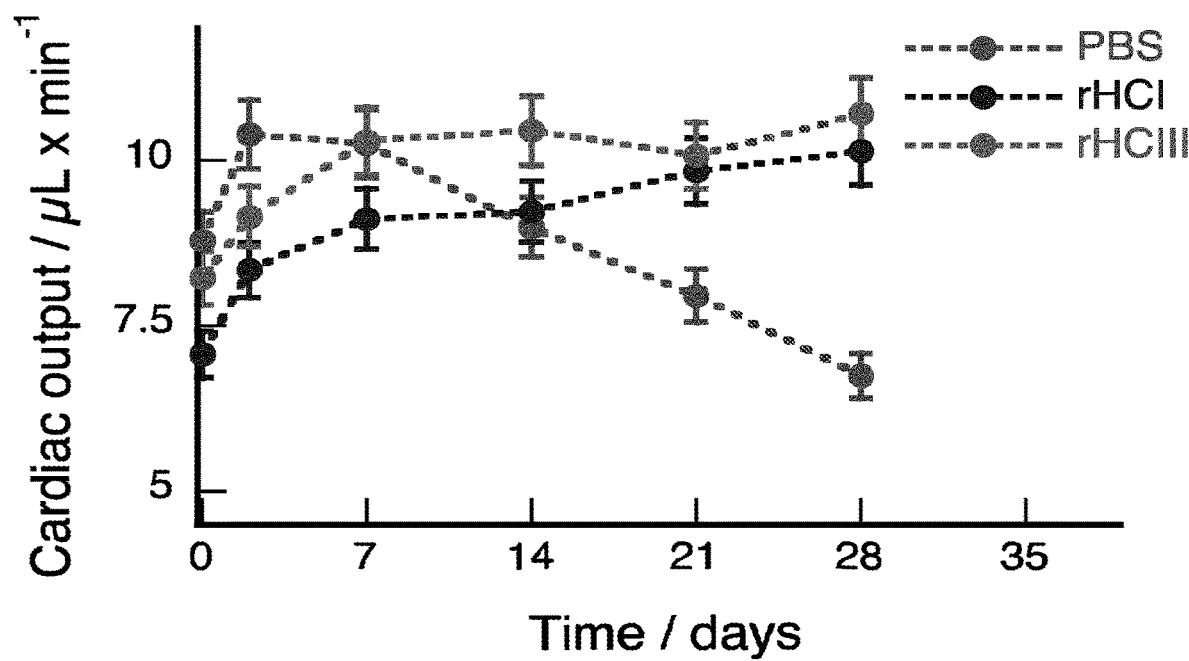
FIG. 9 shows differences in cardiac output, CO, for the PBS group versus treated groups as seen from day 14 on for rHCI and from day 21 for both collagens.

Described herein are hydrogel compositions comprising collagen and chondroitin sulfate, and uses thereof. It will be appreciated that embodiments and examples are provided for illustrative purposes intended for those skilled in the art, and are not meant to be limiting in any way.

Since the ECM dictates cell migration and neovascularization, restoring the cell-ECM interactions within the infarcted myocardium might help limit the adverse remodeling process and ultimately improve cardiac function[71, 94]. Collagen-based hydrogel matrices may represent a new avenue for the development of translatable materials for preventing cardiac remodeling, preventing infarction damage, regenerating/repairing tissue, and/or restoring tissue function, for example. Although injecting collagen in the infarcted myocardium may seem counterintuitive given the presence of the collagenous scar (fibrotic collagen) post-MI in the infarcted zone, the composition and mechanical properties of the scarred tissue are significantly different from that of the normal myocardium.[19, 71] In the present work, for what is believed to be the first time, the preparation, characterization, in vitro and pre-clinical studies of recombinant human type I and type III collagen-based biomaterials, cross-linked and including chondroitin sulfate, for applications in myocardial infarction and/or other such tissue applications is reported. As part of the studies herein, a well-established and clinically relevant mouse model of MI[103] was used to test the preclinical performance of injectable human recombinant type I and type III collagen-based hydrogel matrix therapies for treating infarcted myocardium undergoing proliferative phase (mice: 2-7 d; humans: 4-14 d).[104-106, 20]

Thus, herein, human recombinant collagen formulations and hydrogel matrices for cardiac tissue repair in the form of injectable materials have been developed. In the experimental examples below, two different formulations comprising the most abundant collagens in the heart (type I and III) were prepared and tested. Briefly, recombinant collagen matrices were developed and characterized following GMP standards to facilitate future translation. The materials had a porous structure and denaturation temperatures >47° C. Collagen matrices were then injected in 7-day old infarcted mouse hearts (n=12 per group), and heart function was monitored by echocardiography for 28 days. Mechanical properties of the hearts were measured at day 2 and day 28 post-injection. Histological analysis at day 28 included Masson's Trichrome for infarct size, α-Smooth Muscle Actin (α-SMA) for arterioles, CD31 for capillaries, and cardiac troponin for myocyte salvage. Gene expression assays using murine cardiac fibroblasts seeded onto the matrices were also carried out to determine the effect of the collagen matrices on fibroblast phenotype and activation.

In the studies described in detail herein below, for the formulation prepared using type III collagen, the cardiac function remained unchanged when compared to day 0 (p>0.1), while animals that received PBS (controls) decreased in cardiac function by about 60%. When using the collagen type I-based matrix, there was an overall improvement of the cardiac function (p<0.05), which had an onset around 7 days after the injection, with an overall improvement of the cardiac function of about 30%. These effects were accompanied by a mechanical stabilization of the heart, which was clearly seen by day 2 post-injection, and remained similar 28 days post-treatment in these experiments. Ventricular dilation and increased heart mass, which are indicative of adverse remodeling and heart failure, were observed in the PBS group, but were reduced in rHCI and rHCIII hydrogel-treated hearts. Furthermore, the size of the infarct scar at 28 days was smaller in hearts treated with hydrogel matrices, and vascular density was improved in the rHCI group (as determined by the number of α-SMA arterioles in the infarct). In vitro experiments using cardiac fibroblasts cultured on the hydrogels revealed no fibroblast-to-myofibroblast activation for either hydrogel, and increased MMP2 production for cells on the rHCI materials. It is also contemplated that, in some embodiments, hydrogel compositions described herein may modulate inflammatory response and/or promote cardiac tissue regeneration.

As described in Example 1 below, injectable collagen hydrogel matrices were prepared using recombinant collagen types I and III which prevented infarct expansion, thereby limiting loss of cardiac function for type III and I collagen treated mice. Remarkably, in these studies, type I-containing matrices delivered 7 days after infarction even improved cardiac function compared to baseline prior to treatment, and recovered part of the mechanical properties of the infarcted myocardium, which was maintained up to 28 days after treatment.

In an embodiment, there is provided herein a hydrogel composition comprising collagen or a variant or derivative thereof, and chondroitin sulfate or a variant or derivative thereof.

In certain embodiments, the hydrogel composition may be chemically cross-linked with a cross-linking agent, forming a 3D matrix comprising cross-linked collagen (or a variant or derivative thereof) molecules, and the chondroitin sulfate (or variant or derivative thereof) may in certain embodiments also be cross-linked and form part of the 3D matrix.

In certain embodiments, the hydrogel composition may include a cross-linking agent but be in a substantially uncross-linked, or partially cross-linked, form, and may be in substantially liquid or injectable form (i.e. with suitable viscosity for injection through a needle), such that the hydrogel composition is suitable for injection into heart tissue, upon which cross-linking of the hydrogel composition may proceed to form the 3D matrix. In certain embodiments, the cross-linking agent may comprise a cross-linking agent which is temperature sensitive, such that cross-linking of the hydrogel does not occur appreciably at 4° C. over a 10 minute period (for example), but does proceed at body temperature over a 10 minute period (for example). In an embodiment, the cross linker is a glutaraldehyde cross linker. In a further embodiment, the cross linker is a epoxycrosslinker. Other cross linkers and crosslinking agents also may be used as would be understood by a person of skill in the art.

In certain embodiments, the collagen or variant or derivative thereof may comprise recombinant human collagen type I (rHCI), recombinant human collagen type III (rHCIII), or a combination thereof, or a derivative or variant thereof. In certain embodiments, the collagen may comprise substantially native (i.e. undenatured, having a structure similar to that of endogenous collagen) recombinant human collagen type I (rHCI) or recombinant human collagen type III (rHCIII). Alternatively, in certain embodiments, the collagen or variant or derivative thereof may comprise any suitable type I or type III collagen, for example but not limited to porcine type I collagen, preferably medical grade collagen.

The amino acid sequences of collagen are known in the art and may be obtained from a variety of sources for example, but not limited to the National Center for Biotechnology Information Website. Without wishing to be limiting in any manner human alpha 1 chain collagen I is described under accession numbers P02461 and ACZ58371.1. Human alpha 1 chain collagen III is described under accession number P02452. Collagen sequences that are derivatives thereof or highly homologous to these sequences are also contemplated. For example, collagen sequences that exhibit 80% or more, preferably 85%, 90%, 95% or more sequence identify are contemplated herein, for example, but not limited to 80, 81, 82, 83, 84, 85, 86, 87, 88, 89, 90, 91, 92, 93, 94, 95, 96, 97, 98, 99 or 100% identity are contemplated. As will be understood, collagen variants or derivatives may include any suitable collagen or collagen mimic which adopts of native human collagen I or III, for example.

In certain embodiments, the chondroitin sulfate or a variant or derivative thereof may comprise any suitable chondroitin sulfate having a variety of different lengths, which may be sulfated to various degrees at varying positions, or any suitable variant or derivative thereof. In certain embodiments, chondroitin sulfates may also include chondroitin sulfate mimics or derivatives which functionally act as chondroitin sulfate in the hydrogels described herein. In certain embodiments, chondroitin sulfate may comprise chondroitin sulfate C (i.e. chondroitin-6-sulfate), for example. It is contemplated that chondroitin-4-sulfate might also be used in certain embodiments, for example.

In certain embodiments, the hydrogel compositions may be chemically cross-linked with a cross-linking agent, so as to form a 3D matrix. In certain embodiments, the 3D matrix may be biodegradable, biocompatible, or both. In certain embodiments, the cross-linking agent may be selected such that cross-linking of the hydrogel may be minimal or partial under conditions prior to injection (i.e. during cooling or refrigeration at 4° C., for example) during a suitable time period such as at least about 10 minutes, such that the hydrogel composition is in a substantially liquid injectable form (i.e. with suitable viscosity for injection through a needle) prior to injection. The cross-linking agent may further be selected such that following injection (i.e. under in vivo conditions at body temperature), the cross-linking agent may cross-link the hydrogel composition to form the 3D matrix in vivo. In certain embodiments, the cross-linking agent may comprise a cross-linking agent which is temperature sensitive, such that cross-linking (i.e. gelation) of the hydrogel does not occur appreciably at 4° C. over a 10 minute period (for example), but does proceed at body temperature over a 10 minute period (for example).

In certain embodiments, the mass ratio of collagen to chondroitin sulfate may be about 1:4. However, mass ratios of collagen to chondroitin sulfate may vary outside this specific range.

In certain embodiments, the chemical cross-linking agent may comprise 1-ethyl-3-(3-dimethylaminopropyl)carbodiimide (EDC)-N-hydroxysuccinimide (NHS) chemical coupling agent.

In certain embodiments, the hydrogel composition may be chemically cross-linked by EDC-NHS chemical coupling reaction at a mass ratio of collagen to chondroitin sulfate to NHS to EDC of about 1:4:0.5:0.3. Ratios of components outside that described above and herein are also possible.

In certain embodiments, the hydrogel composition may have a viscosity in the range of about 9 to 120 Pa·s at 37° C. In a first embodiment, the collagen comprises type III collagen only. In a second embodiment, the collagen comprises type I collagen only. In a further embodiment, the collagen comprises type I and type III collagen. In a preferred embodiment, the collagen is human collagen. However, in other embodiments, collagen from a different species is employed, for example, but not limited to porcine collagen.

As will be understood, in certain embodiments a denaturation temperature suitably greater than body temperature is typically desirable to maintain integrity in vivo for a suitable period of time, which may vary depending of the particular application. In certain embodiments, the hydrogel composition, once cross-linked, may have a denaturation temperature of about 40° C. or greater, about 45° C. or greater, or about 50° C. or greater, for example In certain embodiments, the hydrogel composition, once cross-linked to form a 3D matrix, may comprise a pore size of about 5 μm to about 50 μm.

In another embodiment, the hydrogel composition, once cross-linked to form a 3D matrix, may be degraded by 10

U/mL type I collagenase in PBS solution at 37° C. at a rate of about 0.2 to about 0.5 mg/s.

In another embodiment, there is provided herein a composition or formulation comprising collagen or a variant or derivative thereof, and chondroitin sulfate or a variant or derivative thereof, which is for use in combination with a cross-linking agent to provide a cross-linked hydrogel matrix. In certain embodiments, the cross-linked hydrogel matrix may be formed in vitro or in vivo.

In another embodiment, there is provided herein an injectable formation comprising collagen or a variant or derivative thereof, and chondroitin sulfate or a variant or derivative thereof. In another embodiment, the injectable formulation may further comprise a cross-linking agent to provide a cross-linked hydrogel matrix in vitro or in vivo.

In certain embodiments, there is provided herein a kit comprising any one or more of:
- collagen or a variant or derivative thereof;
- chondroitin sulfate or a variant or derivative thereof;
- a cross-linking agent;
- a syringe;
- an injection needle;
- a mixing apparatus such as, but not limited to, a T-piece mixing chamber;
- an aqueous buffer or solution, or water;
- instructions for preparing a cross-linked hydrogel matrix as described herein;
- instructions for preparing and injecting a hydrogel composition as described herein into a heart tissue;
- or any combination thereof.

In another embodiment, there is provided herein a biocompatible and/or biodegradable hydrogel composition comprising native collagen and chondroitin sulfate, the collagen and chondroitin sulfate being at least partially chemically cross-linked thereby forming a matrix. In certain embodiments, the native collagen may be recombinant human collagen type I (rHCI), recombinant human collagen type III (rHCIII), or a combination thereof.

Native collagen encompasses any suitable collagen which is substantially undenatured, and which structurally and chemically mimics natural endogenous collagen of a subject. Native collagen is not collagen which has been irreversibly hydrolyzed, as in the case of gelatins. Examples of suitable native collagens may include those which are commercially available in undenatured form from Fibrogen. Native collagen may, in certain embodiments, include native recombinant collagen which, being recombinantly produced, does not need to be animal-derived, and therefore may, in certain embodiments, feature reduced immune reaction potential and/or avoid risk of pathogen transfer from animal sources. Nevertheless, it is also contemplated herein that medical grade animal collages may be used in certain embodiments. Also contemplated are collagen variants or derivatives having about 75%, 80%, 85%, 90%, or 95% sequence identity with native collagen.

The person of skill in the art having regard to the teachings herein will be able to select a suitable native collagen for a particular application. By way of example, in certain non-limiting embodiments, a native recombinant human collagen may be selected for applications in human subjects so as to facilitate biocompatibility and/or reduce risk of pathogen transfer, where desired. In certain embodiments, native collagen may include other suitable collagen sources, such as other medical grade collagen. In certain embodiments, native collagen may include collagen protein solutions which have not been exposed to a denaturing condition such as, by way of non-limiting example, extreme pH and/or temperatures greater than, for example, about 20° C. following production thereof.

Chondroitin sulfates are generally considered as sulfated glucosaminoglycans (GAGs). Suitable chondroitin sulfates may include those having a variety of different lengths, and may be sulfated to various degrees at varying positions. In certain embodiments, chondroitin sulfates may also include chondroitin sulfate mimics or derivatives which functionally act as chondroitin sulfate in the hydrogels described herein. In certain embodiments, chondroitin sulfate may comprise chondroitin sulfate C (i.e. chondroitin-6-sulfate), for example. It is contemplated that chondroitin-4-sulfate might also be used in certain embodiments, for example.

As will be understood, biocompatible hydrogels may include any suitable hydrogel or other matrix which is substantially tolerated in vivo without triggering significant immune response and/or tissue damage. Biodegradable hydrogels may include any suitable hydrogel or other matrix which may be degraded over time in vivo through natural processes which may involve enzymatic degradation.

Hydrogels may be generally considered as hydrophilic polymer chain networks which are highly water absorbent. Hydrogel compositions described herein may include water-rich/water-absorbent networks of collagen and chondroitin sulfate polymer chains, and the collagen and chondroitin sulfate may be chemically cross-linked, thereby forming a matrix. Such hydrogel matrices may have a high water content (for example, in certain embodiments, >90%), and may be suitable for supporting cell viability and function, and/or tissue maintenance, repair, or regeneration.

In certain embodiments, hydrogel compositions provided herein may include those in which the native collagen and the chondroitin sulfate components are chemically cross-linked using any suitable chemical cross-linker known to the person of skill in the art having regard to the teachings herein. In certain embodiments, the native collagen and the chondroitin sulfate components may be chemically cross-linked using 1-ethyl-3-(3-dimethylaminopropyl)carbodiimide (EDC)-N-hydroxysuccinimide (NHS) chemical coupling reaction. It is contemplated that other chemical cross-linking reactions may be used, for example in certain embodiments it is contemplated that glutaraldehyde may be used for cross-linking.

For example, native collagen and the chondroitin sulfate compositions as described herein may include those which are chemically cross-linked by EDC-NHS chemical coupling reaction, using a mass ratio of native collagen to chondroitin sulfate to NHS to EDC of about 1:4:0.5:0.3. Other ratios are also possible.

In certain embodiments of the hydrogel compositions described herein, the mass ratio of native collagen to chondroitin sulfate may be about 1:4, for example. In certain further embodiments, hydrogel compositions described herein may feature a denaturation temperature which is greater than the body temperature of a subject. For example, the hydrogel compositions may feature a denaturation temperature greater than about 45° C., or greater than about 47° C., in certain embodiments as measured using the methods described in Example 1 hereinbelow. In certain embodiments, hydrogel compositions may include those which substantially solidify at 37° C. in less than about 10 minutes.

In still further embodiments, the hydrogel compositions described herein may feature a viscosity after cross linking of about 9 to about 150 Pa·s at 37° C., such as about 15 to about 120 Pa·s at 37° C.s measured using the methods described in Example 1 herein below. In certain embodiments, hydrogel compositions as described herein may include those having suitable properties for injection using, for example, a 27-gauge needle.

As will be understood, hydrogel compositions described herein may typically be prepared in a mixing system for injection to a subject in need thereof via syringe or other such administration route. Where administration is via syringe injection, the hydrogel composition prepared in the mixing system may be configured to have a suitable viscosity so as to facilitate substantially homogenous or even flow through the syringe. By way of example, viscosity of lower than about 0.10 Pa*s, or lower than about 0.05 Pa*s, may facilitate syringe injection. Where delivery via syringe injection is desired, for example, cross-linking of the hydrogel composition may be initiated or pre-configured in the mixing system, and injection via the syringe may be performed while the hydrogel composition is in substantially liquid form having a suitable viscosity. Following injection, the cross-linking may progress, with the hydrogel composition solidifying or gelling after administration. By way of example, the mixing system may be maintained at low temperature (i.e. on ice) before injection so as to limit cross-linking/solidification, and upon injection into a subject the increased temperature in vivo may accelerate cross-linking/solidification of the hydrogel, thereby forming a hydrogel matrix in vivo.

In certain embodiments, hydrogel compositions described herein may adopt a 3D porous structure, wherein the hydrogel matrix may feature a pore size range of about 5 to about 50 μm, such as about 10 to about 25 μm in average number, for example following cross-linking.

As will be understood, hydrogel compositions described herein may include those which are biodegradable by endogenous enzymes. For example, hydrogel compositions may include those which may be degraded by 10 U/mL type I collagenase in PBS solution at 37° C. at a rate of about 0.1 to about 2 mg/s, such as about 0.15 to about 0.65 mg/s in certain embodiments. See, for example, FIG. 1.

In a non-limiting example of a suitable hydrogel composition as described herein, the native collagen may be recombinant human rHCI, the rHCI and the chondroitin sulfate may be chemically cross-linked by EDC-NHS chemical coupling reaction at a mass ratio of rHCI to chondroitin sulfate to NHS to EDC of about 1:4:0.5:0.3, and the hydrogel composition may have a denaturation temperature of about 46° C., a pore size of about 11 μm, and may be degraded by 10 U/mL type I collagenase in PBS solution at 37° C. at a rate of about 0.5 mg/s, for example.

In another non-limiting example of a suitable hydrogel composition as described herein, the native collagen may be recombinant human rHCIII, the rHCIII and the chondroitin sulfate may be chemically cross-linked by EDC-NHS chemical coupling reaction at a mass ratio of rHCIII to chondroitin sulfate to NHS to EDC of about 1:4:0.5:0.3, and the hydrogel composition may have a denaturation temperature of about 50° C., a pore size of about 24 μm, and may be degraded by 10 U/mL type I collagenase in PBS solution at 37° C. at a rate of about 0.2 mg/s, for example.

In certain embodiments of the hydrogel compositions described herein, the native recombinant human collagen may comprise a combination of rHCI and rHCIII.

Hydrogel compositions described herein may, in certain embodiments, additionally include one or more pharmaceutically acceptable carriers, diluents, or excipients.

As will be understood, it is contemplated herein that hydrogel compositions provided herein may be for use in regeneration or repair of tissue, improvement of tissue function, mechanical stabilization of tissue, prevention of tissue damage, or prevention of tissue loss of function. In particular, the tissue may be cardiac tissue, and the hydrogel composition may be for injection to the heart following a myocardial infarction event, for example. In certain embodiments, hydrogel compositions described herein may be for improving vascularity in infarcted heart muscle, or other tissue that may suffer from ischemia such as, by way of non-limiting example, skeletal muscle, neural tissue, renal tissue, bone and cartilage, gastrointestinal tissue, and/or skin.

As will be recognized, hydrogel compositions provided herein may be for administration to the heart by one or multiple injections at a single time-point, or by one or multiple injections at a plurality of time-points following a myocardial infarction event.

Further, in certain embodiments, hydrogel compositions as described herein may be for administration simultaneously, sequentially, or in combination with other known myocardial infarction therapeutics such as, but not limited to, percutaneous coronary intervention, therapeutic angiogenesis, the use of targeted peptide(s), protein(s), or drug delivery, or cell-based therapy. In certain embodiments, such additional myocardial infarction therapeutics may be incorporated into the hydrogel compositions described herein. In additional embodiments, hydrogel compositions described herein may be for use in the treatment of heart failure, or as a management measure aimed at preventing further functional loss or at improving cardiac function, for example.

In certain embodiments, it is contemplated that hydrogel compositions provided herein may be for use in preventing loss of cardiac mechanical properties, preventing cardiac remodeling, reducing fibrosis and/or infarct area, improving vascularity of infarcted heart muscle, and/or improving cardiac function following the myocardial infarction event.

In another embodiment, there is provided herein a method for treating a myocardial infarction event in a subject in need thereof, said method comprising:
  providing a hydrogel composition as defined herein; and
  injecting said hydrogel composition into affected heart tissue of the subject following the myocardial infarction event.

As will be understood, and as previously described hereinabove, cross-linking of the hydrogel composition may, in certain embodiments, occur at least in part in vivo following injection to the subject.

In certain embodiments, the hydrogel compositions may, preferably, be administered shortly following the myocardial infarction event to limit the amount of acute damage, and may be administered directly to the heart muscle via injection. Hydrogel compositions described herein may be prepared and used directly following preparation in certain embodiments, or may be stored temporarily before use.

As discussed in further detail herein, hydrogel compositions described herein were injected into a semi-mature myocardial scar (termed the proliferative phase), which is a relevant pre-clinical model for patients who do not receive immediate revascularization therapy following an infarction event, or those who do not respond appropriately to current standard treatments, and are at greater risk for advanced heart failure. Results suggest that the injectable collagen-based material may, in certain examples, improve myocardial function even when delivered during the proliferative phase, showing an effect beyond preserving function.

Also provided herein are methods for preparing hydrogel compositions as described herein, said methods comprising:
  providing a solution of native collagen;
  providing a solution of chondroitin sulfate;

providing an EDC and NHS solution, or other suitable crosslinking agent;

mixing the solution of undenatured collagen with the solution of chondroitin sulfate, thereby forming a first mixed solution; and mixing the first mixed solution with the EDC and NHS solution (or other suitable crosslinking agent), thereby initiating cross-linking of the native collagen and chondroitin sulfate to form a matrix hydrogel composition in vitro or in vivo.

As will be understood, other preparation method steps, orders of steps, orders of mixing, and/or other method modifications known to the person of skill in the art having regard to the teachings herein may be performed to suit particular applications as needed.

As will be understood, and as previously described hereinabove, cross-linking of the hydrogel composition may, in certain embodiments, occur at least in part in vivo following injection to the subject.

In certain embodiments, the mixing steps may be performed using syringes and a connected enclosed mixing system so as to maintain the hydrogel composition under controlled and aseptic conditions. Examples of such mixing systems are described in the materials and methods section of Example 1 hereinbelow, and depicted in FIGS. 10 and 11.

In certain embodiments of the preparation methods described herein, a mass ratio of native collagen to chondroitin sulfate to NHS to EDC in the chemical cross-linking mixing step may be about 1:4:0.5:0.3.

In further embodiments of the preparation methods described herein, the solution of native collagen may comprise about a 1% w/v solution. In further embodiments, the solution of chondroitin sulfate may comprise about a 40% chondroitin sulfate solution.

By way of example, in certain embodiments of the preparation methods described herein, the EDC and NHS solution may be prepared by mixing an about 5% w/v NHS solution and an about 3% w/v EDC solution in a 1:1 ratio.

As well, in certain embodiments of the preparation methods described herein, the methods may further comprise a step of adding an NaOH solution to the hydrogel composition so as to adjust the pH of the hydrogel composition to a physiologically acceptable level, such as a pH level at or near that of the cardiac tissue to be treated.

As will be understood, the presently described hydrogel compositions, and methods for the preparation thereof, may be amenable to GMP standards and/or other such pharmaceutical industry standards. Standard operating procedures (SOPs) may be developed for producing and using the hydrogel compositions described herein, examples of which are provided in Example 2 below.

These and other features of the present invention will be further understood with reference to the following Examples.

Example 1

Preparation, Characterization, and In Vitro and In Vivo Testing of Injectable Recombinant Human Collagen Matrices Examples of biocompatible and biodegradable hydrogel compositions, as well as the preparation, characterization, and in vitro and in vivo testing of these injectable matrices, are described in further detail below with reference to FIGS. 1-10 and 13-15. Experimental methods and protocols used for these studies are also provided herein below.

As part of the following studies, injectable recombinant human type I (rHCI) and III (rHCIII) collagen hydrogel matrices were prepared and studied for treating established infarcted myocardium in a clinically relevant murine model. For mice treated with rHCIII-based hydrogel matrices, cardiac function increased by a 15% when compared to baseline; while animals that received saline buffer exhibited a 60% decrease in cardiac function. The rHCI-based hydrogel matrix group showed a ≈30% improvement in cardiac function. These effects were accompanied by restoration of the mechanical properties of the cardiac muscle two days post-injection. Noticeably, both collagen formulations prevented adverse cardiac remodeling, and for rHCI-based hydrogel matrix there was an increase in the remote wall thickness 28 days post-treatment. While no differences in arterioles and number of myoblasts were detected, the rHCI-based hydrogel matrix treated animals showed larger number of capillaries and cardiomyocytes in the border zone, and M2 macrophages within the ischemic zone. In vivo assessment of myocardial infarction using a Cxcr3-EGFP mouse indicated an increase in the number of GFP+ cells in the left ventricle two days post treatment for rHCI. Further, in vitro experiments indicated no differences in monocyte adhesion while there was a better macrophage migration for rHCIII-based hydrogel matrices; and both matrices induced macrophage polarization into M2 phenotype and MMMP1 activation. Interestingly, pre-activated cardiac fibroblasts in vitro cultured with macrophage media of cells incubated on rHCI-based hydrogel matrices decreased the α-SMA production. Without wishing to be bound by theory, it is hypothesized that the unprecedented functional recovery with rHCI-based hydrogel matrixes incorporates promoting pro-healing M2 macrophages, rescuing of cardiomyocytes, and reducing activated cardiac fibroblast population, which may limit pathological remodeling of the myocardium.

Synthesis and Characterization of Human Recombinant Collagen Matrices

Regenerative approaches for promoting cell engraftment and functional tissue regeneration has motivated the development of artificial scaffolds; the present inventors have now identified that mimicking the ECM using naturally occurring human biopolymers, prepared using recombinant techniques, found in the heart may provide benefit, for example in relation to translational purposes. In these studies, in what is believed to be for the first time, human recombinant collagen-based cross-linked hydrogel matrices (1.0% w/w) containing the pro-angiogenic chondroitin sulfate C have been developed and studied for cardiac tissue repair and/or prevention of cardiac tissue damage, see FIG. 1A.

The collagen-based formulations used in the following studies were developed as thermo-responsive matrices to secure their intra-myocardial retention within the infarct. In designing the materials, the following properties were targeted: (1) gelation times of about 10 min, to facilitate effective injection of the matrices in a substantially liquid form, and (2) use of about the same total concentration of crosslinker to minimize variability between rHCI and rHCIII-based hydrogel scaffolds. Thus, a series of itineration steps using variable concentration of the crosslinker agents NHS and EDC were carried out using 1.0% w/w protein type of collagen solutions, as described in the experimental section.

The hydrogel matrices used prepared in these studies contained the aminoglycoside chondroitin sulfate C, see FIG. 1A. In some ways these matrices resemble the protein agrin used for cardiac tissue repair;[107] however, instead of direct injection of a non-crosslinked protein, the present studies employ in situ 3D assembling of the collagen-based matrix used to provide a biomimetic niche for promoting endogenous repair within the infarcted myocardium. As described in detail below, protocols for manufacturing the matrices were standardized to minimize or reduce batch-to-batch variability.

The hydrogel matrices of these studies were prepared using a standardized protocol, using comparable amounts of chemical reagents for both rHCI and rHCIII-based scaffolds, and produced scaffolds with reproducible physical and biological properties. The hydrogels prepared in these studies thermally solidify (37° C., ≤10 min), resulting in crosslinked 3D structures with denaturation temperatures of >45° C., see FIG. 1B, with no significant differences between the rHCI and rHCIII-based hydrogels (p>0.5; t-test). Similar water contents were measured for both hydrogels 94%. The 3D-matrices prepared using rHCI in these studies were considerable more susceptible to collagenase degradation (0.59±0.08 vs. 0.15±0.03 mg/min for type I and III, respectively, p=0.0048; t-test) and had a lower viscosity than their rHCIII-based counterparts (36±21 vs. 104±32 Pa·s for type I and III, p=0.0014; t-test, respectively). Viscosity values for both formulations, and in particular rHCI, were considerably higher than that of rat-tail collagen hydrogels (21±5.4 Pa·s), which had been previously used by our team as injectable therapy with only limited benefits in cardiac tissue repair for semi-mature scars.[86, 87, 88] The porous structure of the present hydrogels was considered to be relevant for stimulating cell migration (cell infiltration) and engrafting. The present matrices presented a porous structure, with average pore sizes of 11±0.4 and 24±1.0 μm measured for rHCI-based and rHCIII-based hydrogels, respectively, FIG. 1C. Such differences in pore sizes were in line with the greater viscosity values measured for the rHCIII-based matrices. Furthermore, pore size values were similar to that measured for our type I rat-tail collagen matrices, which were 11±0.5 μm μm, see FIG. 5.

In summary, the cumulative data for the physical properties of the collagen-based materials prepared and described in these studies, including the identified higher-than-body-temperature denaturation temperature, degradability by enzymes (i.e. collagenase), intrinsic viscosity, comparable if not higher viscosity to/than other collagen matrices, and/or porous structure properties of the present scaffolds, identified these materials as interesting candidates, and further assessment of their biological performance in myocardial infarction models was performed as described below.

In Vivo Assessment of Regenerative Properties of the Recombinant Collagen-Based Matrices.

Since the ECM plays a role in regulating cell migration and neovascularization,[89, 90, 91, 92] restoring the cell-ECM interactions may promote endogenous tissue repair, limit the adverse remodeling process, and/or improve cardiac function.[93,94] Seminal work in infarcted hearts described a structural remodeling predominantly in the left ventricle that correlates with function deterioration to end-stage heart failure,[95] which directly links with patient prognosis and survival.[96] The severity of ventricular remodeling post-MI is proportional to the size of the infarct region.[97] Thus, therapies that aim to prevent or reduce cardiac remodeling by surgically restoring blood flow to the ischemic myocardium have become the cornerstone for many years.[95] However, on average, 10% of patients, particularly those with large infarcted areas, will evolve to advance heart failure,[98] which has a five-year mortality of ≈55%.[98] As a consequence, the majority of HF patients are considered end stage, where heart transplants and heart assist devices, both expensive and requiring invasive open chest surgeries, are the ultimate and only solution for their condition.

In vivo experiments herein were designed to assess the suitability of the hydrogel compositions described herein to improve, or preserve, the cardiac function in an established scar by directly targeting infarct wall thinning in 7 days post-MI hearts, see FIG. 2a, in a clinically relevant mouse model,[75,76] with large infarcted areas.[77] Interestingly, just 2 days post-treatment using the present compositions produced a recovery of the mechanical properties of the infarcted heart post-injection (p<0.001), see FIG. 2b. This reestablishment in mechanical performance was preserved for the rHCI-based composition 28 days post-injection when compared to day 2 (p>0.1). For hearts treated with rHCIII-based composition, there was a decrease in the Young's Moduli (p<0.01), however, those remained superior to the PBS control group, FIG. 2b. Cardiac remodeling leads to enlarged hearts; this occurs in advanced stages post-MI. Animals that received only PBS injections had enlarged hearts as seen in FIG. 2c, left. Normalized heart weights plotted for the different groups showed that the PBS group had the larger hearts amongst the groups, FIG. 2c, right (PBS/rHCI ratio=1.40±0.11, PBS/rHCIII ratio=1.20±0.07; p<0.05). Animals that received rHCI-based matrices had similar sizes and weights compared to non-infarcted mice (p>0.1). For the group that received rHCIII-based composition, weights were statistically larger than rHCI-based group, but smaller than the PBS group, FIG. 2c, right. Further, injections of pure, non-crosslinked, rHCI and rHCIII proteins post-MI did not prevent enlargement of the hearts 28 days post-injection when compared to the PBS group (PBS/rHCI ratio=0.98±0.05, PBS/rHCIII ratio=1.08±0.05, p>0.5).

These findings illustrate that the therapeutic/regenerative/reparative properties of the present materials do not solely rely on the presence of the collagens alone. In summary, these results indicate that the present matrices may be capable of preventing or reducing cardiac remodeling, which suggests the suitability of such matrices as therapeutic options for heart failure.

Echocardiography was performed after intramyocardial injections (10 μl each site, 50 μl total),[59, 78, 79, 80] of PBS (control), rHCI-based or rHCII-based hydrogel matrices described herein. Additional experiments were carried out for MI and injections, where animals were euthanized only 2 days after injection and hearts harvested for measuring mechanical properties of the left ventricle. Further, another two groups of animals received pure, non-crosslinked, collagen injections; rHCI or rHCIII, and were used to compare the effectiveness of the present matrices vs. the pure collagens for up to 4 weeks after injection.

After injection, left ventricle ejection fraction, LVEF, improved ≈27% by day 7 for rHCI-based treatment (p<0.05 vs. PBS), while for rHCIII-based treatment, it remained practically unchanged when compared to baseline, prior to injection (p>0.5), FIG. 3a. This contrasts with the group of animals that received PBS only, which declined in their cardiac function over the 28 days as seen in FIG. 3a. When comparing the LVEF 28 days post-injection, see FIG. 6, one can see how the injection of the pure (non-cross-linked) collagens did not produce the effects that were seen when using the hydrogel matrices, which indicates, once again, that collagen alone is not responsible for the regenerative/reparative and preventative properties of the presently prepared collagen scaffolds.

Fractional area change, FAC, also improved by about 25% for rHCI-based hydrogel group (at >day 14, p=0.058, 21 days onwards p<0.001 vs. PBS, see FIG. 7), while for rHCIII-based group it remained practically unchanged when compared to the baseline (p>0.5) 28 days post-MI, see FIG. 3b. End-systolic volume, ESV, remained relatively unchanged for rHCI-based group at day 28 (p>0.5), while for rHCIII-based group and PBS group there was an increase of ESV of ≈30% in both cases (p<0.05 vs. baseline, p=0.96 for rHCIII-based vs. PBS), see FIG. 8.

Stroke volume, SV, improved by a ≈35% for rHCI-based and rHCIII-based matrices (day 28, p<0.05 vs. baseline), while for the PBS group it decreased by 16%, 28 days post-injection (p<0.05 vs. baseline), FIG. 3c. Finally, cardiac output, CO, increased by a factor 1.30-1.40 for both rHCI-based and rHCIII-based matrices (day 28, p<0.05 vs. PBS, FIG. 3d). Differences with the PBS group were seen from day 14 on for rHCI-based group (p=0.054), and from day 21 for both collagens (p<0.05, see FIG. 9). PBS group decreased by 23% after 28 days (p<0.05 vs. baseline). These results indicate the efficacy of the present materials under the tested conditions for improving and/or preventing worsening of cardiac function for rHCI-based and rHCIII-based hydrogel treatments, respectively. These results are in line with the observed reduction in the infarct size, where the group that received rHCI-based hydrogel treatment showed a reduction of 60% in infarct size, while for rHCIII-based group infarcts were ≈30% smaller than the PBS group, see FIG. 3e.

Despite numerous materials which have been developed for cardiac tissue repairing post-MI, to our knowledge the use of human recombinant collagen materials as described herein have not been reported for cardiac tissue engineering in the form of injectable therapeutics. Further, our team has recently reported that animal-origin collagens are capable of restoring cardiac function only if injected 3 h post-MI in mice models.[80] Thus, the capacity of the present materials, particularly rHCI-based matrices, may represent an interesting avenue for clinical translation in hearts that have past the initial inflammatory phase post-MI.[99]

Without wishing to be bound by theory, in order to provide further insights on the underlying mechanisms observed for the different matrices, rHCI-based and rHCIII-based, immune-staining experiments were carried out for vascular density of the different groups at day 28, see FIG. 4a-b. A two-fold increase in the number of arterioles was seen for the rHCI-based hydrogel group. Similar to the results observed previously for other collagen matrices,[80] no changes in the number of capillaries within the infarct region, were observed (not shown). Thus, the increase in the number of arterioles, and consequently in blood perfusion, were in line with the improvement of the cardiac function for the group that received rHCI-based hydrogel. While for the rHCIII-based hydrogel a more mechanically related stabilization of the heart post-MI, rather than a regenerative effect, may remain as a more predominant effect.

Thus, the in-vitro effect of isolated mouse cardiac fibroblasts seeded onto 300 μm layers of the matrices, rHCI-based or rHCIII-based, and cultured for 5 days, was next assessed (see FIG. 4c). The results shown no α-SMA activation for both matrices (compared to control fibroblasts cultured on tissue culture polystyrene). There was an increase in type I collagen production for cells seeded onto the rHCIII-based matrices compared to those on the rHCI material. An increase in the MMP2 levels was seen for the rHCI-based matrix, when compared to the rHCIII-based group. These in vitro differences in cell response to the present matrices may be extrapolated to our experimental evidence for the in vivo data, where the increase in MMP2 levels for the rHCI-based hydrogel may be related to a more efficient cardiac remodeling and cell angiogenesis.

In vitro studies indicate that neither of the hydrogel compositions tested promoted differentiation of cardiac fibroblasts into myofibroblasts (i.e. the cells responsible for deposition of the dense scar tissue after myocardial infarction).

A clinically relevant mouse model was used, and the post-injection effects of the collagen-based formulations were assessed. The primary end-point of this study was cardiac function after 28 days of treatment. In assessing cardiac function after 28 days of treatment, echocardiography was performed before (baseline), and after intra-myocardial injections within the infarcted myocardium (10 μl each site, 50 μl total) of rHCI, or rHCIII matrices as well as for PBS (control), see FIG. 16A. Consistent with previous studies, left ventricular ejection fractions (LVEF) decreased to ≈30% from baseline for hearts treated with PBS 28 days post-injection, FIG. 16B. Compared to PBS, function in the recombinant human collagen treated groups became significantly better ≈15% for rHCIII (p=0.00013 vs. PBS) and 30% for rHCI (p<0.0001 vs. PBS), see FIG. 16B. However, increment in cardiac function for rHCIII was borderline when compared to baseline (p=0.044), while rHCI was significantly better than baseline (p<0.0001), see FIG. 15. The increment in LVEF shown in FIG. 16B and FIG. 15 was not seen upon injection of pure collagens, which indicates that collagens alone (see FIG. 6) were insufficient, and rather the assembled collagen 3D structure of the hydrogel matrices described herein were responsible for the effects observed after injection.

End-systolic volume, ESV, remained unchanged for rHCI at day 28 vs. baseline (FIG. 16C), while for PBS there was an increment of the volume of ≈30% (p<0.0001 vs. baseline). rHCIII' ESV did not reach statistical difference from PBS (p=0.0877). Fractional area change, FAC, improved by a 25% for rHCI (p<0.0001 vs. PBS, see FIG. 16D); while for rHCIII remained almost unchanged (p=0.045 vs. PBS, and p<0.0001 vs. rHCI) at day 28 post-treatment, see FIG. 16D. Stroke volume, SV, improved by a ≈45% for rHCI and rHCIII matrices (day 28, p<0.05 vs. PBS, see FIG. 16E). Finally, cardiac output, CO, increased by a ≈45% for both rHCI and rHCIII matrices (day 28, p<0.05 vs. PBS, see FIG. 16F).

Figure 16:
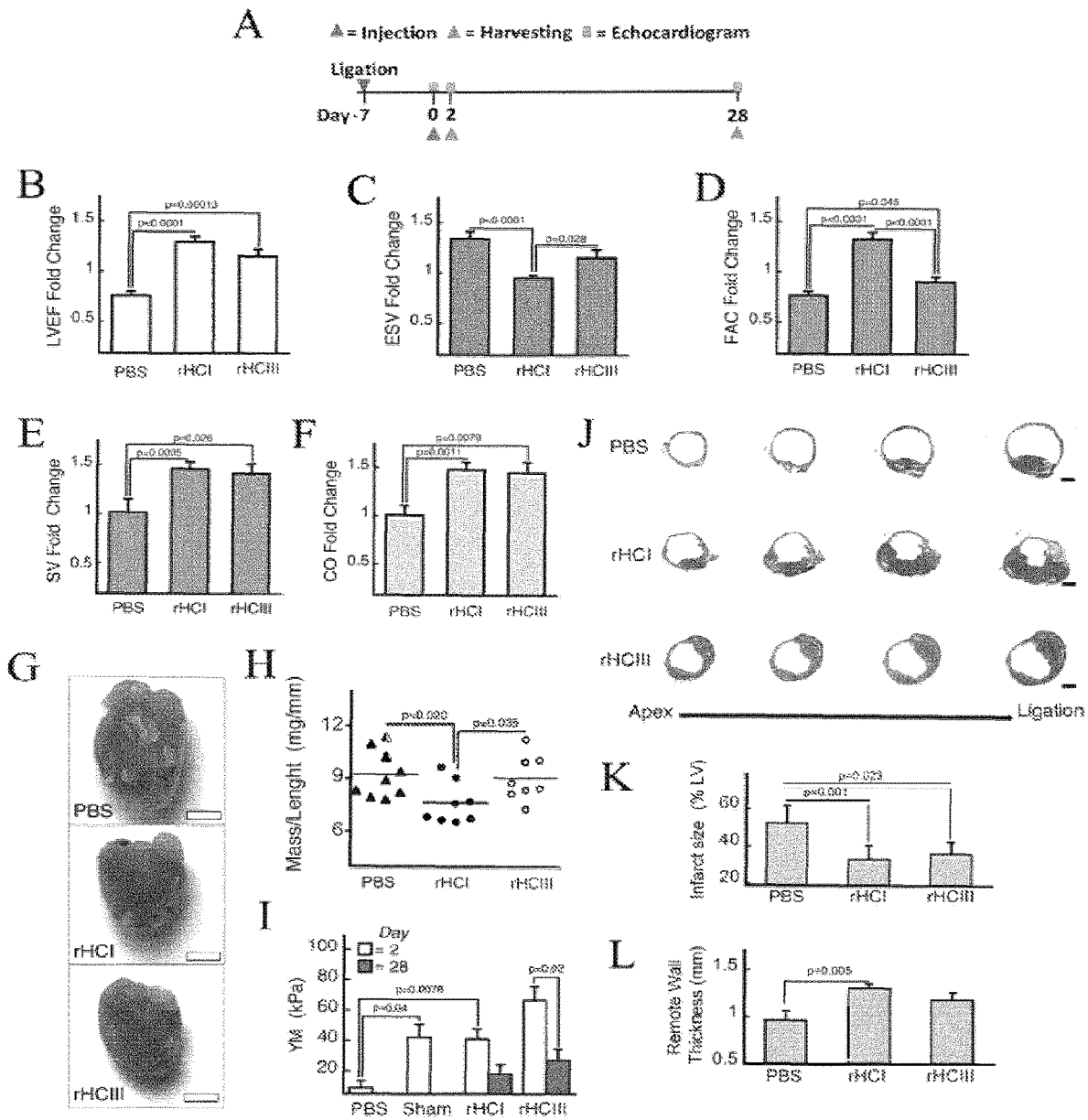
FIG. 16: Injection of recombinant human collagen-based hydrogel matrices (including chondroitin sulfate) to study positive effects in cardiac function, preventing adverse remodeling, and restoring mechanical properties. (A) provides an example schematic for the in vivo experimental setup for the MI mouse; (B)-(F) show changes in left ventricle ejection fraction (LVEF), end systolic value (ESV), functional area change (FAC), stroke volume (SV), and cardiac output (CO) 28 days post-injection calculated as fold changes vs. their respective baseline values. LVEF (B), end systolic value (ESV) (C), fractional area change (FAC) (D), stroke volume (SV) (E), and cardiac output (CO) (F) 28 days post-injection are shown. Sample sizes for data shown in B-F were n=11 for PBS, n=15 for rHCI, and n=14 for rHCIII.

Cardiac remodeling leads to enlarged hearts, which occurs in advanced stages post-MI. Animals that received only PBS injections had enlarged hearts as shown in FIG. 16G. Heart weights plotted for the different groups showed that only the hearts treated with rHCI matrices were statically smaller than PBS (p=0.02) or those treated with rHCIII (p=0.035), see FIG. 16H. Interestingly, just two days post-treatment the tested materials produced a recovery of the mechanical properties of the infarcted heart post-injection (p=0.0078 rHCI vs. PBS), see FIG. 16I. This reestablishment in mechanical performance was preserved only for the rHCI matrices 28 days post-injection when compared to day 2 (p>0.1). For hearts treated with rHCIII, there was a decrease in the Young's Moduli (p=0.02) 28 days post-injection. Measuring the mechanical properties of 28 days old infarcted hearts treated with PBS was not possible due to the infarct size and cardiac wall thinning. Thus, data for 28 days are not shown for the PBS group. However, comparison with the sham group provided a benchmark comparison landscape. Masson's trichrome histological analyses 28 days post-treatment was performed. FIG. 16J shows that by way of a multiple regression analysis to account for baseline LVEF, infarct size for rHCI (32.90±7.54%, p=0.001) and rHCIII (35.96%±6.38%, p=0.023) hydrogel matrix treated groups was smaller than that for the PBS control group (52.36±9.40%) but not significantly different from each other (p=0.188). Also, for rHCI treated hearts there was an increase in remote wall thickness (1.30±0.05, p=0.005 vs. PBS), see FIG. 16K, as compared to PBS mouse hearts (0.96±0.10 mm) while there was only a trend in increasing thickness for rHCIII remote cardiac wall thickness (1.18±0.08 mm, p=0.07 vs. PBS).

These results, describing the preparation and in vitro and in vivo experimental testing of rHCI-based and rHCIII-based hydrogel matrices, support the use of such matrices in the treatment and/or prevention of myocardial infarction in cardiac tissue. In terms of comparisons, rHCI-based matrices demonstrated better improvement of cardiac function than rHCIII-based matrices under the conditions tested. Furthermore, experimental results indicate benefits from treatment with the present matrices which rival rat-tail matrices injected in the inflammatory phase post-infarction, while the matrices herein developed were effective at later stages post-MI. Hence, results suggest that the present hydrogel matrices may be advantageous in that they may provide an effect when administered at various time-points after infarction in certain embodiments. Although not wishing to be bound by theory, experimental results suggest that rHCI-based matrices may act via a more reparative/regenerative pathway, while rHCIII-based matrices may act via a more mechanical stabilization-type pathway.

Assessment on Revascularization, Macrophage Infiltration, Post-Inflammatory Response of the Recombinant Collagen-Based Matrices To provide further insight into the underlying mechanisms observed for the different matrices, rHCI and rHCIII, immunohistochemical analysis was carried out for the vascular density of the various groups at day 28, see FIG. 13A. Interestingly, the rHC hydrogel treatments did not affect vascular density or myofibroblast density as compared to the control group at 28 days post-injection within the infarcted tissue, see FIG. 13A'. Interestingly, the number of capillaries in the border-zone was larger for the rHCI and rHCIII groups as shown in FIG. 13A". In addition, the number CD206, M2 macrophages detected within the infarcted region for rHCI was statistically larger (≈1.5 times) than for the PBS group (p=0.048), see Figure B. This difference was not observed in the borderzone and/or remote areas within the heart for the treatment groups when compared to PBS, see FIG. 13B'.

In vivo cell infiltration was assessed upon 2 days of injection of the collagen-based matrices using Cxcr3-EGFP animals, whose mononuclear bone marrow cells are expressing GFP protein. Results show that the number of positive monocyte cells recruited from the marrow was significantly lower for the rHCI group than for the rHCIII and PBS groups, see FIG. 13C1. Similar behavior was observed for double positive staining experiments for F4/80 (FIG. 13C2), CD38 (FIG. 13C3), and CD11b markers (FIG. 13C4) (p<0.05 vs. PBS). Troponin positive cells were stained, see FIG. 13D. The number of troponin positive cells in the border zone was statistically higher in number only for the rHCI group vs. PBS and/or rHCIII, see FIG. 13D'.

In Vitro Biological Performance of Recombinant Collagen-Based Matrices for Cardiac and Immune Cells The in vitro ability of the matrices to support electro-responsive neonatal rat cardiomyocytes (NCs) was explored. Cells were also submitted to electrical stimulation for 24 h (1V, 5 ms pulse duration and 5 Hz frequency) using a C-PACE® system, similar to what has been described for NCs cultured on other biomimetic matrices.[108, 109] NCs cultured onto rHCI matrices showed comparable connexin-43 levels with and without electrical stimulation vs. control groups, see FIG. 14A. Meanwhile, cells cultured onto rHCIII matrices had lower levels of connexin-43 vs. controls ≈60% (p=0.0009, t-test; see FIG. 14A).

Mononuclear cell adhesion to the collagen matrices was also assessed to gain further insights on monocyte adhesivity onto rHCI and rHCIII-based hydrogel matrices including chondroitin sulfate. FIG. 14B shows that the number of cells adhered onto the collagen matrices remain the same between the two groups (p>0.5, t-test). The ability of M0 macrophages to migrate within the matrix was also assessed. The number of M0 macrophages that migrated within the rHCIII doubled those counted for the rHCI, see FIG. 14C (p=0.018, t-test). Macrophage polarization was next measured and the results indicate that both matrices direct into M2 macrophage polarization, see FIG. 14D, with rHCIII matrices almost doubling the trend seen for rHCI (p=0.038). Gene expression for ECM remodeling proteins including MMP1, 2, and 9, Arg1 as well as TIMP1 and 2 for M2 macrophages cultured onto rHCI and rHCIII matrices indicates only up-regulation of MMP1 and Arg1 for cells cultured on both matrices (p>0.5 rHCI vs. rHCIII), with no statistically significant changes for any of the other proteins, see FIG. 14E. Notably, Arg1 expression increased by ≈100× vs. control TCPS. Further, the effect of the rHCI and rHCIII matrices to protect adhered macrophages when exposed to hydrogen peroxide ($H_2O_2$) was studied; the results indicate that the percentage of positive 7-amino actinomycin D (7-AAD), non-viable population, decreased when the cells were cultured on collagen matrices (p<0.05 vs. the control group), see FIG. 14F.

Since mononuclear cells adhered and also were able to infiltrate within the rHC-based matrices, the effect of culturing cardiac fibroblasts in cell media containing secreted factors from macrophages cultured onto either rHCI or rHCIII matrices was assessed, see FIG. 14G. a-SMA gene expression remained unaffected when compared to the TCPS control group (p>0.5, t-test). However, a ≈66% reduction of the a-SMA levels were seen for TGF activated cardiac fibroblasts when incubated in the presence of cell media containing secreted factors for macrophages cultured onto the rHCI-based matrix (p=0.046 vs. TCPS), see FIG. 14H.

In this Example, injectable hydrogels have been developed and studied for cardiac applications. The present hydrogels are of particular interest due to their ease of use and the possibility of minimally-invasive delivery. Generally, biomaterials may potentially provide physical stability to the infarcted myocardium, and may also act as a biomimetic matrix for supporting cell proliferation. Although injecting collagen post-MI may seem counterintuitive given the presence of the collagenous scar, the composition and mechanical properties of the scar are vastly different from the normal myocardium (71, 19).

In the present studies, using the two most abundant recombinant human collagen types within the healthy heart, type I and III, two new injectable matrices were developed, which had intrinsic differences in their biophysical properties, see FIG. 1B&C (viscosity, porosity, and enzymatic degradation), and which demonstrated good injectability and gelation at 37° C.; identifying them as suitable for testing in a clinically relevant MI-rodent model, see above. Injection of the matrices was carried out following accepted protocol (63, 87-88, 78, 62, 52, 56, 57, 72, 86, 79, 73, 15). Interestingly, the animals treated with rHCI matrices showed an increase in LVEF when compared to rHCIII, and PBS that progressively worsened. Recovery of LVEF function was accompanied by a preservation in the end systolic volume (ESV) and increment in fractional area change, stroke volume, and cardiac output; all markers for overall improvement in cardiac function. The rHCIII matrix also presented some features for restoring cardiac function, however, its activity is closer to what has been observed upon injection of animal origin collagen matrices in established scars, which is preventing cardiac function worsening. The beneficial functional effects elicited by the matrices were also seen in their ability to prevent adverse cardiac remodeling. Mechanical properties of the myocardium were restored within days post-treatment for both collagen formulations, but mechanical reinforcement alone is not the only factor playing a role in recovering cardiac function, as the mechanical properties of the hearts were comparably restored, above PBS levels, for both rHCI and rHCIII matrices. The functional improvement in cardiac function seen for rHCI was accompanied by a decrease in the infarct size, with no significant differences with rHCIII. Also, remote wall-thickness increased only for the rHCI group, suggesting a beneficial cardiac remodeling for animals treated with rHCI-based hydrogel matrix. Thus, the capacity of the presently described collagen-based hydrogel matrices (including chondroitin sulfate) to improve cardiac function post-MI in an established scar, and particularly for rHCI-based matrices, suggests a desirable and particularly interesting platform for clinical use for hearts that have past the initial inflammatory phase post-MI.

Changes in tissue vascularity and number of α-SMA positive cells (myoblasts) were quantified by immune-staining as part of these studies. Interestingly, there was no overall changes in the blood vessels density within the ischemic area amongst the experimental groups. This observation is interesting, and differs from previous findings using animal source collagen that promotes revascularization of the infarcted tissue and reduction in the number of activated myoblasts (62). However, capillary density statistically increased in the border zone of the infarct for both rHCI and rHCIII groups. Without wishing to be bound by theory, increasing blood supply from the peripheral area of the infarct may be linked to preventing cell death and consequently expanding the ischemic area (i.e. smaller infarct sizes). Number of M2 macrophages within the infarcted region 28 days post-treatment was ≈1.5 fold larger for rHCI vs. PBS or rHCIII. This increment in pro-healing macrophages also differs from what has been previously found for other injectable collagen matrices, see for example (62), and aligns well the the now presently observed increase in cardiac function observed for the rHCI group. Interestingly, experiments using Cxcr3-EGFP mice whose hearts were harvested after 2 days of treatment, indicate that rHCI consistently reduces the number of infiltrating +GFP cells recruited from the marrow, as well as reduces the % of M1 phenotype macrophages within the infarct. However, no significant differences in the M2 abundance were detected among the groups (not shown). Interestingly, only for the rHCI treated group, a significant difference in the number of Troponin positive cells in the border zone of the infarct was observed when compared to either PBS or rHCIII. Without wishing to be bound by theory, such differences may account for the improvement in cardiac output herein observed for the rHCI group.

When assessing the biological performance of the presently developed matrices using an in-vitro model, the impact of the matrices to sustain cell proliferation of neonatal cardiomyocytes without and with electrical stimulation was assessed. Notably, only independently of the electrical stimulation, rHCI outperformed rHCIII at promoting connexin-43 expression level, which suggested rHCI as providing a better-suited proliferative environment for cardiomyocytes under the conditions tested. Cell adhesion is of particular importance for dictating functional response in endogenous regeneration, which in this case may link the increased number of macrophages for the rHCI group. Adhesion experiments carried out using murine mononuclear cells showed no significant differences between the two tested rHC groups. However, macrophage migration into the matrices showed a 2-fold larger number of cells migrating through the rHCIII matrices vs. rHCI. Since the pore sizes for rHCIII were considerably larger than that from rHCI, a more facile cell permeation for rHCIII may be observed. However, those differences may be directly involved in a faster degradation of the matrix within the cardiac muscle. Conversely, macrophages cultured onto the matrices favorably polarized into M2 phenotype, being the polarization extent statically larger for rHCIII. However, no considerable differences in gene expression levels for remodeling proteins were detectable. Although the recovery of cardiac function is multifactorial, preferential M2 polarization induced by the present matrices may play a role in certain biological effects of the injectable formulations. Thus, in these studies, rHCIII matrices may be relatively more susceptible to macrophage invasion and consequently more rapidly degraded, which might account for differences in effective pro-functional recovery versus rHCI.

Both rHCI and III matrices in these studies were able to reduce the percentage of damaged cells when incubated in the presence of hydrogen peroxide. These results suggest the ability of the present 3D structures to act as a biocompatible niche, providing a biomimetic template, which may shield cells from endogenous oxidative stress, and which may prevail within the infarcted myocardium. Cardiac fibroblasts cultured in the presence of cell culture media of macrophages cultured onto the matrices did not show any significant differences in α-SMA expression levels. Incubation of pre-activated cardiac fibroblasts with cell culture media of macrophages seeded onto the matrices indicated that only media from rHCI reduced the a-SMA expression level in cells to a 60%. Without wishing to be bound by theory, this result suggests a positive effect of the rHCI matrices with some underlying paracrine effect derived from the interaction of the matrix and infiltrating macrophages within the infarcted area.

The present studies indicate that the presently developed matrices may provide for preventing adverse cardiac remodeling, and (particularly for rHCI) improvement in cardiac function in an established scar as was observed. Our results further support use of the presently developed matrices for combination with cell therapies or surgical procedures aimed to restore cardiac function post-myocardial infarction, for example.

Materials and Methods

Preparation and Characterization of 3D-Collagen Matrices for Cardiac Tissue Engineering:

A 1.0% collagen solution was prepared by dissolving 0.1 g of lyophilized collagen (Type I and III recombinant native collagens, rHCI, and rHCIII, from Fibrogen) in 10 mL of ultra pure ddH$_2$O (Sigma). This constitutes one batch of collagen solution. The solution was left on a shaker overnight at 4° C. The samples completely dissolved in solution within 7 days. Following this period, the solution was poured in a 10 mL pre-sterilized syringe with a capped spout. The solution was centrifuged at 1500 rpm for 15 minutes (repeated five times) and stored at 4° C. The plunger was inserted with assistance by a hypodermic needle the next day. A 1.5 cm length of tubing (1.5 cm) replaced the capped spout before storage.

Injectable materials were prepared using an enclosed system which allowed homogenous mixing without adding bubbles.

Figure 10:
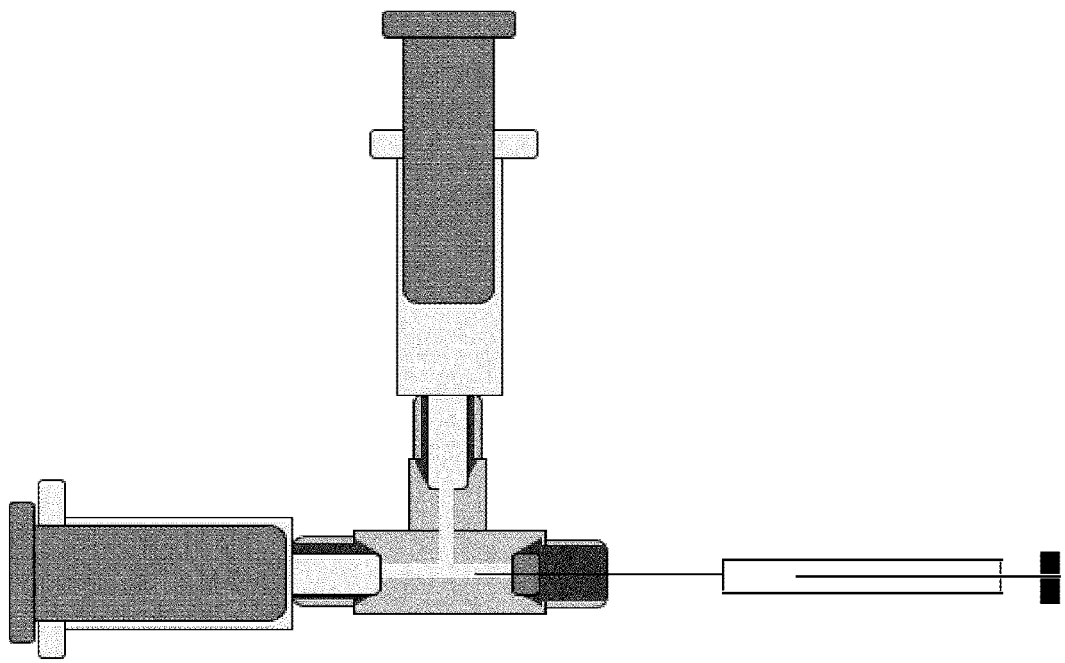
FIG. 10 shows an example of a mixing system for preparing hydrogel compositions described herein, which comprises a T-Piece System as described in the methods section of Example 1.

The 1.0% hydrogel injectable materials were prepared using a T-Piece System (see FIG. 10). All solutions and components are pre-sterilized. An ice container cooled the T-Piece System throughout the procedure between mixing and injection stages. A T-joint having 3 inlets, which are locked with three fittings, was used. A rubber septum was placed in one of the horizontal fittings for needle access. A glass syringe as attached to one of the open fittings, loaded with 2.0 mL of 1×PBS. The solution was injected into the system, with the excess removed until a dome of PBS is apparent on the other opened fitting. A hypodermic needle was used to pierce the dome and eliminate air bubbles. Another glass syringe was prepared as above, which was firmly attached to this opened fitting. The PBS was mixed between both attached syringes to remove air bubbles. One syringe was removed, containing PBS, and the excess was expelled. This was repeated three times, alternating syringes. When the system was equilibrated, with one fitting open with a dome of PBS, the cold collagen stock (rHCI or III) in a 10 mL BD syringe was retrieved from a 4° C. fridge. The third glass syringe was attached to the tubing end of the BD collagen syringe, and 1.0 mL of collagen was transferred to the glass syringe. The glass syringe with collagen was connected to the T-Piece System and mixed 20 times repeated twice. In a 1.0 mL BD syringe with a 27 G needle, 150 μL of 1×PBS was added to the system via the rubber septum. The system was mixed 20 times, repeated twice. In a 1.0 mL BD syringe with an 18 G needle, 100 μL of 40% Chondroitin Sulfate was added to the system via the rubber septum. The system was mixed 30 times, repeated twice. For the cross-linking, 500 μL of 0.1 M MES buffer was added to pre-weighed EDC and NHS. The resulting injectable solution was adjusted to pH 7.4 using microvolumes of NaOH (1.0 N). The solution was mixed briefly using a vortex. Afterward, 200 μL of NHS and EDC are mixed in a 1:1 ratio for a total of 400 μL final volume. In a 1.0 mL BD syringe with a 27 G needle, 200 μL of EDC/NHS mixture was added to the T-Piece System via the rubber septum. The system was mixed 20 times. In order to attain ~7.2 pH, a total of 40 μL (rHCI—current batch) and 45 μL (rHCIII—current batch) was injected into the system. This was completed by maximum aliquots of 25 μL per injection, using a 100 μL Hamilton syringe via the rubber septum. At this stage, the reaction mixture was pumped into one of the glass syringes and removed from the T-joint. The mixture was immediately ready for injection, or stored on ice for up to 45 minutes.

In developing this procedure, different concentrations of EDC and NHS were tested to provide materials with desirable injectability and gelation time post-injection. The final mixture contained chondroitin sulfate and EDC and NHS with a mass ratio of 1:4:0.5:0.3 chondroitin sulfate to NHS to EDC.

Material Viscosity:

Viscosity measurements were carried out in a Brookfield R/S plus rheometer (Brookfield Engineering Laboratories, Inc., Middleboro, Mass.) at 37° C. to more closely mimic physiological conditions.[72, 73] A C25-2/30 conical spindle compresses the material (50 μm displacement) onto a temperature controlled pedestal. Viscosity was measured by a ramp rotational block (parameter: speed 1/min units) pre-set at 5 units to 300 units shear rate over a time of 30 minutes.

Crosslinking Degree:

Differential scanning calorimetry (DSC) experiments were carried out to assess the crosslinking degree of the materials. Briefly, measurements were carried out in a Q2000 differential scanning calorimeter (TA Instruments, New Castle, Del.) in the range of 8 to 80° C. using a scan rate of 5.0° C. min$^{-1}$. Collagen matrices with masses between 5.0-20 mg were surface-dried with filter paper and hermetically sealed with an aluminum lid (Tzero; TA Instruments) in an aluminum sample pan (Tzero; TA Instruments). The denaturation temperature (Td) was measured at the onset of the endothermic peak.

Water Content:

Water content of the materials was measured by weighing the "wet weight" ($W_0$) of the sample, equilibrated in PBS for 96 h at 4.0° C. The material was then dried under vacuum at room temperature for another 96 h to obtain the dry mass (W). The total water content of the hydrogels ($W_t$) was then calculated according to the equation:

$$W_t = \frac{(W - W_0)}{W} \times 100.$$

Collagenase Degradation:

Enzymatic degradation by type I collagenase digestion was measured using 50-100 mg of hydrogels in vials containing the collagenase enzyme in a PBS solution at 37° C. (5.0 ml of a 10 U/ml solution of type I collagenase). Remaining solid mass was measured at increasing time intervals for up to 24 h. Values reported in this work correspond to the degradation rate of mg/min calculated from the initial slope of the plots of remaining mass vs. time.

Material Micro-Morphology:

To gain information on the material micro-morphology, low temperature scanning electron microscopy (Cryo-SEM) measurements were carried out in a Tescan (Model: Vega II—XMU) equipped with a cold stage sample holder at −50° C. using a backscattered electron detector (BSE) and a secondary electron detector (SED). Pore sizes were measured from at least 250 individual pores using ImageJ® software, as similar to the described for other collagen matrices.[74]

Sample Size Calculation

The minimum sample size (n) for detecting a difference of a 20% in LVEF between any 2 groups was calculated using:

$$n = \left[ \frac{(z_\alpha + z_\beta)(s)}{(x - \mu_0)} \right]^2$$

where $z_\alpha$ is a standard approximation at a significance level of α=0.01 to account for multiple comparison groups by Bonferroni correction (α set at 0.05/4=0.01; $z_\alpha$=2.57), $z_\beta$ estimated at a β error of 0.10 (=1.28), s the standard deviation of baseline LVEF (≈16%), $x-\mu_0$ to the mean LVEF increase of the group to be compared to the reference group (hypothesized to be 20%). Using the equation, a minimum sample size of 9 mice is obtained. Endpoint was restoring of cardiac function after 28 days of treatment. Subsets of the animals were taken for histological and mechanical testing.

Myocardial Infarction Model and Injection Post-MI:

A clinically relevant mouse model of MI was induced in 9 week old female C57BL/6 mice (Charles River) by ligation of the left anterior descending coronary artery (LAD) just below its emergence from the left atrium.[75, 76] This procedure results in a large MI involving the antero-lateral, posterior, and apical parts of the heart.[77] All procedures were performed with the approval of the University of Ottawa Animal Care Committee, in accordance with the National Institute of Health Guide for the Care and Use of Laboratory Animals. Mice were anesthetized (2% isoflurane), intubated, and the heart was exposed via fourth intercostal thoracotomy and LAD-ligated. At 1-wk post-MI (baseline), echocardiography was performed using a Vevo770system (VisualSonics) with a 707B series real-time micro visualization scan head probe (VisualSonics) and mice randomly assigned to receive via 5 equivolumetric intramyocardial injections (10 µl each site, 50 µl total), of PBS (control), rHCI-based or rHCIII-based matrices, using an insulin syringe and a 27 G needle, a technique that we have extensive experience with.[59, 78, 79, 80] The mice were then observed for 4 weeks post-treatment, after which they were sacrificed (5 weeks total time post-MI) and hearts were collected for histology analysis and/or measurements of the mechanical properties of the infarcted left ventricle. Additional experiments were carried out for MI and injections, where animals were euthanized only 2 days after injection and hearts harvested for measuring mechanical properties of the left ventricle.

Follow-Up of Cardiac Function in Animals Post-Injection:

Assessment of heart function was assessed by long axis 2D echocardiography in B-mode. Measurements were taken at baseline before treatment injection, as well at days 2, 7, 14, 21, and 28 post-injection. Cardiac function and ventricular remodeling were assessed by calculations of left ventricular ejection fraction (LVEF), fractional area change (FAC), end systolic volume (ESV) and end diastolic volume (EDV). Note that LVEF, ESV, and EDV are clinical predictors of HF prognosis and survival after MI.[44]

Mechanical Properties of Infarcted Cardiac Tissue:

At 2 or 28 days post-injection, animals were euthanized and hearts collected. Rectangle pieces (2.5×5 mm) of the infarcted left ventricle were excised to measure Young's modulus in an Instron mechanical universal tester (Model 3342, Instron, Norwood, Mass.) equipped with Series IX/S software, using a crosshead speed of 10 mm min$^{-1}$.

Histology/Immunochemistry for Infarcted Cardiac Tissue:

Slides of myocardial tissue sections were prepared from a subset of hearts that are not used for mechanical properties measurements. At 28 days post-injection hearts were harvested, embedded in OCT, snap frozen and cut into 10 µm sections at −20° C. Tissue sections were fixed in 4% PFA and stained using Masson's trichrome procedure (Sigma) to assess infarct size using the mid-line arc method as well as remote wall thickness. Images were taken with an Olympus BX50 microscope with a 2× objective. For immunohistochemistry, tissue sections were fixed in acetone for 20 min, permeabilized with 0.1% Triton for 10 min and then blocked in 10% serum for 1 hour at room temperature. The primary antibodies were incubated overnight at 4.0 in 10% serum and finally the appropriate secondary antibodies were incubated with the tissue for 1 hour at room temperature. Slides were mounted with fluorescent mounting medium (Dako). For detection of blood vessels and myofibroblasts antibodies to PECAM-1 (Santa Cruz 101454, 1:50) and α-SMA (Abcam 5694, 1:200) were used and detected with the following secondary antibodies, AF594 anti-rat (Life technologies A11008, 1:500) and AF488 anti-rabbit (Life technologies A11007, 1:500). M2 macrophages were detected by AF488 conjugated anti-CD206 antibody (Biolegend 141710, 1:50). Fluorescent images were obtained using a Zeiss Axio Observer microscope with a 20× objective. To analyze the blood vessel density in infarct and remote heart tissue, tissue sections were fixed in acetone for 20 min, and incubated with rat CD31 and anti-mouse PECAM-1 (Santa Cruz, 1:50), and rabbit anti-mouse alpha-SMA (Abcam, 1:100). These antibodies were detected with anti-rat IgG Alexafluor 488 conjugated and anti-rabbit IgG Alexafluor 555 conjugated secondary antibodies (Life Technologies, both 1:500). The number of different inflammatory cell types (NK cells, M1 and M2 macrophages and leukocytes) in the tissue was examined by standardized immunohistochemistry protocols.[81, 82, 83]

Cell Compatibility of Injectable Materials for Fibroblastic Cardiac Cells:

Neonatal rat ventricular myocytes (NRVMs) were freshly isolated as previously described.[110] First, trypsin (Amersham Biosciences, Piscataway, N.J.) and collagenase type II (Worthington Biochemical, Freehold, N.J.) were used for digestion of heart ventricle tissues collected from 2-day-old rats (Sprague-Dawley, Harlan, Indianapolis, Ind.). Isolated NRVMs were resuspended in M-199 medium (Life Technologies) supplemented with 10% FBS, 19.4 mM glucose, 2 mM 1-glutamine, 2 unit/mL penicillin, 0.8 µg/mL vitamin B12, 10 mM HEPES, and 1×MEM non-essential amino acids (Sigma-Aldrich). Cardiac fibroblasts were removed by two rounds of 60-min preplating, which allow the fibroblasts to attach to the dish bottom and removed from the cell suspension. After the preplatings, cells were plated at 40,000 cells/cm$^2$ onto the different collagen matrices in 24-well plates and cultured for 12 hr without electrical stimulation. Successively, cells were submitted to electrical stimulation for 24 h (0.4V, 5 ms pulse duration and 5 Hz frequency) using a C-PACE® system (Ion Optix LLC., Westwood, Mass.). After the 24 h of pacing, cells were fixed with 4.0% PFA and stained with mouse anti-alpha sarcomeric actinin antibody (α-SA; 1:400, Sigma-Aldrich) and rabbit anti-connexin 43 antibody (Cx43; 1:200, Sigma-Aldrich).[108, 109] Secondary antibodies conjugated to Alexa Flour® 488 and Alexa Flour® 546 (Life Technologies, Carlsbad, Calif.) and a DAPI counterstain (Vector Laboratories, Burlingame, Calif.) to the cell nucleus were used. The samples were imaged with Zeiss Axiovert 200M Fluorescence microscope equipped with an AxioCam MR camera (Carl Zeiss, Oberkochen, Germany). For the quantitative analysis, the number of α-SA and Cx43 double-positive cells was counted at randomly selected 3 areas. Each sample was assessed by n=4.

In vitro experiments were performed on cardiac fibroblasts isolated from mouse hearts at a density of 1×10$^4$ cells/cm$^2$. Cells were seeded onto the different collagen matrices and cultured for 5 days; control group was seeded directly onto the cell culture well. RNA isolation using the RNeasy kit (Qaigen) for RT-qPCR analyses were collected at days 1, 3 and 5 post-seeding. The following gene expression were analyzed for gaining further insights on the role of the matrices as regenerative scaffolds; α-smooth muscle actin, collagen α1, MMP2 and elastin (Primer sequences are included in Table 1 below).[84, 85] In all cases, experiments were carried out using Lightcycler SYBR green master mix (Roche) in duplicate from three biological replicates. Data was analyzed using the ΔΔCt quantification method as each sample was corrected to 18S housekeeping gene expression and the expression of the target gene in the cells at time 0 before plating on the gels.

TABLE 1 qPCR amplification primer sequences.

| Target Gene | Primer Sequence (5'→ 3') |
|---|---|
| αSMA | F: TCG GAT ACT TCA GCG TCA GGA (SEQ ID NO: 1)<br>R: GCT CCA GAC ATC AGG GAG TAA (SEQ ID NO: 2) |
| Col-1A | F: GGG CAA GAC AGT CAT CGA AT (SEQ ID NO: 3)<br>R: ATT GGG GTG GAG GGA GTT TA (SEQ ID NO: 4) |
| MMP-2 | F: CAG GGA ATG AGT GGG TCT ATT (SEQ ID NO: 5)<br>R: ACT CCA GTT AAA GGC AGC ATC TCA (SEQ ID NO: 6) |
| 18S | F: CGG CTA CCA CAT CCA ACG (SEQ ID NO: 7)<br>R: CTG GAA TTA CCG CGG CT (SEQ ID NO: 8) |

Forward and reverse primer sequences used for the q-PCR amplification to determine the gene expression level of αSMA, Col-1A, MMP-2 and 18S (housekeeping).

Mononuclear Cells Adhesion and Macrophage Polarization

Bone marrow-derived macrophages were isolated from C57BL/6J mice aged 8-12 weeks as previously described.[111] Briefly, mice were euthanized by carbon dioxide inhalation and cervical dislocation; tibia bones were collected and flushed with media to isolate the bone marrow. The freshly isolated cells were cultured for 1 week in DMEM supplemented with 10% FBS, 20% L929 conditioned media and penicillin-streptomycin. Following 7 days of culture cells were lifted using 5 mM EDTA/HBSS (without $Ca^{2+}/Mg^{2+}$) and plated on the collagen hydrogels for 3 days. Cells were collected from the fibers by digesting the collagen using a 3 mM $CaCl_2$ Hank's buffer saline solution containing 250 units of collagenase I (Gibco). Macrophage polarization was assessed by flow cytometry (FACS Aria III; Becton Dickinson) using CD86 (Biolegend) to identify macrophages with a M1 phenotype and CD206 (Biolegend) for those with a M2 phenotype. For mononuclear cell isolation, bone marrow from tibia bones were collected as previously described. Mononuclear cells were purified by density gradient centrifugation using Histopaque®-1083 (Sigma) according to the manufacturer's instructions. Mononuclear cells were labelled using 0.5 m/ml 4,6-Diamidino-2-phenylindole (DAPI; Sigma), for 30 min at 37° C.

For cardiac derived fibroblasts, hearts were isolated from C57BL/6J mice aged 8-12 weeks, finely minced and digested in 2.4 U/ml dispase I (Roche) and 1 mg/ml Collagenase B (Roche) for 40 min at 37° C. Digested hearts were titrated to dissociate remaining cardiac tissue fragments and centrifuged at 400 g for 5 min. Cell pellet was washed with 3 times with PBS and plated on TCPS plates in DMEM/F12 (Fisher) supplemented with 10% FBS (Fisher). Media was changed after 24 h in culture and every 3 days until confluent. For fibroblast activation to myofibroblasts, cells were treated with 50 µg/ml TGF-β.

For primary cell culture experiments, tissue was harvested from C57BL/6J mice aged 8-12 weeks. Mononuclear and macrophage cells were isolated from the tibia bones while fibroblasts were isolated from cardiac tissue. Macrophages were generated by flushing the bones with media (DMEM supplemented with 10% FBS, 20% L929 and penicillin-streptomycin) and cultured for 1 week. Following 7 days of culture, cells were lifted using 5 mM EDTA/HBSS (without $Ca^{2+}/Mg^{2+}$) and plated on the collagen hydrogels for 3 days. Cells were collected from the fibers by digesting the collagen using a 3 mM $CaCl_2$ Hank's buffer saline solution containing 250 units of collagenase I (Gibco). Macrophage polarization was assessed by flow cytometry (FACS Aria III; Becton Dickinson) using CD86 (Biolegend; M1 phenotype) and CD206 (Biolegend; M2 phenotype). For mononuclear cells, bone marrow cells were subjected to density gradient centrifugation using Histopaque®-1083 (Sigma) according to the manufacturer's instructions. Mononuclear cells were labelled using 0.5 µg/ml 4,6-Diamidino-2-phenylindole (DAPI; Sigma) for 30 min at 37° C.

For cardiac fibroblasts, hearts were finely minced and digested in 2.4 U/ml dispase I (Roche) and 1 mg/ml Collagenase B (Roche) for 40 min at 37° C. Digested hearts were titrated to dissociate remaining cardiac tissue fragments and centrifuged at 400 g for 5 min. Cell pellet was washed with 3 times with PBS and plated on TCPS plates in DMEM/F12 (Fisher) supplemented with 10% FBS (Fisher). Media was changed after 24 h in culture and every 3 days until confluent. For fibroblast activation to myofibroblasts, cells were treated with 50 µg/ml TGF-β.

Macrophage Migration Assay

Macrophages cultured for 7 days as described above ($2\times10^5$) were labeled with 50 µg/ml of 4',6-diamidino-2-phenylindole (DAPI; Sigma) for 30 min at 37° C. to stain the nucleus and loaded into the upper chamber of a Transwell plate (Life Technologies) coated with 100 µL of rHCI or rHCIII. The upper chamber containing EBM lacking growth factors and serum while the bottom chamber contained full macrophage media as described above. After 48 h, the inserts were removed and the migratory macrophages that passed through the biomaterial were quantified in a blinded fashion using a Zeiss Z1 fluorescence microscope.

Cxcr3-EGFP MI Induction and Treatment

To evaluate the recruitment of mononuclear cells to the myocardium following biomaterial delivery, B6.129P-Cx3cr1 tm1Litt/J mice (Cx3cr1) were purchased from The Jackson Laboratory and used as previously described.[112] Briefly, myocardial infarction surgery and 50 ul of PBS, collagen I or collagen III was delivered 1 week post-MI as described earlier. Animals were sacrificed at 2 days and hearts were collected. Blood was collected into EDTA containing tubes while hearts were perfused with PBS and the right ventricle was removed. The apical region of the left ventricle, just above the ligation suture, was also collected. Right and left ventricle tissue was rinsed with HBSS and digested in 2.4 U/ml dispase I (Roche) and 1 mg/ml Collagenase B (Roche) for 40 min at 37° C. Samples were washed 3 times with PBS followed by 5 min 400 g centrifugations then processed for flow cytometry analysis. Antibodies used for flow cytometry, following dilutions from the suppliers (0.25 µg/L per $1\times10^6$ cells for CD11b, Ly-6 G/6C, CD38, and CD206 as per F4/80 a 1 µg per $1\times10^6$ cells); APC anti-mouse/human CD11b (Biolegend 101211), PE anti-mouse Ly-6 G/6C (Biolegend 108407), PE/Cy5 anti-mouse F4/80 (Biolegend 123111), PE/Cy7 anti-mouse CD38 (Biolegend 102717) and Alexa Fluor® 700 anti-mouse CD206 (141733).

Example 2

SOPs for the Preparation of Hydrogel Compositions

This example provides a non-limiting embodiment of an SOP which may be used for preparing hydrogel compositions as described herein. It will be understood that this example is intended as a non-limiting and illustrative example intended for the person of skill in the art, and that various suitable modifications, additions, deletions, and/or substitutions may be made to the described procedures.

Initial Notes:

Preparation of the hydrogels so as to avoid contamination, error, and breakage is desired. Therefore, during the following procedures, it is recommended that the following be observed. As will be understood, proper aseptic technique is to be observed throughout. A flow diagram is provided in FIG. 11 for reference. Recommendations are as follows:

Collagen is only to be removed from the 4° C. fridge when it is to be used immediately.

When punching holes into the septum, use one piece to create four smaller septa of equal diameter.

When using the vortex, handle the eppendorfs of EDC and NHS by the lids to reduce heat transfer to the samples.

When priming the T-piece system, ensure you inspect for leaks often and constantly dry the exterior of the T-piece.

Ensure a dome-to-dome connection is achieved when connecting the syringes to the T-piece.

During collagen transfer to the 2 ml syringe, let the plunger sit slightly above the sample to avoid contamination.

When injecting anything into the hydrogel, ensure to apply a slight backpressure on the syringe.

When injecting anything into the hydrogel, ensure to remove the needle quickly and in a swift motion.

When mixing the T-piece, ensure to push each plunger down enough until the tap of the glass with the syringe is heard.

When washing with PBS, take a 20 ml syringe and take 15 ml of PBS to wash 10 wells instead of doing each well one at a time. This also applies to transferring media onto the plates. This saves time and allows for less exposure to potential contaminants.

When injecting the 40% chondroitin solution, make sure the yellow 25 g BD needle is being used and when injecting the EDC/NHS solution, the blue 20 g BD needle is being used.

Preparation of Injectable Collagen Hydrogel Using 1.0% Collagen and EDC/NHS (1:1) Chemistry A procedure for the preparation of a collagen hydrogel using a 1.0% stock solution is provided. The procedure provides for the preparation of an injectable collagen hydrogel using EDC/NHS chemistry.

Recombinant type I and III human collagen from FibroGen was used in this procedure, and MSDS sheets and Batch analysis certificates and certificates of analysis data were documented for the EDC, NHS, PBS, chondroitin, MES buffer, and collagen used.

For this SOP,
EDC is N-(3-dimethylaminopropyl)-N'-ethylcarbodiimide;
NHS is N-hydroxysuccinimide;
PBS is phosphate buffer saline pH 7.4;
MES is 2-morpholinoethane sulfonic acid monohydrate; and
Safety and Environmental Considerations Material fabrication and packaging is carried out in a controlled environment in which microbial and particulate levels are maintained at or below the required limits.

At all stages, collagen solutions are stored at 4-6° C. or immersed in ice water to minimize degradation, denaturing and fibrillogenisis during the material preparation.

All equipment used in the manufacturing of the materials are pre-cleaned according to suitable Cleaning SOP.

Procedure:

Equipment and Materials:

Reaction Mixing System—Used to mix collagen solution with cross-linking reagents.

Components:
T-joint
3 fittings
3 Glass syringes (3 ml)
Rubber septum
2 blue cork borer (for rubber septum)
100 μl and 50 μl Hamilton syringes+needles
1.0 mL BD syringes+needles
Wide plastic dish (Ziploc container) to hold ice water and submerge system
Ice storage container (foam box)
Ice
Parafilm Reaction Plating System:

Depending on the desired application, the gel may be poured in well plates (96 to 6 wells). The thickness of the resulting gel may be estimated using the diameter of the well and the volume of solution poured, by applying the equation of the volume calculation for a cylinder.

Fabrication Procedure

Record lot/batch numbers of reagents and storage history of collagen solution.

Prepare jigs and lay out clean, unused molds for the number of implants to be fabricated.

Prepare 0.1M MES Buffer, filter the solution through a 0.22 μm filter. Degas the solution for 15 min.

For EDC and NHS solution prepare:
NHS 25 mg in 500 μl of sterile MES buffer (5.0% w/v);
EDC 15 mg in 500 μl of sterile IVIES buffer (3.0% w/v);
Use a clean digital microbalance to weigh out the powder.

Suck approximately 2 ml of sterile PBS into the syringe and position it in a vertical manner to get air bubbles to the top, do it slowly. Slightly tap the syringe and eject the air bubbles.

Attach the syringe to the T-joint (see FIG. 10). Twist the syringe to firmly attach it to a Luer lock of the T-joint.

A dome of liquid is pushed through to the remaining open side. Pierce the dome with a microsyringe plunger to remove any left bubbles. A second 2 mL syringe is then added to this side and the buffer is mixed to remove any air bubbles within the liquid. Repeat this for a total of three times, alternating syringes.

Remove cold collagen stock in BD syringe (10 ml) from 4° C. fridge.

Attach a dry glass reaction syringe to BD stock solution syringe via rubber piece and apply light backpressure on glass syringe while applying more pressure on the BD syringe to pump 1.0 ml of collagen into the glass syringe. Return stock collagen solution to 4° C. fridge immediately.

Connect this syringe to the T-piece system and mix, note that changes in the sample fluidity and color will be seen (mix 20 times repeated twice). Further, add another 150 µl of PBS buffer through the septum using a Hamilton syringe and then mix another 20 times repeated twice. Place the system in the ice bath.

Add 100 µl of the 40% chondroitin solution using a 1.0 ml syringe. Addition will be slow to minimize backpressure. Mix another 60 times making sure the system is kept cold while mixing. Place the system in the ice bath.

Mix the EDC and NHS solution in a 1:1 ratio (400 µl final volume).

Aliquot 200 µl through the septum the total amount of the EDC:NHS mixture from a fixed-needle syringe and mix another 20 times, place the system in ice each between mixing. Place the system in the ice bath.

For Theracol—Add 70 µl of a NaOH 1.0 N solution, in aliquots of 25 µl, 25 µl, and 20 µl, to the system using a Hamilton syringe. Mix 10 times and put the system back in the ice, repeated for each aliquot.
  For Recombinant Human Collagen Type I—Add 70 µl of a NaOH 1.0N solution.
  For Recombinant Human Collagen Type III—Add 65 µl of a NaOH 1.0N solution.

Pump the whole reaction mix into one syringe and detach this syringe from the T-joint and proceed to pour the gel. Note that a small fraction of the gel will be poured on a pH strip to check the resulting pH of the mixture.

Soak and clean reusable components.

Figure 11:
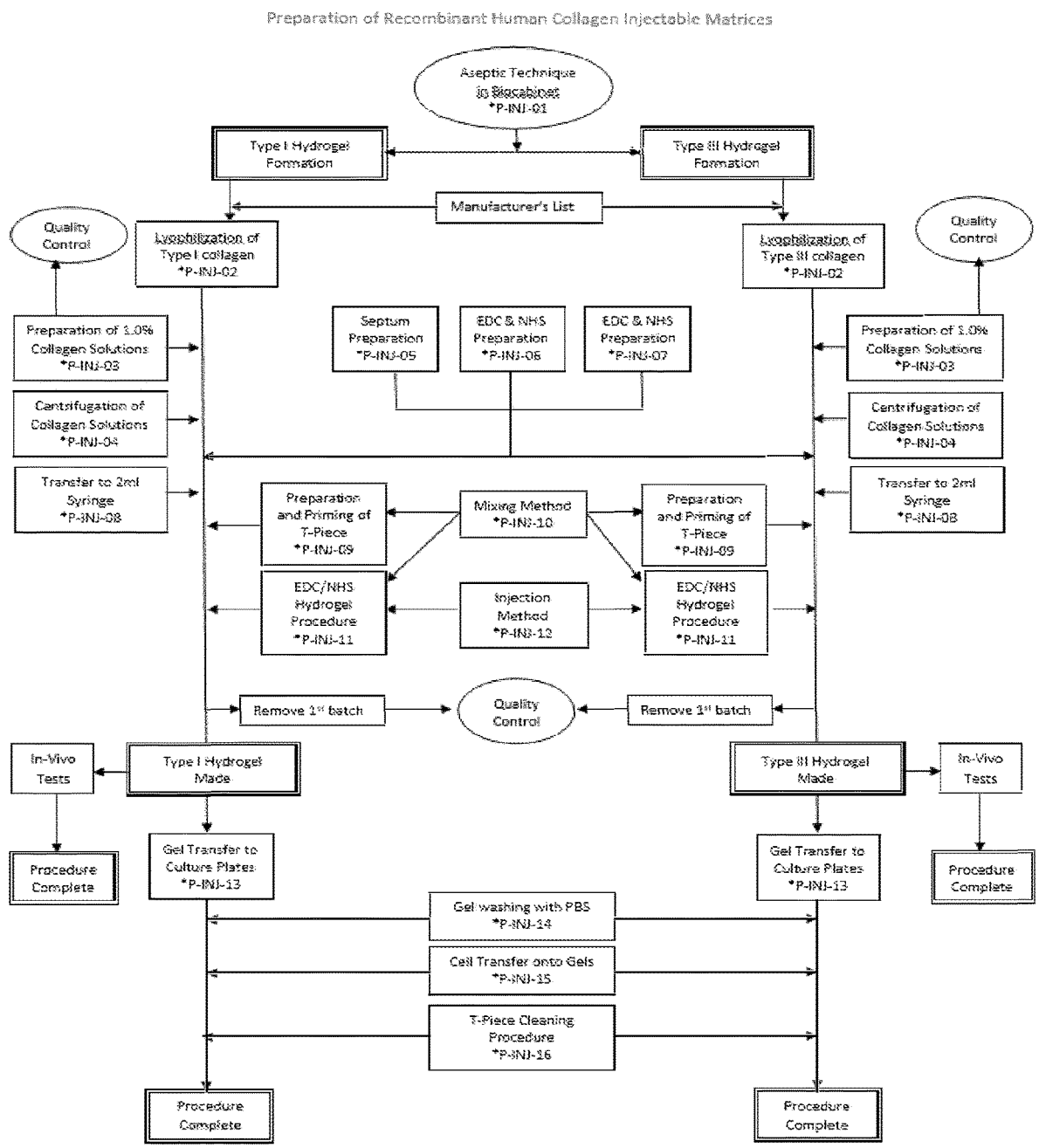
FIG. 11 provides a flow chart for exemplary preparation methods for collagen Type I and Type III-based hydrogel compositions, as further described in Example 2.

For further preparation method examples and description, see FIG. 11 which provides a flow chart for exemplary preparation methods for Type I and Type III-based hydrogel compositions.

Operation of T-Piece System and Injection Method

For further clarity, proper injection of reagents into the T-piece system without causing damage to the contents is described. Reagents are injected into the T-piece system via the septum.

Equipment and Materials
  Appropriate sized needle
  Appropriate sized syringe
  T-piece
  Septum Injection Procedure
  Attach the needle to the syringe and draw up the appropriate amount of reagent that is needed for injection.
  Place the T-piece on the table and place your thumb on the opposite syringe to apply a slight backpressure.
  Insert the needle at a moderate speed, hitting the center of the septum with the needle's tip.
  While injecting the needle, twist the needle to ease the entry.
  Inject the needle so it is 1 cm into the T-piece system. Push the plunger of the needle down to push the reagent into the T-piece and also apply a slight backpressure at this time.
  Remove the needle in a moderate speed and place in sharps bin.
  If another injection is to be done, repeat steps above.

Use of the T-Joint Mixing System

An example procedure for use of the T-Joint mixing system is as follows:

This procedure is carried out quickly so that the contents can be mixed thoroughly. One full cycle of mixing is described; in other words, the following procedure describes '2 times of mixing'.

Figure 12:
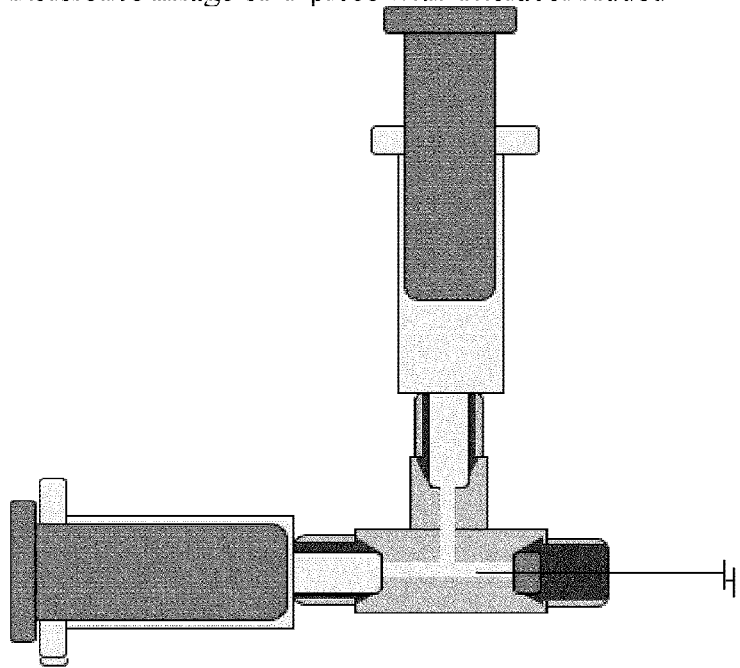
FIG. 12 provides example reference images of an installed T-piece mixing system for use in the SOP procedures described in Example 2.
Figure 12:
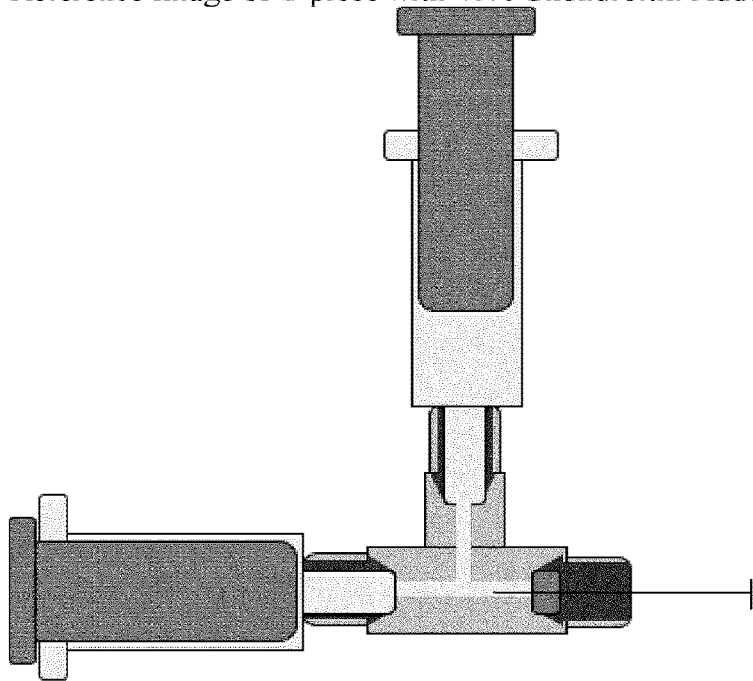
Figure 12:
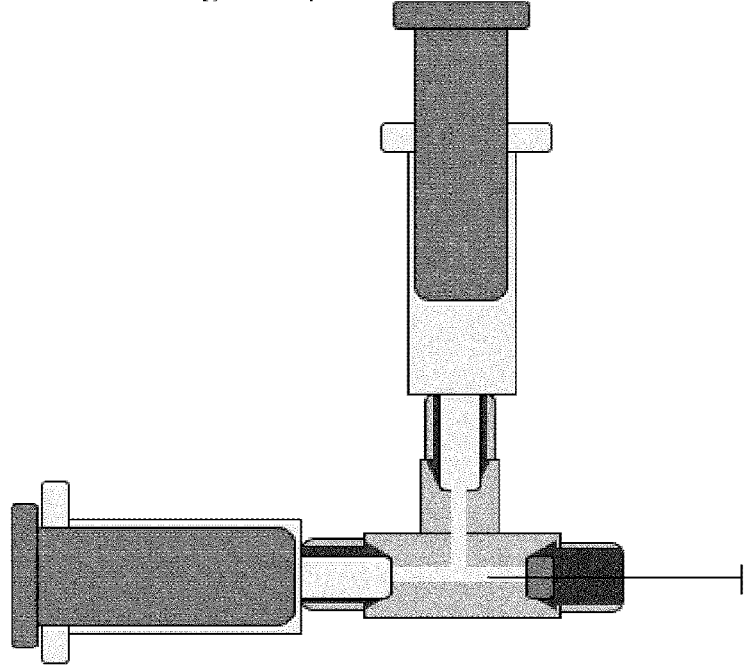
Figure 12:
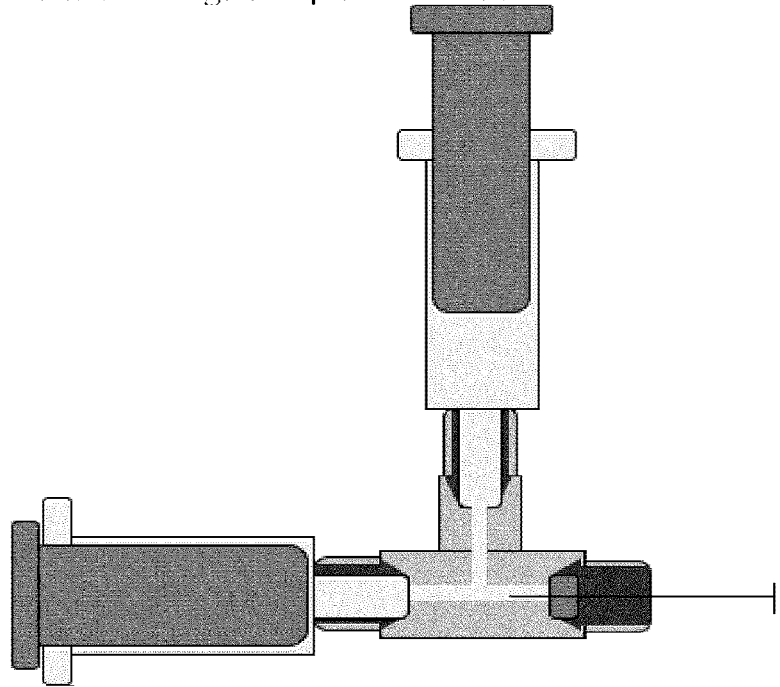
Figure 13:
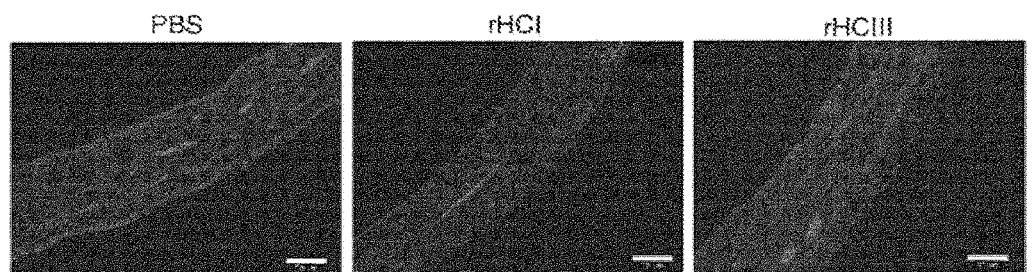
FIG. 13: Recombinant human collagen hydrogels and heart revascularization, changes in number of pro-healing macrophages, changes in post-inflammatory response upon treatment, and changes in the number of cardiomyocytes in the border-zone. (A) provides images for immunohistochemistry tissue sections of infarcted myocardium areas of the heart treated with PBS, rHCI, and rHCIII (A); total number of capillaries, arterioles, and myofibroblasts per mm$^2$ counted in infarcted tissue (A') (see experimental in Example 1 for further details); and total number of capillaries, arterioles, and myofibroblasts per mm$^2$ counted in the border zone tissue (A"). Emission fluorescence shown in the figure corresponds to blood vessels (PECAM-1/AF594; red) and myofibroblasts (α-SMA/AF488 green), DAPI nuclei staining is shown in blue. Scale bars in the images correspond to 50 μm. Numbers reported in the Figure correspond to the average of 4-6 samples, and ±bars correspond to standard error. p values calculated from two tail t-test.
Figure 13:
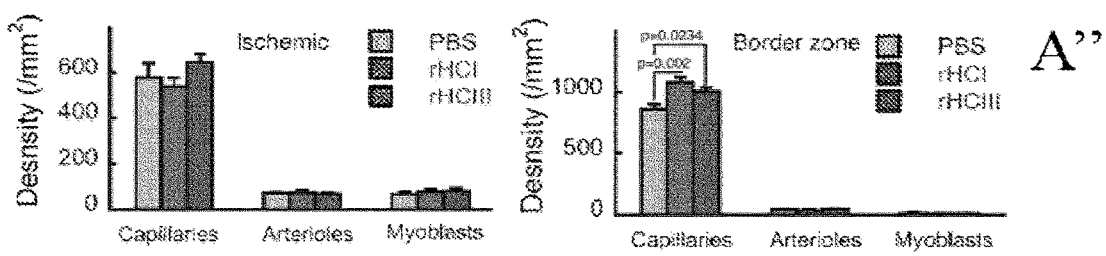
Figure 13:
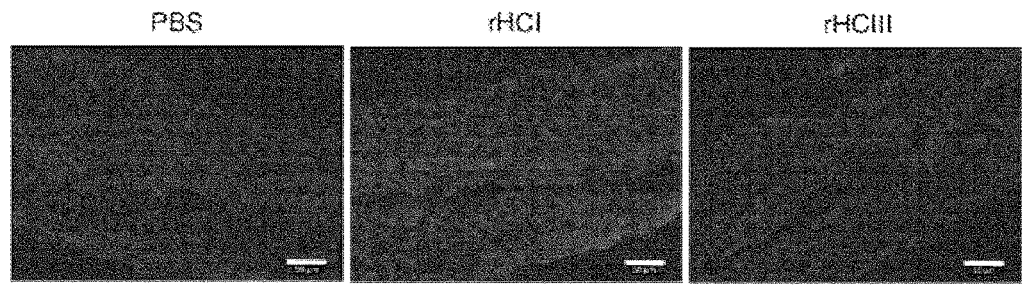
Figure 13:
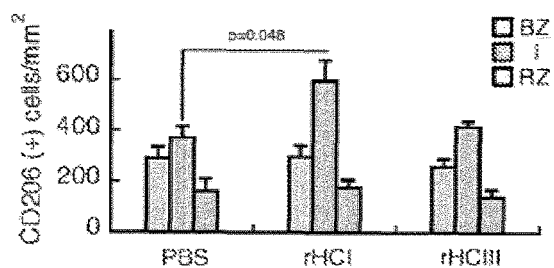
Figure 13:
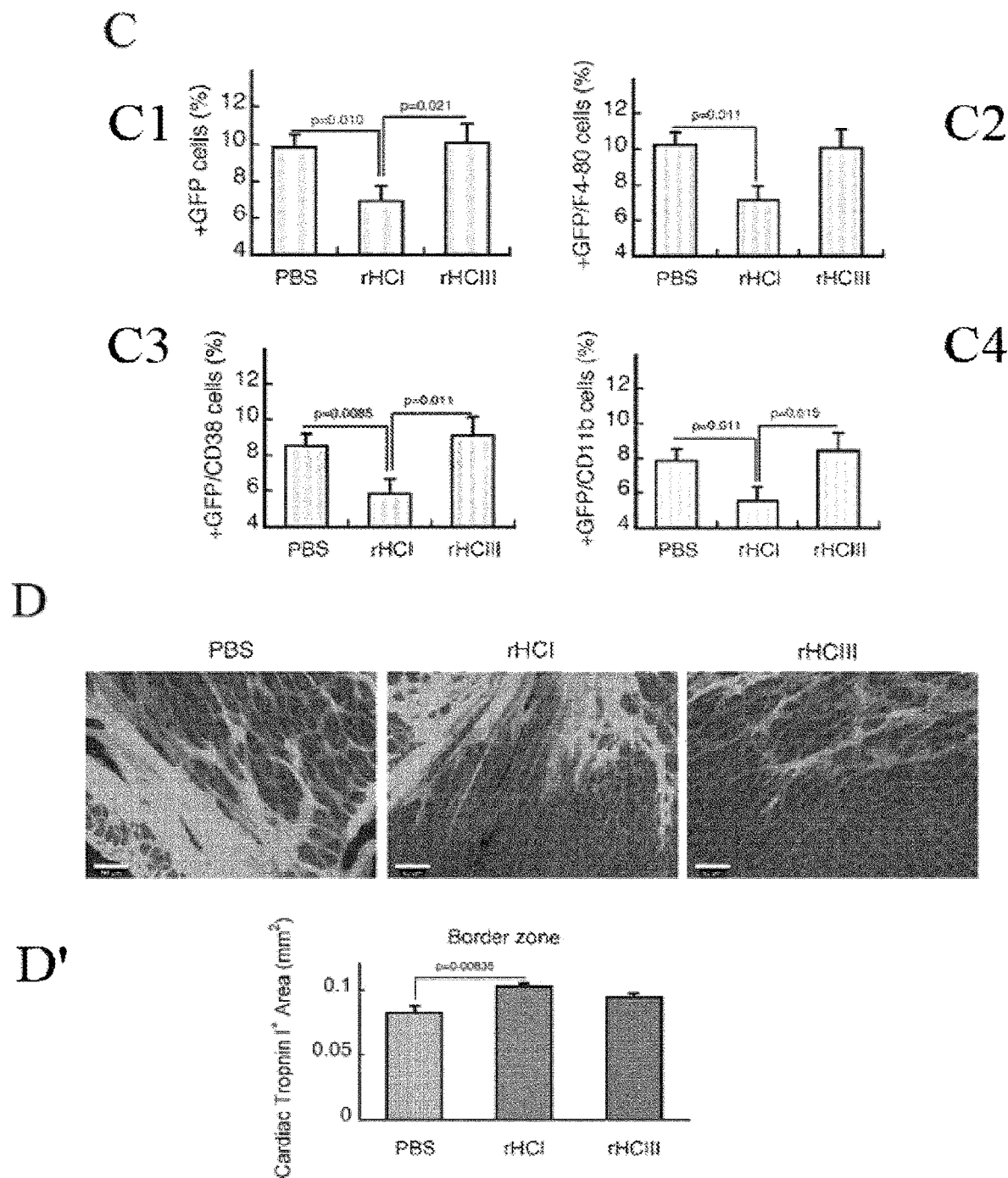
Figure 14:
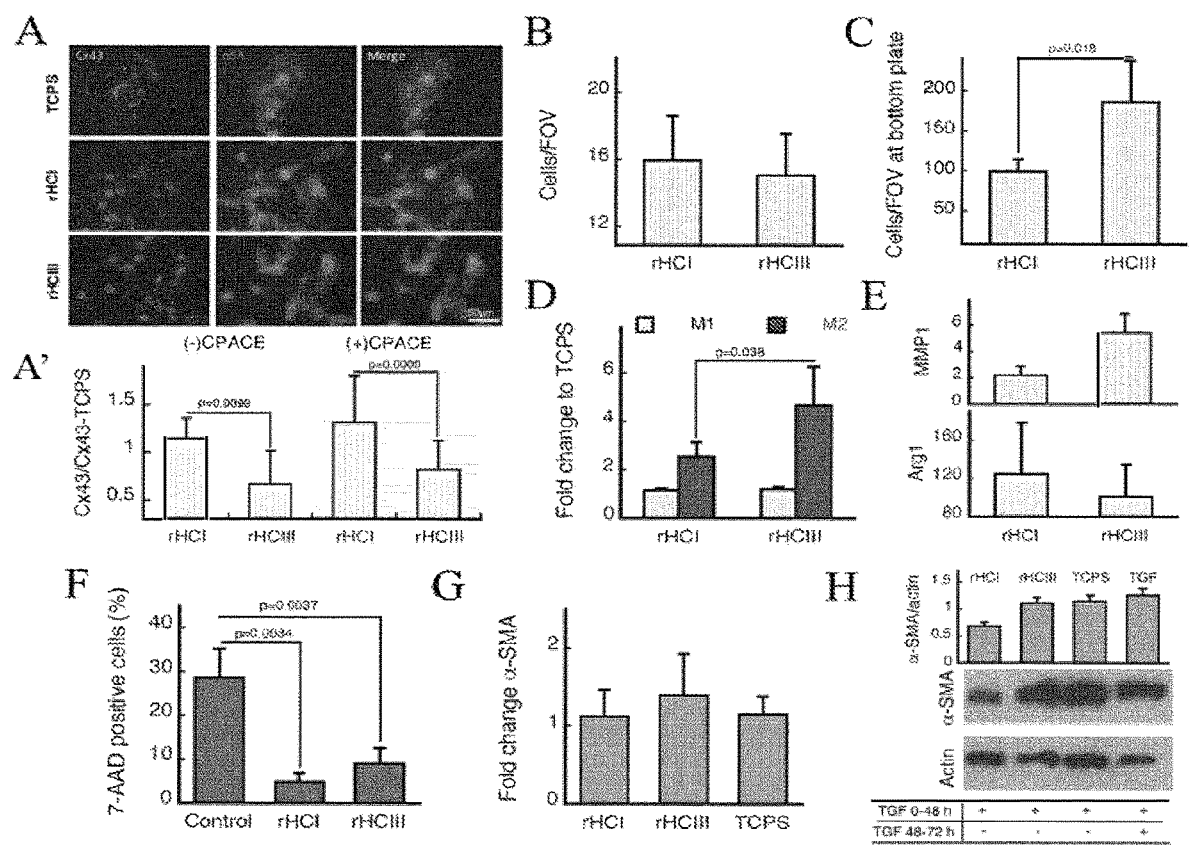
FIG. 14: Recombinant collagen matrices supported cardiomyocytes, monocyte adhesion, macrophage M2 polarization, as well as protected cells from oxidative stress. (A) shows immune fluorescence images for neonatal rat cardiomyocytes cultured on rHCI or rHCIII collagen matrices with 40,000 cell s/cm$^2$ and cultured for 24 h with electrical stimulation (0.4V, 5 ms, 5 Hz) (A). Connexin 43 antibody (Cx43, green), alpha sarcomeric actinin (α-SA, red), DAPI (blue). (B) shows number adhered mononuclear cells onto rHCI and rHCIII. Cells. A chart depicting Cx43/Cx43-TCPS staining for cells without and with electrical stimulation (n=4) is shown in (A'). The number of adhered mononuclear cells onto rHCI and rHCIII is shown in chart (B). Cells were counted in 4 different random areas from each gel (n=4), 21,000 cells/cm$^2$. Migrating number of macrophages counted at the bottom of a 300 μm thickness collagen hydrogel, quantified from 4 different regions (60,000 cells/cm$^2$) is shown in (C). Macrophage polarization was measured after 72 hours of incubation. M1 and M2 macrophage polarization measured using CD86 and CD206 antibodies after 72 h of incubation is shown in chart (D). Gene expression fold changes measured for macrophage cultured on collagen matrices for 72 h for MMP1 and Arg1 (110,000 cells/cm$^2$) is shown in chart (E). Percentage of positive 7-AAD cells measured upon 3 h incubation with 0.5 mM hydrogen peroxide (130,000 cells/cm$^2$, n=4) is shown in chart (F). The fold change in α-SMA from the analysis of Western Blot is shown in chart (G) and representative α-SMA and β-Actin blot performed on cardiac fibroblasts (30,000 cells/cm$^2$, n=3) treated with media from macrophages cultured on rHCI, rHCIII, and TCPS in the presence of 50 μg/ml TGF-β for 24 h followed by 24 h culture in regular media are shown in panel (H). Error bars in the plots correspond to the standard errors from the mean p values calculated from two tail t-test.
Figure 15:
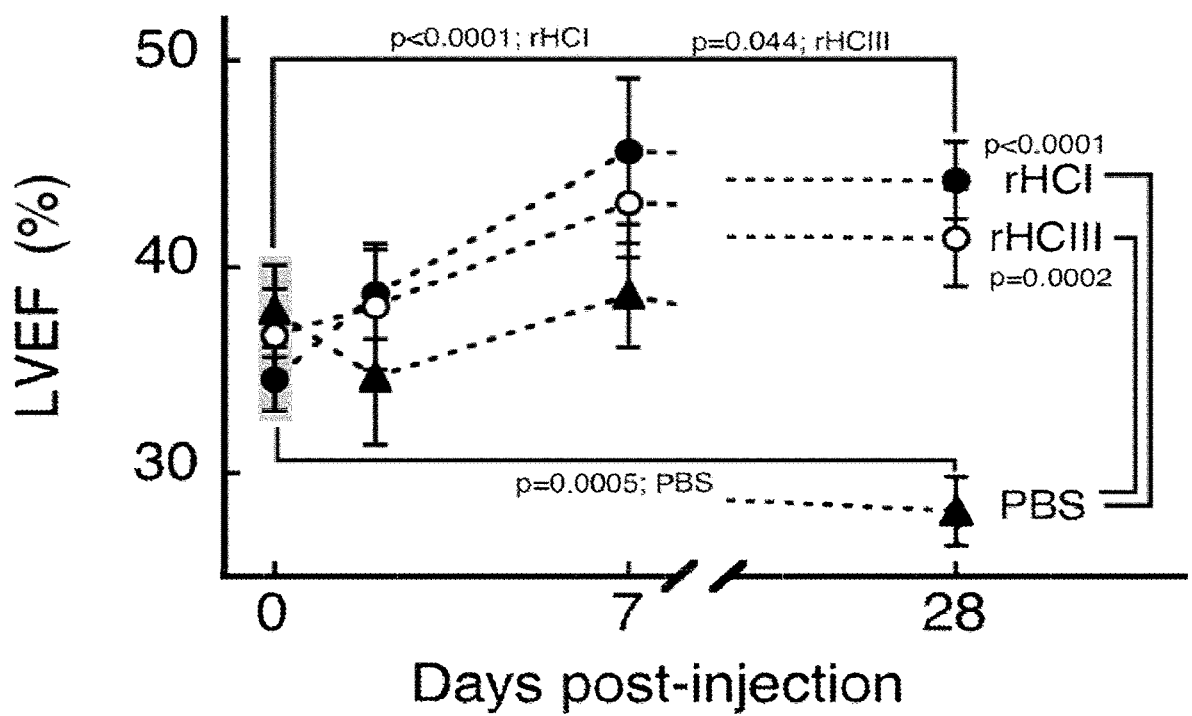
FIG. 15 charts the changes in LVEF at 2, 7, and 28 days after treatment (rHCI (●) and rHCIII (○) and PBS (▲). p values were calculated using t-test for paired data comparing baseline and 28 days. Sample size for days 2 and 7 were n=4 per group, while sample size for days 0 and 28 were: rHCI (n=15), rHCIII (n=14), and PBS (n=11).

T-piece system is connected with 2 syringes (closed system) [See diagrams of installed system and references, FIG. 12]

Pick up the closed system and orient it so that the characteristic 'T-shape' of the system is facing the table. This means that the plunger of syringe 1 should be pointing to the table and the plunger of syringe 2 should be sticking out to the right of the T-piece. This will be called the start position.

Lower the T-piece system to the table so that the plunger of syringe 1 pushes the content of the T-piece into syringe 2.

Rotate the T-piece system so that syringe 2 is now sticking out the left hand side of the T-piece. This is equivalent to performing a 180° spin of the T-piece.

Rotate the T-piece counter-clockwise by 90° so that the plunger of syringe 2 is now pointing towards the table and the plunger of syringe 1 is pointing towards the right side of the T-piece.

Lower the T-piece system to the table so that the plunger of syringe 2 pushes the content of the T-piece into syringe 1.

Rotate the system by 180° so that the plunger of syringe 1 is facing the right side of the T-piece system.

Rotate the T-piece counter-clockwise by 90° so that the plunger of syringe 1 is now pointing towards the table and the plunger of syringe 2 is pointing towards the right side of the T-piece. The system has returned to its start position.

Repeat steps above the appropriate number of times as described in sections above.

Remember that if a procedure calls for 10 mixes, repeat steps 5 more times, and if it calls for 11 mixes, repeat steps 7 five times and then repeat steps one more time to complete 11 mixes.

Preparation and Priming of the T-Piece Mixing System

An example procedure for preparation and priming of the T-Joint mixing system is as follows:

Equipment and Materials
  T-piece
  Adapters
  Tweezers
  Septum (Refer to Septum Preparation SOP P-INJ-04)
  Ice Bucket
  PBS
  2 ml glass syringes
  Waste beaker
  Hyponeedle T-piece Preparation
  Hold the T-piece so that the "T" shape is upside down and the vertical joint is facing the ceiling.
  Using tweezers, place the septum in the right horizontal side of the T-piece. Push the septum down to make sure it is flat and secured in place.
  Screw in an adapter piece into all the joints of the T-piece.
  Clamp each adapter with the tweezers and twist to tighten the adapter into the T-piece.
  Place this T-piece system on an ice bucket for 5 minutes.

T-piece System Priming
  Extract 1.5 ml of PBS into a 2 ml glass syringe and secure tip of syringe into the left horizontal end of the T-piece system.
  Slowly push the all contents of the syringe into the T-piece system, forcing a dome to appear at the top of the vertical adapter. Release each dome into the waste beaker.
  Repeat above step until there is 1 ml of PBS left in the syringe.
  Create another dome of PBS at the end of the vertical adapter.
  Extract 1.5 ml of PBS in another glass syringe. Push contents of syringe slowly down towards the tip until a dome of PBS is formed at the tip.
  Attach the dome of the syringe to the dome of the vertical adapter and push down so the syringe and T-piece are now connected.
  Leave the already attached syringe inside the T-piece system.
  Mix the contents of the syringe. Perform 20 rotations.
  Disconnect both syringes and dump used PBS into the waste beaker.
  Repeat steps above a total of 3 times.
  Once cleaned, attach only one syringe with 1 ml PBS in it to the left horizontal end of the T-piece.
  Note: Inspect for leaks from the adapters and T-piece at all times. If leaking, restart and use a different T-piece set.
  Clean all used materials appropriately according to suitable Cleaning SOP.

Injectable Collagen Hydrogel Transfer to Culture Plates

Hydrogels may be placed (plated) into a well-plate and solidified in an incubator as follows:
  Procedure
  Equipment and Materials
    1.5 ml eppendorf
    P1000 Pipette
    Well plate (the size of the well plate is dependent on how much is required)
    Marker
    Incubator
  T-piece Preparation
    Transfer all the hydrogel into an eppendorf.
    Using the equation for the volume of a cylinder ($v=\pi r^2 h$), calculate the volume of the hydrogel needed for each well, where height is the desired thickness (200 um) of the gel and the radius is the radius of one well.
    Using a P1000, pipette the calculated volume and transfer it to a well-plate.
    Ensure that the gel solution is added drop by drop into the well, while rotating the well plate to allow the gel to spread evenly across the surface of the well.
  Repeat steps above for each well using the pipette.
  Cover the well plate with the lid and label the contents, name and date. Place in the incubator at 37° C. for 30 minutes to solidify.

Washing of Incubated Hydrogels Using PBS

Hydrogels may be washed using PBS in preparation for usage as follows:
  After the hydrogels solidify in an incubator at 37° C. for 30 minutes, remove them and place in a biocabinet.
  Using a pipette, add about 1.5 ml of 1×PBS (for 6 well plate) onto each gel, ensuring the entire surface of the gel is covered with PBS. Let this sit for 30 minutes.
  Pipette off the old PBS and then using a new tip, pipette another 1.5 ml of PBS onto the gel surface. Ensure the entire surface is covered for 30 minutes.
  Repeat the two steps above a total of 4 times to ensure the gel is completely washed (8 washes total).
  After the washes, place the hydrogels with PBS in the 4° C. fridge until use.

Cell Transfer onto Hydrogels

Where desired, cells may be transferred onto prepared hydrogels. Below is an example of a standard operating procedure (SOP) to safely transfer cardiac fibroblast cells onto the hydrogels. Such hydrogels may be used, for example, for testing cellular responses to the gels.

Definitions
  Trypsin is a digestive enzyme found in the small intestine
  PBS is phosphate-buffered saline
  Gibco cell media with phenol red, a pH indicator, made of nutrients which is used for the growth of the cardiac fibroblast cells.
  Cardiac fibroblasts are cells found in the cardiac muscle.
  Ethanol is a colorless, volatile and flammable liquid mainly used as a disinfecting agent in laboratories.
  Trypan blue is a chemical dye used for cell counting as it marks dead cell membrane.
  Collagen is the most abundant protein present in the human body.

Procedure
Equipment and Materials
  Trypsin (0.25%)
  Cardiac Fibroblast cell plates
  Aspirator
  Pipettes
  Incubator
  Gibco DMEM F12 Media
  Centrifuge
  50 ml Centrifuge tubes
  15 ml Centrifuge tubes
  Eppendorf
  Trypan Blue
  Hemocytometer
  Kimwipes Preparation for Counting
  Remove Trypsin from the −20° C. freezer and allow it to thaw at room temperature for approximately 20 minutes.
  Remove the cardiac fibroblast plates from the incubator and aspirate all the media off and wash 1× with PBS.
  Pour 5 ml of 0.25% Trypsin onto each cardiac fibroblast plate. Gently 'wash' the plate by shaking the plate gently in a circular fashion.
  Place each cardiac fibroblast plate in the incubator for 3 minutes.
  Observe the cardiac fibroblast plate underneath a microscope to see if the cells are floating. In other words, if small circles move through the viewing area, the cells are 'floating'.
  If the cells are not floating, incubate these plates for another 2 minutes then wash thoroughly by pouring 5 ml of media with serum and mixing by using a pipette to suck up and then release the media mixture quickly.
  For all the now 'floating' cells, place all the cell mixture into individual 50 ml centrifuge tubes for each plate and centrifuge at 300 G for 8 minutes.

Remove the supernatant into a smaller 15 ml centrifuge tube and centrifuge this for 5 minutes at 300 G.

Carefully aspirate the supernatant from the 15 ml tubes into a waste beaker.

Resuspend cells in media with supplements and pipette out all the pellets from the 15 ml tubes and place into the 50 ml tube that also only contains cell pellets.

Counting Procedure and Preparation for Seeding

Pipette 45 µl of the cell solution into an eppendorf and mix with 5 µl of trypan blue.

Place 10 µl of this blue cell-solution into each end of the Blueline Hemocytometer and count the number of cells that appear on the grid.

Calculation: Viable cells=#live cells/#large squares counted×dilution×10,000.

Note: Do not count the bright blue cells as those cells are dead.

If the variation between the two counts of either end of the Hemocytometer differs by 15%, redo the process above.

Average your number of cells counted and then do the calculation above. This is the number of cells in your solution.

Clean the Hemocytometer with ethanol and gently dry with kimwipes.

According to the number of cells per 45 µl of your sample, dilute your sample with enough media so you achieve the correct number of cells per well for your experiment. Cell density must be 50,000 cells/well.

Cell Seeding onto Gels

Remove the hydrogels from the 4° C. fridge.

Aspirate off all the PBS on the gels and label all wells appropriately

Pipette 0.5 ml of media into each well

Pipette the correct amount of cell solution (calculated in step 7.3.6) into each well Culture the wells in the incubator at 37° C.

Preparation of Collagen for Preparing the Stock Solution used in the Fabrication Procedure—Lyophilization An example procedure for preparing the collagen is as follows:

Solution is prepared in a sterile environment where the controlled environment keeps microbial and particulate levels at or below the required limits.

Prior to the procedure, the collagen is stored in a 4° C. fridge.

When the collagen is removed from a 4° C. fridge, the collagen is prepared for lyophilization as quickly as possible to prevent denaturation.

Equipment:
  50 ml centrifuge tubes
  Collagen
  Kimwipes
  Rubber bands
  900 ml freeze dry system tubes
  Rubber lids
  Glass junctions
  Laminar hood Lyophilization Technique:

Label each 50 ml tube with "Collagen 35 ml", date, lot number and operator.

Under a hood, add 35 ml of collagen to each 50 ml tube and loosely tighten the lids of each tube.

Place the tubes in a −80° C. freezer for 1 hour.

Remove the tubes from the freezer, remove the lids in biocabinet and secure a kimwipe on the top of each tube with a rubber band.

Place 3 tubes into each 900 ml glass container and seal the tube with the large rubber lid.

Attach the tube to the lyophilizer with the glass junction and turn on the vacuum. Let it sit in the system for 7 days.

After 7 days, turn off the vacuum and remove the 900 ml glass container.

Spray the tubes and caps very well with ethanol and place in the sterile laminar hood.

Place the 50 ml centrifuge caps under the hood and under UV light for at least 10 minutes. Do the same with some extra 50 ml centrifuge tubes.

Disassemble the 900 ml plastic container and remove the kimwipes and rubber band from each 50 ml centrifuge tube.

Screw on the sterile centrifuge caps for each tube and place in a 4° C. fridge.

Preparation of Collagen Stock Solution Used in the Fabrication Procedure

An example procedure for preparing the collagen stock solution using the lyophilized collagen is as follows. Collagen is kept inside the 4° C. fridge unless in use, where it should be transported on ice. When measuring the collagen, place it in a closed vial to transport to the microbalance.

Equipment and Materials:
  Clean, 20 ml vial
  Digital Microbalance
  Biocabinet
  Ice Bucket
  Lyophilized collagen (refer to P-INJ-01 and above for procedure)
  Tweezers
  Spatula
  10 ml pipette
  Ultra pure water
  Pipette tips
  Cold room with shaker (Labnet GyroTwister)

Measuring procedure:

Take a clean vial from the biocabinet and tare on the microbalance.

Spray the vial with ethanol, place back in the biocabinet and let dry.

Remove the lyophilized collagen from the 4° C. fridge and place in the biocabinet by transferring on an ice bucket.

Using tweezers, and if necessary a spatula, break a piece of collagen off and place inside the vial.

Close the vial and measure on the microbalance.

Repeat the two steps above until 0.1 g collagen is in the vial. Push the collagen inside the vial to be as flat as possible.

Place the collagen back in the 4° C. fridge.

UV a 10 ml pipette for 1 minute inside the biocabinet. Ensure that no collagen, media or cells are inside the biocabinet when this happens.

Pipette enough ultra pure water to achieve 1.0% dilution of collagen. For the 0.1 g of collagen, pipette 10 ml of water.

Use a clean pipette tip to push the collagen lightly into the water so it has full contact with the ultra pure water.

Label the vial with its contents, name, date and lot number.

Place the vial on a shaker in a cold room at a moderate speed for 1 week.

Quality Control for 1.0% Collagen Solution

Example of inspection criteria for quality control of solutions are as follows:

| Inspection Stock Solution | Criteria |
|---|---|
| Solution Color | Colorless |
| Solution Transparency | Clear and Transparent |
| Syringe | Physical Aspect |
| Tubing | Physical Aspect |
| Absorbance | Theracol: |
| (1/100 dilution in MilliQ water) | PV: 2.273 ± 15% |
|  | SV: 0.602 ± 15% |
|  | Type I Collagen: |
|  | PV: 2.120 ± 15% |
|  | SV: 0.382 ± 15% |
|  | Type III Collagen: |
|  | PV: 2.251 ± 15% |
|  | SV: 0.533 ± 15% |
| BCA | Theracol: 3741.5 ± 80.0 µg/ml |
| (1/100 dilution in MilliQ water) | Type I Collagen: 626.2 ± 281.5 µg/ml |
|  | Type III Collagen: 703.1 ± 100.4 µg/ml |

Centrifugation of 1.0% Collagen Solution

An example procedure for centrifuging the 1.0% Collagen Solution is provided.

Procedure
 Equipment and Materials
  Sterile 50 ml syringes
  $dH_2O$
  Collagen
  Ice bucket
  Centrifuge
  50 ml centrifuge tubes
  Parafilm
 Method
  Fill 2 syringes with equal amounts of $ddH_2O$.
  Centrifuge these tubes at 484 G for 25 minutes at 4° C.
  Note: This step is done to bring the temperature of the centrifuge down to 4° C. before actually using the collagen.
  Remove the collagen from the fridge and place on ice.
  Centrifuge the collagen for 30 minutes at 484 G with a temperature of 4° C.
  Repeat step above until all the air bubbles that are visible with the naked eye from the collagen sample are removed. This usually takes about 3 or 4 centrifugations.
  Remove the collagen from the centrifuge and fill the tube with enough $ddH_2O$ so that the tube only contains collagen and $ddH_2O$. In other words, there is no space for air inside the tube. Then, parafilm the lid of the tube and place it back on ice.

Collagen Transfer to 2 mL Syringe

An example procedure for transferring the collagen sample to a 2 mL glass syringe using a hyponeedle, for use in the T-piece system, is provided.

Procedure
 Equipment and Materials
  Collagen (in syringe sealed with parafilm)
  10 mL Syringe and plunger
  Hyponeedle (18 g, 6" long)
  Plastic Tubing
 Transfer Technique
  In the biocabinet, place the Hyponeedle and syringe and plunger under UV light for 10 minutes.
  Remove the collagen from the fridge and place in biocabinet
  Remove parafilm and insert the Hyponeedle and plunger into the syringe at the same time and push down both the hyponeedle and plunger at the same rate. Usually, this will require a bit of applied force as air is being forced out of the syringe.
  Push the Hyponeedle and plunger down until the plunger hits the top of the collagen sample inside the syringe.
  In the presence of a large air bubble, use the needle to gently poke a small hole through the rubber plunger to allow the air bubble to escape.
  Slowly remove the Hyponeedle and place the collagen sample with the plunger attached back into the fridge and wrapped in parafilm until further use.
  Please note: Usually small tiny air bubbles will appear at the point of contact between the plunger and sample. For type 1 collagen, this amount is insignificant to create a gel and by risking popping the bubbles, one may cause the collagen to leak over the plunger and cause contamination of the sample. This would be wasteful. Do not attempt to pop the air bubbles if they appear too small to create an entire gel.

Transfer to 2 ml Glass Syringe
 Remove the large syringe with collagen in it from the fridge.
 Attach the tubing to the tip of the collagen syringe.
 Obtain a clean and dry 2 ml glass syringe and attach the tip of the 2 ml syringe to the tubing of the 10 ml syringe.
 Ensure all parafilm is removed from the 10 mL syringe and then push the plunger to push collagen into the 2 ml syringe. Note: Apply a slight backpressure on the 2 ml syringe to limit the number of air bubbles that may enter the glass syringe.
 Put the parafilm back onto the 10 mL syringe and place back in the fridge.

Preparation of Clean, Sterile Buffers

Example procedures for preparation of clean, sterile buffers are provided. The preparation of clean sterile buffer solutions of NaOH, PBS and IVIES are described.

Definitions
 NaOH is sodium hydroxide
 PBS is phosphate-buffered saline
 MES is 2-morpholinoethane sulfonic acid monohydrate Safety and Environmental Considerations
 Solutions are prepared in a sterile and controlled environment.
 If need be that the chemicals must leave the biocabinet to be weighed, the chemical must be put in a sterile vial that is pre-tarred and then taken out of the biocabinet.

Procedure
 Equipment and Materials
  NaOH pellets
  Microbalance
  Clean beakers
  PBS tablets
  Double distilled water (ddH2O)
  Parafilm
  MES powder
  pH meter
  2M NaOH
  Pipette 0.2 µm Supor Membrane Non-pyrogenic Syringe Filter
3 large plastic syringes
3 clean 100 ml plastic tubes
Ice bucket NaOH Preparation
Measure 2 g of NaOH on a clean microbalance.
Add 50 ml of ddH2O into a clean beaker.
Place the 2 g of NaOH pellets in the beaker and cover with parafilm.
Label the date, name and "NaOH 1N" and leave overnight.
Refer to steps outlined below in "buffer filtration" for next steps.

PBS Preparation
Fill a clean beaker with 200 ml ddH$_2$O.
Add one PBS pill into the beaker and seal the beaker with parafilm.
Let this sit overnight and label the name, date and "1×PBS".
Spray distilled water on the pH meter's rod and measure the pH of the solution. It should be around pH 7.4.
Refer to steps outlined in "buffer filtration" for next steps.

MES Preparation
Fill an autoclaved bottle with 80 ml ddH$_2$O.
Measure 2.13 g MES on a clean microbalance.
Pour 2.13 g MES into the bottle and stir thoroughly with a spatula.
Spray distilled water on the pH meter's rod and measure the pH of the solution. It should be around pH 3.35.
Using a pipette, start adding 2M NaOH drop by drop into the solution until pH 6.0 is reached.
Remove the pH meter, washing the rod with distilled water again.
Measure the volume of the solution and add the appropriate amount of ddH$_2$O so that the total volume of the solution becomes 100 ml.
Seal the bottle and label "0.1 MES, pH 6.0" with the operator's initials and date.
Refer to steps outlined in "buffer filtration" for next steps.

Buffer Filtration
Place the NaOH, MES and PBS solutions in an ice bucket.
Open a syringe and attach a filter to the tip of the syringe
Place the syringe on top of a 50 ml plastic tube and pour the NaOH into the syringe until the syringe is full.
Insert the plunger of the syringe and push the plunger down, forcing the NaOH down into the plastic tube.
Close the tube and place back in the ice bucket.
Repeat steps above using MES and then once more using PBS.
Label all tubes appropriately with name, date and contents.

Preparation of EDC and NHS Solutions
Example procedures for preparation of EDC and NHS solutions are provided.
Definitions
EDC is N-(3-dimethylaminopropyl)-N'-ethylcarbodiimide
NHS is N-hydroxysuccinimide
MES is 2-morpholinoethane sulfonic acid monohydrate Safety and Environmental Considerations
The solution is prepared in a sterile environment where the controlled environment keeps microbial and particulate levels at or below the required limits
Prior to the procedure, the NHS is stored in a 4° C. fridge and the EDC is stored in a −20° C. freezer.
Once done the procedure, the NHS and EDC eppendorfs are placed back into their respective fridge or freezers.
Equipment used in the manufacturing of the materials is pre-cleaned properly according to suitable Cleaning SOP.

Procedure
Equipment and Materials
Eppendorf Rack
1.5 ml Eppendorfs
Bottle of EDC
Bottle of NHS
Medium sized spatula
Digital Microbalance
Plastic Container
Bottle of MES
P1000 Pipette and tips
Small Ice Bucket Fabrication Procedure
Place respective number of eppendorfs into the rack that is appropriate to the amount of EDC and NHS that is prepared.
Label each eppendorf as either an eppendorf for NHS or EDC. Also label the date of formation and operators initials on each eppendorf.
Remove the EDC and NHS bottles from their respective fridge/freezer and allow them to sit for 10 minutes to thaw.
Place one empty eppendorf on the microbalance and then tare the scale.
Using the small tip of the spatula, fill the eppendorf with 0.025 g of NHS.
Do this quickly to prevent NHS from being tricky to handle due to electrostatic forces in the environment.
Measure the filled eppendorf and if it is the correct amount, place back in the eppendorf rack.
If there is too much NHS in the eppendorf, use the small tip of the spatula to empty some of the NHS into a plastic container and remeasure until correct amount is achieved.
Repeat 4 steps above for each eppendorf labeled NHS.
Then repeat 4 steps above once more, this time using each eppendorf labeled EDC and measuring out 0.015 g of EDC using the large tip of the spatula.
Place the bottle and eppendorfs of EDC back in the −20° C. freezer and the NHS bottle and eppendorfs back in the 4° C. fridge.
Refer to Preparation of Injectable Collagen Hydrogel steps described in detail hereinabove. When ready, remove the EDC and NHS eppendorfs and using a P1000 pipette, place 500 µl of MES into each eppendorf of EDC and NHS.
Hold the tube by the top and use a vortex machine at mid speed to mix contents of each eppendorf. Continue with the preparation of injectable collagen hydrogel.

7 Clean remaining tools according to suitable Cleaning SOP.

Preparation of Septum

An example procedure for preparation of clean and sterile septum is provided.

Definitions

Methanol is colorless liquid alcohol made from oxidizing methane.

The Septum is a small circular rubber piece that is placed inside the T-piece system to create a closed system.

Safety and Environmental Considerations

Solutions must be prepared in a sterile and controlled environment.

Procedure

Equipment and Materials

2 Borer

Large Septum

Tweezers 40 ml beaker

Parafilm

Hyponeedle

Preparation

Use the borer to punch holes into the large septum to create smaller septa.

Insert a hyponeedle into the top of the borer to poke out the septa that is stuck to the borer.

Grasp the septa from the bottom of the borer with tweezers and twist gently to pull the septa out.

Place all septa inside the 40 ml beaker.

Add 15 ml of Methanol into the beaker and then seal the beaker with parafilm. Leave overnight inside the biocabinet.

Remove the septa from the 40 ml beaker with tweezers and into a clean beaker when the septa are to be used.

Discard methanol into a liquid waste bucket.

T-Piece Cleaning Procedure and General Cleaning

An example procedure for T-Piece cleaning and general cleaning is provided.

Definitions

NaOH is sodium hydroxide

PBS is phosphate-buffered saline

MES is 2-morpholinoethane sulfonic acid monohydrate

HCl is hydrochloric acid

Ethanol is a colorless, volatile and flammable liquid mainly used as a disinfecting agent in laboratories Procedure Equipment and Materials ddH$_2$O Biohazard bag dH$_2$O Sparkleen Powder Sharps bin Aluminum foil 0.1M HCl Large beakers Plastic tweezers Sonicator Cleaning Method Wash all bottles with ddH$_2$O and sparkleen thoroughly and place upside down on counter to allow water to drain.

Remove all tape, parafilm and autoclave tape from the bottles and discard in biohazards bag.

Unscrew all adapters from the T-piece and remove septum using tweezers. Discard septum in the biohazards bag.

Fill a large beaker with 500 ml of dH$_2$O and add 3 g of sparkleen powder and mix thoroughly.

Fill all syringes with water and allow water to drain from the tip of the syringe. Repeat 2 times and then place syringes in the 500 ml beaker.

Repeat above step for the adapters and T-piece.

Leave this beaker overnight.

Fill a beaker with 500 ml of 0.1M HCl and use plastic tweezers to quickly transfer all pieces in the dH2O into the HCl.

Cover this beaker with aluminum foil and let it sit overnight.

Remove aluminum foil and use plastic tweezers to transfer the pieces to another beaker filled with 400 ml of dH$_2$O. Let this sit overnight.

Then, pick up each piece and spray with ddH$_2$O to wash off all the HCl.

Place each piece in a clean biocabinet and spray with ethanol and then place under UV light until dry.

Hamilton Syringe Cleaning

Fill a beaker with 400 ml of ddH$_2$O.

Use the Hamilton syringe to suck up the water and then squirt it back out into the sink. Repeat this step at least 5 times to remove any residue stuck inside the syringe. Ensure that a constant stream of water can flow out the needle.

Spray the Hamilton syringe with ethanol and under UV light until dry.

Place the Hamilton syringe back in its respective case.

Hyponeedle Cleaning

Follow Cleaning Method steps above, but place the Hyponeedles in a separate beaker.

After the washing, place the hyponeedles in a sonicator for 10 minutes while on the 'hold' function.

Remove the needles with tweezers and spray the needles with dH$_2$O and allow them to dry on a clean counter.

One or more illustrative embodiments have been described by way of example. It will be understood to persons skilled in the art having regard to the teachings herein that a number of variations and modifications can be made without departing from the scope of the invention as defined in the claims.

REFERENCES

All references cited hereinbelow and/or elsewhere in the specification are hereby incorporated by reference in their entireties.

1. Canada, P. H. A. o. Tracking Heart Disease and Stroke in Canada—Stroke Highlights 2011 http://www.phac-aspc.gc.ca/cd-mc/cvd-mcv/sh-fs-2011/index-eng.php.
2. Mercola, M.; Ruiz-Lozano, P.; Schneider, M. D. Cardiac muscle regeneration: lessons from development. Genes & development 2011, 25 (4), 299-309.
3. Gálvez-Montón, C.; Prat-Vidal, C.; Roura, S.; Soler-Botija, C.; Bayes-Genis, A. Cardiac Tissue Engineering and the Bioartificial Heart. Rev. Esp. Card. (English Version) 2013, 66 (05), 391-399.
4. Deutsch, M. A.; Sturzu, A.; Wu, S. M. At a crossroad: cell therapy for cardiac repair. Circ Res. 2013, 112 (6), 884-90.
5. Assmus, B.; Tonn, T.; Seeger, F. H.; Yoon, C. H.; Leistner, D.; Klotsche, J.; Schachinger, V.; Seifried, E.; Zeiher, A.

M.; Dimmeler, S. Red blood cell contamination of the final cell product impairs the efficacy of autologous bone marrow mononuclear cell therapy. J. Am. Coll. Cardiol. 2010, 55 (13), 1385-94.
6. Henning, R. J. Stem cells in cardiac repair. Future Cardiol. 2011, 7 (1), 99-117.
7. Jeevanantham, V.; Butler, M.; Saad, A.; Abdel-Latif, A.; Zuba-Surma, E. K.; Dawn, B. Adult bone marrow cell therapy improves survival and induces long-term improvement in cardiac parameters: a systematic review and meta-analysis. Circulation 2012, 126 (5), 551-68.
8. Roncalli, J.; Mouquet, F.; Piot, C.; Trochu, J. N.; Le Corvoisier, P.; Neuder, Y.; Le Tourneau, T.; Agostini, D.; Gaxotte, V.; Sportouch, C.; Galinier, M.; Crochet, D.; Teiger, E.; Richard, M. J.; Polge, A. S.; Beregi, J. P.; Manrique, A.; Carrie, D.; Susen, S.; Klein, B.; Parini, A.; Lamirault, G.; Croisille, P.; Rouard, H.; Bourin, P.; Nguyen, J. M.; Delasalle, B.; Vanzetto, G.; Van Belle, E.; Lemarchand, P. Intracoronary autologous mononucleated bone marrow cell infusion for acute myocardial infarction: results of the randomized multicenter BONAMI trial. Eur. Heart J. 2011, 32 (14), 1748-57.
9. Traverse, J. H.; Henry, T. D.; Ellis, S. G.; Pepine, C. J.; Willerson, J. T.; Zhao, D. X.; Forder, J. R.; Byrne, B. J.; Hatzopoulos, A. K.; Penn, M. S.; Perin, E. C.; Baran, K. W.; Chambers, J.; Lambert, C.; Raveendran, G.; Simon, D. I.; Vaughan, D. E.; Simpson, L. M.; Gee, A. P.; Taylor, D. A.; Cogle, C. R.; Thomas, J. D.; Silva, G. V.; Jorgenson, B. C.; Olson, R. E.; Bowman, S.; Francescon, J.; Geither, C.; Handberg, E.; Smith, D. X.; Baraniuk, S.; Piller, L. B.; Loghin, C.; Aguilar, D.; Richman, S.; Zierold, C.; Bettencourt, J.; Sayre, S. L.; Vojvodic, R. W.; Skarlatos, S. I.; Gordon, D. J.; Ebert, R. F.; Kwak, M.; Moye, L. A.; Simari, R. D. Effect of intracoronary delivery of autologous bone marrow mononuclear cells 2 to 3 weeks following acute myocardial infarction on left ventricular function: the LateTIME randomized trial. JAMA 2011, 306 (19), 2110-9.
10. Wohrle, J.; Merkle, N.; Mailander, V.; Nusser, T.; Schauwecker, P.; von Scheidt, F.; Schwarz, K.; Bommer, M.; Wiesneth, M.; Schrezenmeier, H.; Hombach, V. Results of intracoronary stem cell therapy after acute myocardial infarction. Am. J. Cardiol. 2010, 105 (6), 804-12.
11. Delewi, R.; Andriessen, A.; Tijssen, J. G.; Zijlstra, F.; Piek, J. J.; Hirsch, A. Impact of intracoronary cell therapy on left ventricular function in the setting of acute myocardial infarction: a meta-analysis of randomised controlled clinical trials. Heart 2013, 99, 225-32.
12. Ruel, M.; Song, J.; Sellke, F. W. Protein-, gene-, and cell-based therapeutic angiogenesis for the treatment of myocardial ischemia. Mol Cell Biochem 2004, 264 (1-2), 119-31.
13. Tongers, J.; Losordo, D. W.; Landmesser, U. Stem and progenitor cell-based therapy in ischaemic heart disease: promise, uncertainties, and challenges. Eur. Heart J. 2011, 32 (10), 1197-206.
14. Yoon, C. H.; Koyanagi, M.; Iekushi, K.; Seeger, F.; Urbich, C.; Zeiher, A. M.; Dimmeler, S. Mechanism of improved cardiac function after bone marrow mononuclear cell therapy: role of cardiovascular lineage commitment. Circulation 2010, 121 (18), 2001-11.
15. Suuronen, E. J.; Zhang, P.; Kuraitis, D.; Cao, X.; Melhuish, A.; McKee, D.; Li, F.; Mesana, T. G.; Veinot, J. P.; Ruel, M. An acellular matrix-bound ligand enhances the mobilization, recruitment and therapeutic effects of circulating progenitor cells in a hindlimb ischemia model. FASEB J. 2009, 23 (5), 1447-58.
16. Murry, C. E.; Reinecke, H.; Pabon, L. M. Regeneration gaps: observations on stem cells and cardiac repair. J. Am. Coll. Cardiol. 2006, 47 (9), 1777-85.
17. Steinhauser, M. L.; Lee, R. T. Regeneration of the heart. EMBO Mol. Med. 2011, 3 (12), 701-12.
18. Anversa, P.; Leri, A.; Kajstura, J.; Nadal-Ginard, B. Myocyte growth and cardiac repair. J. Mol. Cell Cardiol. 2002, 34 (2), 91-105.
19. Bayomy, A. F.; Bauer, M.; Qiu, Y.; Liao, R. Regeneration in heart disease—Is ECM the key? Life Sci. 2012, 91 (17-18), 823-7.
20. Dobaczewski, M.; Gonzalez-Quesada, C.; Frangogiannis, N. G. The extracellular matrix as a modulator of the inflammatory and reparative response following myocardial infarction. J. Mol. Cell Cardiol. 2009, 48 (3), 504-11.
21. Barallobre-Barreiro, J.; Didangelos, A.; Schoendube, F. A.; Drozdov, I.; Yin, X.; Fernandez-Caggiano, M.; Willeit, P.; Puntmann, V. O.; Aldama-Lopez, G.; Shah, A. M.; Domenech, N.; Mayr, M. Proteomics analysis of cardiac extracellular matrix remodeling in a porcine model of ischemia/reperfusion injury. Circulation 2012, 125 (6), 789-802.
22. Parker, B. L.; Palmisano, G.; Edwards, A. V.; White, M. Y.; Engholm-Keller, K.; Lee, A.; Scott, N. E.; Kolarich, D.; Hambly, B. D.; Packer, N. H.; Larsen, M. R.; Cordwell, S. J. Quantitative N-linked glycoproteomics of myocardial ischemia and reperfusion injury reveals early remodeling in the extracellular environment. Mol. Cell. Proteomics 2011, 10 (8), M110 006833.
23. Amin, P.; Singh, M.; Singh, K. beta-Adrenergic Receptor-Stimulated Cardiac Myocyte Apoptosis: Role of beta1 Integrins. J. Signal Transduct. 2011, 2011, 179057.
24. Heino, J. The collagen receptor integrins have distinct ligand recognition and signaling functions. Matrix Biol. 2000, 19 (4), 319-23.
25. Lee, S. W.; Won, J. Y.; Lee, H. Y.; Lee, H. J.; Youn, S. W.; Lee, J. Y.; Cho, C. H.; Cho, H. J.; Oh, S.; Chae, I. H.; Kim, H. S. Angiopoietin-1 protects heart against ischemia/reperfusion injury through VE-cadherin dephosphorylation and myocardiac integrin-beta1/ERK/caspase-9 phosphorylation cascade. Mol. Med. 2011, 17 (9-10), 1095-106.
26. Lu, T.-Y.; Lin, B.; Kim, J.; Sullivan, M.; Tobita, K.; Salama, G.; Yang, L. Repopulation of decellularized mouse heart with human induced pluripotent stem cell-derived cardiovascular progenitor cells. Nat. Comm. 2013, 4.
27. Gordon, M. K.; Hahn, R. A. Collagens. Cell Tissue Res., 2010, 339 (1), 247-57.
28. Chapman, D.; Weber, K. T.; Eghbali, M. Regulation of fibrillar collagen types I and III and basement membrane type IV collagen gene expression in pressure overloaded rat myocardium. Circulation Res., 1990, 67 (4), 787-94.
29. Iruela-Arispe, M. L.; Sage, E. H. Expression of type VIII collagen during morphogenesis of the chicken and mouse heart. Dev. Biol., 1991, 144 (1), 107-18.
30. Avery, N. C.; Bailey, A. J.; Barocas, V. H.; Biewener, A. A.; Blank, R. D.; Boskey, A. L.; Buehler, M. J.; Currey, J.; Fratzl, P.; Gupta, H. S.; Holzapfel, G. A.; Hulmes, D. J. S.; Ker, R. F.; Kjær, M.; Landis, W. J.; Magnusson, S. P.; Meek, K. M.; Purslow, P. P.; Sander, E. A.; Silver, F. H.; Wess, T. J.; Zaslansky, P. Collagen: Structure and Mechanics; Springer Science+Business Media, LLC 1 edition (May 30, 2008): New York, US, 2008.

31. Weber, K. T. Cardiac interstitium in health and disease: The fibrillar collagen network. J. Am. Coll. Cardiol. 1989, 13 (7), 1637-1652.
32. Adachi, E.; Hopkinson, I.; Hayashi, T. Basement-membrane stromal relationships: interactions between collagen fibrils and the lamina densa. Int. Rev. Cytol., 1997, 173, 73-156.
33. Marijianowski, M. M.; Teeling, P.; Mann, J.; Becker, A. E. Dilated cardiomyopathy is associated with an increase in the type I/type III collagen ratio: a quantitative assessment. J. Am. Coll. Cardiol. 1995, 25 (6), 1263-72.
34. Graham, H. K.; Horn, M.; Trafford, A. W. Extracellular matrix profiles in the progression to heart failure. European Young Physiologists Symposium Keynote Lecture-Bratislava 2007. Acta Physiol., (Oxford, England) 2008, 194 (1), 3-21.
35. Burton, A. C. Relation of structure to function of the tissues of the wall of blood vessels. Physiol. Rev., 1954, 34 (4), 619-42.
36. Borg, T. K.; Ranson, W. F.; Moslehy, F. A.; Caulfield, J. B. Structural basis of ventricular stiffness. Lab. Invest.; 1981, 44 (1), 49-54.
37. de Souza, R. R. Aging of myocardial collagen. Biogerontology 2002, 3 (6), 325-35.
38. Gazoti Debessa, C. R.; Mesiano Maifrino, L. B.; Rodrigues de Souza, R. Age related changes of the collagen network of the human heart. Mech. Ageing Dev., 2001, 122 (10), 1049-58.
39. Verzar, F. The stages and consequences of ageing of collagen. Gerontologia 1969, 15 (2), 233-9.
40. Herpel, E.; Pritsch, M.; Koch, A.; Dengler, T. J.; Schirmacher, P.; Schnabel, P. A. Interstitial fibrosis in the heart: differences in extracellular matrix proteins and matrix metalloproteinases in end-stage dilated, ischaemic and valvular cardiomyopathy. Histopathology 2006, 48 (6), 736-47.
41. Birkedal-Hansen, H.; Yamada, S.; Windsor, J.; Pollard, A. H.; Lyons, G.; Stetler-Stevenson, W.; Birkedal-Hansen, B. Matrix metalloproteinases. Curr. Protoc. Cell Biol., 2008, Chapter 10, Unit 10.18.
42. Shamhart, P. E.; Meszaros, J. G. Non-fibrillar collagens: key mediators of post-infarction cardiac remodeling? J. Mol. Cell Cardiol., 2010, 48 (3), 530-7.
43. Creemers, E. E.; Cleutjens, J. P.; Smits, J. F.; Daemen, M. J. Matrix metalloproteinase inhibition after myocardial infarction: a new approach to prevent heart failure? Circ Res 2001, 89 (3), 201-10.
44. Wang, J. J.; Christman, K. L. 2-Hydrogels for cardiac repair. In Cardiac Regeneration and Repair; Woodhead Publishing, 2014, pp 17-48.
45. Lin, Y. D.; Yeh, M. L.; Yang, Y. J.; Tsai, D. C.; Chu, T. Y.; Shih, Y. Y.; Chang, M. Y.; Liu, Y. W.; Tang, A. C.; Chen, T. Y.; Luo, C. Y.; Chang, K. C.; Chen, J. H.; Wu, H. L.; Hung, T. K.; Hsieh, P. C. Intramyocardial peptide nanofiber injection improves postinfarction ventricular remodeling and efficacy of bone marrow cell therapy in pigs. Circulation 2010, 122 (11 Suppl), S132-41.
46. Leor, J.; Tuvia, S.; Guetta, V.; Manczur, F.; Castel, D.; Willenz, U.; Petnehazy, O.; Landa, N.; Feinberg, M. S.; Konen, E.; Goitein, O.; Tsur-Gang, O.; Shaul, M.; Klapper, L.; Cohen, S. Intracoronary injection of in situ forming alginate hydrogel reverses left ventricular remodeling after myocardial infarction in Swine. J. Am. Coll. Cardiol. 2009, 54 (11), 1014-23.
47. Seif-Naraghi, S. B.; Singelyn, J. M.; Salvatore, M. A.; Osborn, K. G.; Wang, J. J.; Sampat, U.; Kwan, O. L.; Strachan, G. M.; Wong, J.; Schup-Magoffin, P. J.; Braden, R. L.; Bartels, K.; DeQuach, J. A.; Preul, M.; Kinsey, A. M.; DeMaria, A. N.; Dib, N.; Christman, K. L. Safety and efficacy of an injectable extracellular matrix hydrogel for treating myocardial infarction. Sci Transl Med., 2013, 5 (173), 173ra25.
48. Dorsey, S. M.; McGarvey, J. R.; Wang, H.; Nikou, A.; Arama, L.; Koomalsingh, K. J.; Kondo, N.; Gorman, J. H., 3rd; Pilla, J. J.; Gorman, R. C.; Wenk, J. F.; Burdick, J. A. MRI evaluation of injectable hyaluronic acid-based hydrogel therapy to limit ventricular remodeling after myocardial infarction. Biomaterials 2015, 69, 65-75.
49. Rao, S. V.; Zeymer, U.; Douglas, P. S.; Al-Khalidi, H.; Liu, J.; Gibson, C. M.; Harrison, R. W.; Joseph, D. S.; Heyrman, R.; Krucoff, M. W. A randomized, double-blind, placebo-controlled trial to evaluate the safety and effectiveness of intracoronary application of a novel bioabsorbable cardiac matrix for the prevention of ventricular remodeling after large ST-segment elevation myocardial infarction: Rationale and design of the PRESERVATION I trial. Am. Heart J. 2015, 170 (5), 929-937.
50. Anker, S. D.; Coats, A. J. S.; Cristian, G.; Dragomir, D.; Pusineri, E.; Piredda, M.; Bettari, L.; Dowling, R.; Volterrani, M.; Kirwan, B.-A.; Filippatos, G.; Mas, J.-L.; Danchin, N.; Solomon, S. D.; Lee, R. J.; Ahmann, F.; Hinson, A.; Sabbah, H. N.; Mann, D. L. A prospective comparison of alginate-hydrogel with standard medical therapy to determine impact on functional capacity and clinical outcomes in patients with advanced heart failure (AUGMENT-HF trial). Eur. Heart J. 2015.
51. Rane, A. A.; Chuang, J. S.; Shah, A.; Hu, D. P.; Dalton, N. D.; Gu, Y.; Peterson, K. L.; Omens, J. H.; Christman, K. L. Increased infarct wall thickness by a bio-inert material is insufficient to prevent negative left ventricular remodeling after myocardial infarction. PloS one 2011, 6 (6), e21571.
52. Zhang, P.; Ruel, M.; Suuronen, E. J. Collagen biomaterials for cardiac tissue engineering applications. In Tissue engineering: roles, materials and applications, Barnes, S. J.; Harris, L. P., Eds.; Nova Science Publishers Inc., 2008, pp Chap. 3; 67-82.
53. Chattopadhyay, S.; Raines, R. T. Review collagen-based biomaterials for wound healing. Biopolymers 2014, 101 (8), 821-33.
54. Rane, A. A.; Christman, K. L. Biomaterials for the treatment of myocardial infarction: a 5-year update. J. Am. Coll. Cardiol. 2011, 58 (25), 2615-29.
55. Badylak, S. F.; Freytes, D. O.; Gilbert, T. W. Extracellular matrix as a biological scaffold material: Structure and function. Acta Biomater. 2009, 5 (1), 1-13.
56. Kuraitis, D.; Giordano, C.; Ruel, M.; Musaro, A.; Suuronen, E. J. Exploiting extracellular matrix-stem cell interactions: a review of natural materials for therapeutic muscle regeneration. Biomaterials 2011, 33 (2), 428-43.
57. Kuraitis, D.; Hou, C.; Zhang, Y.; Vulesevic, B.; Sofrenovic, T.; McKee, D.; Sharif, Z.; Ruel, M.; Suuronen, E. J. Ex vivo generation of a highly potent population of circulating angiogenic cells using a collagen matrix. J. Mol. Cell Cardiol., 2011, 51 (2), 187-97.
58. Dai, W.; Wold, L. E.; Dow, J. S.; Kloner, R. A. Thickening of the infarcted wall by collagen injection improves left ventricular function in rats: a novel approach to preserve cardiac function after myocardial infarction. J. Am. Coll. Cardiol. 2005, 46 (4), 714-9.
59. Ahmadi, A.; McNeill, B.; Vulesevic, B.; Kordos, M.; Mesana, L.; Thorn, S.; Renaud, J. M.; Manthorp, E.; Kuraitis, D.; Toeg, H.; Mesana, T. G.; Davis, D. R.;

Beanlands, R. S.; DaSilva, J. N.; deKemp, R. A.; Ruel, M.; Suuronen, E. J. The role of integrin alpha2 in cell and matrix therapy that improves perfusion, viability and function of infarcted myocardium. Biomaterials 2014, 35 (17), 4749-58.

60. Huang, N. F.; Yu, J.; Sievers, R.; Li, S.; Lee, R. J. Injectable biopolymers enhance angiogenesis after myocardial infarction. Tissue Eng. 2005, 11 (11-12), 1860-6.

61. Seif-Naraghi, S. B.; Singelyn, J. M.; Salvatore, M. A.; Osborn, K. G.; Wang, J. J.; Sampat, U.; Kwan, O. L.; Strachan, G. M.; Wong, J.; Schup-Magoffin, P. J.; Braden, R. L.; Bartels, K.; DeQuach, J. A.; Preul, M.; Kinsey, A. M.; DeMaria, A. N.; Dib, N.; Christman, K. L. Safety and efficacy of an injectable extracellular matrix hydrogel for treating myocardial infarction. Sci. Transl. Med. 2013, 5 (173), 173ra25.

62. Blackburn, N. J.; Sofrenovic, T.; Kuraitis, D.; Ahmadi, A.; McNeill, B.; Deng, C.; Rayner, K. J.; Zhong, Z.; Ruel, M.; Suuronen, E. J. Timing underpins the benefits associated with injectable collagen biomaterial therapy for the treatment of myocardial infarction. Biomaterials 2015, 39, 182-92.

63. Ahmadi, A. et al., The role of integrin alpha2 in cell and matrix therapy that improves perfusion, viability and function of infarcted myocardium. Biomaterials 2014, 35(17):4749-4758. https://www.ncbi.nlm.nih.gov/pubmed/24631247.

64. Rane, A. A.; Christman, K. L. Biomaterials for the treatment of myocardial infarction: a 5-year update. J Am Coll Cardiol 2011, 58 (25), 2615-29.

65. Badylak, S. F.; Freytes, D. O.; Gilbert, T. W. Extracellular matrix as a biological scaffold material: Structure and function. Acta Biomater 2009, 5 (1), 1-13.

66. Kuraitis, D.; Hou, C.; Zhang, Y.; Vulesevic, B.; Sofrenovic, T.; McKee, D.; Sharif, Z.; Ruel, M.; Suuronen, E. J. Ex vivo generation of a highly potent population of circulating angiogenic cells using a collagen matrix. J Mol Cell Cardiol 2011, 51 (2), 187-97.

67. Dai, W.; Wold, L. E.; Dow, J. S.; Kloner, R. A. Thickening of the infarcted wall by collagen injection improves left ventricular function in rats: a novel approach to preserve cardiac function after myocardial infarction. J Am Coll Cardiol 2005, 46 (4), 714-9.

68. Huang, N. F.; Yu, J.; Sievers, R.; Li, S.; Lee, R. J. Injectable biopolymers enhance angiogenesis after myocardial infarction. Tissue Eng 2005, 11 (11-12), 1860-6.

69. Charriere, G.; Bejot, M.; Schnitzler, L.; Ville, G.; Hartmann, D. J. Reactions to a bovine collagen implant. Clinical and immunologic study in 705 patients. J. Am. Acad. Dermatol., 1989, 21 (6), 1203-8.

70. Badylak, S. F.; Gilbert, T. W. Immune response to biologic scaffold materials. Semin. Immunol., 2008, 20 (2), 109-16.

71. Jourdan-Lesaux, C.; Zhang, J.; Lindsey, M. L. Extracellular matrix roles during cardiac repair. Life Sci 2010, 87 (13-14), 391-400.

72. McEwan, K.; Padavan, D. T.; Ellis, C.; McBane, J. E.; Vulesevic, B.; Korbutt, G. S.; Suuronen, E. J. Collagen-chitosan-laminin hydrogels for the delivery of insulin-producing tissue. medicine. Tissue Eng. Regen. Med., 2016, 10(10), E397-E408.

73. Kuraitis, D.; Ebadi, D.; Zhang, P.; Rizzuto, E.; Vulesevic, B.; Padavan, D. T.; Al Madhoun, A.; McEwan, K. A.; Sofrenovic, T.; Nicholson, K.; Whitman, S. C.; Mesana, T. G.; Skerjanc, I. S.; Musaro, A.; Ruel, M.; Suuronen, E. J. Injected matrix stimulates myogenesis and regeneration of mouse skeletal muscle after ischaemic injury. Eur. Cell Mater., 2012, 24, 175-95; discussion 195-6.

74. Ravichandran, R.; Islam, M. M.; Alarcon, E. I.; Samanta, A.; Wang, S.; Lundstrom, P.; Hilborn, J.; Griffith, M.; Phopase, J. Functionalised type-I collagen as a hydrogel building block for bio-orthogonal tissue engineering applications. J. Mater. Chem. B. 2016, 4 (2), 318-326.

75. Lutgens, E.; Daemen, M. J.; de Muinck, E. D.; Debets, J.; Leenders, P.; Smits, J. F. Chronic myocardial infarction in the mouse: cardiac structural and functional changes. Cardiovasc. Res. 1999, 41 (3), 586-93.

76. Kumar, D.; Hacker, T. A.; Buck, J.; Whitesell, L. F.; Kaji, E. H.; Douglas, P. S.; Kamp, T. J. Distinct mouse coronary anatomy and myocardial infarction consequent to ligation. Coron. Artery Dis. 2005, 16 (1), 41-4.

77. Kumar, D.; Hacker, T. A.; Buck, J.; Whitesell, L. F.; Kaji, E. H.; Douglas, P. S.; Kamp, T. J. Distinct mouse coronary anatomy and myocardial infarction consequent to ligation. Coron Artery Dis 2005, 16 (1), 41-4.

78. Ahmadi, A.; Toeg, H.; DaSilva, J. N.; Kordos, M.; Thorn, S.; Renaud, J. M.; Mesana, T. G.; Beanlands, R. S.; deKemp, R. A.; Suuronen, E. J.; Ruel, M. A collagen matrix for endothelial progenitor cell therapy improves myocardial function through enhanced cell retention and phenotype in a mouse model of myocardial infarction. Circulation 2010, 122, A19374.

79. Zhang, Y.; DaSilva, J. N.; Hadizad, T.; Thorn, S.; Kuraitis, D.; Renaud, J. M.; Ahmadi, A.; Kordos, M.; deKemp, R.; Beanlands, R. S.; Suuronen, E. J.; Ruel, M. 18F-FDG cell labeling may underestimate transplanted cell homing: more accurate, efficient and stable cell labeling with hexadecyl-4-[18F]fluorobenzoate for in vivo tracking of intramyocardially injected human progenitor cells by positron emission tomography. Cell Trans., 2012, 21 (9), 1821-35

80. Blackburn, N. J.; Sofrenovic, T.; Kuraitis, D.; Ahmadi, A.; McNeill, B.; Deng, C.; Rayner, K. J.; Zhong, Z.; Ruel, M.; Suuronen, E. J. Timing underpins the benefits associated with injectable collagen biomaterial therapy for the treatment of myocardial infarction. Biomaterials 2015, 39, 182-92.

81. Stöger, J. L.; Gijbels, M. J. J.; van der Velden, S.; Manca, M.; van der Loos, C. M.; Biessen, E. A. L.; Daemen, M. J. A. P.; Lutgens, E.; de Winther, M. P. J. Distribution of macrophage polarization markers in human atherosclerosis. Atherosclerosis 2012, 225 (2), 461-468.

82. Koch, A.; Feucht, S.; Helmke, B. M.; Dengler, T. J.; Haass, M.; Sack, F. U.; Karck, M.; Schnabel, P. A. Interstitial leukocytes in right ventricular endomyocardial biopsies after heart transplantation in patients with complicated versus uneventful postoperative course. Transplant Proc., 2008, 40 (4), 947-50.

83. Junankar, S. R.; Eichten, A.; Kramer, A.; de Visser, K. E.; Coussens, L. M. Analysis of Immune Cell Infiltrates during Squamous Carcinoma Development. J. Investig. Dermatol. Symp. P. 2006, 11 (1), 36-43.

84. You, J. O.; Rafat, M.; Ye, G. J.; Auguste, D. T. Nanoengineering the heart: conductive scaffolds enhance connexin 43 expression. Nano Lett., 2011, 11 (9), 3643-8.

85. Dvir, T.; Timko, B. P.; Brigham, M. D.; Naik, S. R.; Karajanagi, S. S.; Levy, O.; Jin, H.; Parker, K. K.; Langer, R.; Kohane, D. S. Nanowired three-dimensional cardiac patches. Nature Nanotech., 2011, 6 (11), 720-5.

86. Ellis, C. E.; Vulesevic, B.; Suuronen, E.; Yeung, T.; Seeberger, K.; Korbutt, G. S. Bioengineering a highly vascularized matrix for the ectopic transplantation of islets. Islets 2013, 5 (5), 216-25.

87. Suuronen, E. J.; Veinot, J. P.; Wong, S.; Kapila, V.; Price, J.; Griffith, M.; Mesana, T. G.; Ruel, M. Tissue-engineered injectable collagen-based matrices for improved cell delivery and vascularization of ischemic tissue using CD133+ progenitors expanded from the peripheral blood. Circulation 2006, 114 (1 Suppl), I138-44.
88. McBane, J. E.; Vulesevic, B.; Padavan, D. T.; McEwan, K. A.; Korbutt, G. S.; Suuronen, E. J. Evaluation of a collagen-chitosan hydrogel for potential use as a pro-angiogenic site for islet transplantation. PloS one 2013, 8 (10), e77538.
89. Lin, G.; Zhang, X.; Ren, J.; Pang, Z.; Wang, C.; Xu, N.; Xi, R. Integrin signaling is required for maintenance and proliferation of intestinal stem cells in Drosophila. Dev. Biol., 2013, 377 (1), 177-87.
90. Kawamoto, A.; Tkebuchava, T.; Yamaguchi, J.; Nishimura, H.; Yoon, Y. S.; Milliken, C.; Uchida, S.; Masuo, O.; Iwaguro, H.; Ma, H.; Hanley, A.; Silver, M.; Kearney, M.; Losordo, D. W.; Isner, J. M.; Asahara, T. Intramyocardial transplantation of autologous endothelial progenitor cells for therapeutic neovascularization of myocardial ischemia. Circulation 2003, 107 (3), 461-8.
91. Chavakis, E.; Hain, A.; Vinci, M.; Carmona, G.; Bianchi, M. E.; Vajkoczy, P.; Zeiher, A. M.; Chavakis, T.; Dimmeler, S. High-mobility group box 1 activates integrin-dependent homing of endothelial progenitor cells. Circulation Res., 2007, 100 (2), 204-12.
92. Carmona, G.; Chavakis, E.; Koehl, U.; Zeiher, A. M.; Dimmeler, S. Activation of Epac stimulates integrin-dependent homing of progenitor cells. Blood 2008, 111 (5), 2640-6.
93. Jourdan-Lesaux, C.; Zhang, J.; Lindsey, M. L. Extracellular matrix roles during cardiac repair. Life Sci., 2010, 87 (13-14), 391-400.
94. Maeda, K.; Tiwari-Pandey, R.; Ruel, M.; Suuronen, E. J. Matrix Therapies for Cell Support and Cardiac Repair. In Biomaterials for Cardiac Regeneration, Suuronen, E. J.; Ruel, M., Eds.; Springer International Publishing, 2015, pp 117-158.
95. Pfeffer, M. A.; Braunwald, E. Ventricular remodeling after myocardial infarction. Experimental observations and clinical implications. Circulation 1990, 81 (4), 1161-1172.
96. Sutton, M. G. S. J.; Sharpe, N. Left Ventricular Remodeling After Myocardial Infarction. Pathophysiology and Therapy 2000, 101 (25), 2981-2988.
97. Pfeffer, M. A.; Pfeffer, J. M.; Fishbein, M. C.; Fletcher, P. J.; Spadaro, J.; Kloner, R. A.; Braunwald, E. Myocardial infarct size and ventricular function in rats. Circulation Res., 1979, 44 (4), 503-12.
98. Mozaffarian, D.; Benjamin, E. J.; Go, A. S.; Arnett, D. K.; Blaha, M. J.; Cushman, M.; de Ferranti, S.; Despres, J.-P.; Fullerton, H. J.; Howard, V. J.; Huffman, M. D.; Judd, S. E.; Kissela, B. M.; Lackland, D. T.; Lichtman, J. H.; Lisabeth, L. D.; Liu, S.; Mackey, R. H.; Matchar, D. B.; McGuire, D. K.; Mohler, E. R.; Moy, C. S.; Muntner, P.; Mussolino, M. E.; Nasir, K.; Neumar, R. W.; Nichol, G.; Palaniappan, L.; Pandey, D. K.; Reeves, M. J.; Rodriguez, C. J.; Sorlie, P. D.; Stein, J.; Towfighi, A.; Turan, T. N.; Virani, S. S.; Willey, J. Z.; Woo, D.; Yeh, R. W.; Turner, M. B. Heart Disease and Stroke Statistics-2015 Update. A Report From the American Heart Association 2015, 131 (4), e29-e322.
99. Lister, Z.; Rayner, K. J.; Suuronen, E. J. How Biomaterials Can Influence Various Cell Types in the Repair and Regeneration of the Heart after Myocardial Infarction. Frontiers in Bioengineering and Biotechnology 2016, 4 (62).
100. Quijada, P., et al., Cardiac Stem Cell Hybrids Enhance Myocardial Repair. Circulation Research. 117:695-706 (2015).
101. World Health Organization, January 2017, vol. 2017; Public Health Agency of Canada, 2017, vol. 2017.
102. Abdelwahid, E., et al., Stem Cell Death and Survival in Heart Regeneration and Repair, Apoptosis, 21:252-268 (2016).
103. Patten, R. D., et al., Small Animal Models of Heart Failure: Development of Novel Therapies, Past and Present. Circ. Heart Fail. 2:138-144 (2009).
104. Yang, F., et al., Myocardial Infarction and Cardiac Remodelling in Mice. Exp. Physiol., 87:547-555 (2002).
105. Christia, P., et al., Frangogiannis, Systematic Characterization of Myocardial Inflammation, Repair, and Remodeling in a Mouse Model of Reperfused Myocardial Infarction. J Histochem Cytochem. 61:555-570 (2013).
106. Prabhu, S. D., et al., The Biological Basis for Cardiac Repair after Myocardial Infarction: From Inflammation to Fibrosis. Circ. Res, 119:91-112 (2016).
107. Bassat, E., et al., The Extracellular Matrix Protein Agrin Promotes Heart Regeneration in Mice. Nature, 547:179 (2017).
108. Allison, S., et al., Electroconductive Nanoengineered Biomimetic Hybrid Fibers for Cardiac Tissue Engineering. J Mat Chem B, 5:2402-2406 (2017).
109. Hosoyama, K., et al., Multi-functional thermo-cross-linkable collagen-metal nanoparticle composites for tissue regeneration: nanosilver vs. nanogold. RSC Adv, 7:47704-47708 (2017).
110. Liang, W., Wnt Signalling Suppresses voltage-Dependent Na+ Channel Expression in Postnatal Rat Cardiomyocytes. J Physiology, 593:1147-1157 (2015).
111. Weischenfeldt, J., et al., Bone Marrow-Derived macrophages (BMM): Isolation and Applications. CSH Protocols, 2008, pdb.prot5080 (2008).
112. Heidt, T., et al., Differential Contribution of Monocytes to Heart Macrophages in Steady-State and After Myocardial Infarction. Circulation Research, 115:284-295 (2014).

What is claimed is:

1. A biocompatible and/or biodegradable hydrogel composition comprising native collagen and chondroitin sulfate, the collagen and chondroitin sulfate being at least partially chemically cross-linked thereby forming a matrix, wherein the hydrogel composition gels at 37° C. in less than about 10 min, and wherein the native collagen is a 1% w/v solution comprising recombinant human collagen type I (rHCI), recombinant human collagen type III (rHCIII), or a combination thereof.

2. The hydrogel composition according to claim 1, wherein the native collagen and the chondroitin sulfate are chemically cross-linked by 1-ethyl-3-(3-dimethylaminopropyl)carbodiimide (EDC)-N-hydroxysuccinimide (NHS) chemical coupling reaction.

3. The hydrogel composition according to claim 1, wherein the hydrogel composition has a denaturation temperature greater than about 45° C.

4. The hydrogel composition according to claim 1, wherein the hydrogel composition has a viscosity of about 0.5 to about 4.5 Pa·s at 37° C., such as about 0.7 to about 1.7 Pa·s at 37° C., prior to cross-linking, and viscosity of about 9 to about 150 Pa·s at 37° C. after cross-linking.

5. The hydrogel composition according to claim 1, wherein the hydrogel matrix has a pore size range of about 5 to about 50 μm, such as about 10 to about 25 μm.

6. The hydrogel composition according to claim 1, wherein the hydrogel matrix is degraded by 10 U/mL type I collagenase in PBS solution at 37° C. at a rate of about 0.1 to about 2 mg/s, such as about 0.15 to about 0.65 mg/s.

7. The hydrogel composition according to claim 1, wherein a mass ratio of native collagen to chondroitin sulfate is about 1:4.

8. The hydrogel composition according to claim 1, wherein the native collagen and the chondroitin sulfate are chemically cross-linked by EDC-NHS cross-linking agent, and a mass ratio of native human collagen to chondroitin sulfate to NHS to EDC is about 1:4:0.5:0.3.

9. The hydrogel composition according to claim 1, wherein:
the native collagen is rHCI, the rHCI and the chondroitin sulfate are chemically cross-linked by EDC-NHS chemical coupling reaction at a mass ratio of rHCI to chondroitin sulfate to NHS to EDC of about 1:4:0.5:0.3, and the hydrogel matrix has a denaturation temperature of about 46° C., an average matrix pore size of about 11 μm, and the matrix is degraded by 10 U/mL type I collagenase in PBS solution at 37° C. at a rate of about 0.5 mg/s; or
wherein the native collagen is rHCIII, the rHCIII and the chondroitin sulfate are chemically cross-linked by EDC-NHS chemical coupling reaction at a mass ratio of rHCIII to chondroitin sulfate to NHS to EDC of about 1:4:0.5:0.3, and the hydrogel matrix has a denaturation temperature of about 50° C., an average matrix pore size of about 24 μm, and the matrix is degraded by 10 U/mL type I collagenase in PBS solution at 37° C. at a rate of about 0.2 mg/s.

10. The hydrogel composition according to claim 1, wherein the native collagen is a combination of rHCI and rHCIII.

11. A method for regenerating or repairing tissue, improving tissue function, mechanically stabilizing tissue, preventing tissue damage, or preventing tissue loss of function in a subject in need thereof, said method comprising:
providing a hydrogel composition as defined in claim 1; and
administering said hydrogel composition into affected tissue of the subject.

12. The method according to claim 11, wherein the tissue is cardiac tissue.

13. The method according to claim 12, wherein the hydrogel composition is administered by injection to the heart following a myocardial infarction or ischemic event.

14. The method according to claim 13, wherein the hydrogel composition is administered to the heart by injection at a single time-point or by a plurality of injections at multiple time-points following the myocardial infarction or ischemic event.

15. The method according to claim 13, wherein the hydrogel composition prevents loss of cardiac mechanical properties, prevents cardiac remodeling, reduces fibrosis and/or infarct area, improves vascularity of infarcted heart muscle, or improves cardiac function following the myocardial infarction or ischemic event.

16. A method for preparing a hydrogel composition as defined in claim 1, said method comprising:
providing a solution of native collagen;
providing a solution of chondroitin sulfate;
providing an EDC and NHS solution;
mixing the solution of native collagen with the solution of chondroitin sulfate, thereby forming a first mixed solution; and
mixing the first mixed solution with the EDC and NHS solution, thereby initiating cross-linking the native collagen and chondroitin sulfate to form a hydrogel matrix composition.

17. The method according to claim 16, wherein a mass ratio of native collagen to chondroitin sulfate to NHS to EDC in the chemical cross-linking mixing step is about 1:4:0.5:0.3.

18. The method according to claim 16, further comprising a step of adding an NaOH solution to the chemically cross-linked hydrogel composition to adjust the pH of the hydrogel composition to a physiologically acceptable level.

19. The method according to claim 4, wherein the hydrogel composition has a viscosity prior to cross-linking is about 0.7 to about 1.7 Pa·s at 37° C. and a viscosity of about 9 to about 150 Pa·s at 37° C. after cross-linking.

20. The method according to claim 5, wherein the hydrogel matrix has a pore size range of about 10 to about 25 μm.

21. The method of claim 6, wherein the hydgel mastrix is degraded by 10 U/mL type I collagenase in PBS solution at 37° C. at a rate of about 0.15 to about 0.65 mg/s.

* * * * *